United States Patent [19]

Greenlee et al.

[11] Patent Number: 5,356,889
[45] Date of Patent: Oct. 18, 1994

[54] 2-(9-FLUORENONYL)-CARBAPENEM INTERMEDIATES

[75] Inventors: Mark L. Greenlee, Rahway; Frank P. DiNinno, Old Bridge; Lovji D. Cama, Tenafly; James V. Heck, Scotch Plains, all of N.J.

[73] Assignee: Merck & Co., Inc., Rahway, N.J.

[21] Appl. No.: 966,969

[22] Filed: Oct. 26, 1992

Related U.S. Application Data

[63] Continuation-in-part of Ser. No. 594,808, Oct. 9, 1990, abandoned, which is a continuation-in-part of Ser. No. 561,547, Aug. 1, 1990, Pat. No. 5,034,384.

[51] Int. Cl.⁵ .................. A01N 43/00; A61K 31/395; C07D 487/00
[52] U.S. Cl. ..................... 514/210; 540/302
[58] Field of Search ........................ 540/302; 514/210

[56] References Cited

U.S. PATENT DOCUMENTS

| | | |
|---|---|---|
| 4,260,627 | 4/1981 | Christensen et al. |
| 4,465,632 | 8/1984 | Christensen et al. |
| 4,543,257 | 9/1985 | Cama et al. |
| 4,675,317 | 6/1987 | DiNinno et al. |
| 4,775,669 | 10/1988 | Cama et al. |
| 4,892,869 | 1/1990 | Christensen et al. |
| 4,962,101 | 10/1990 | DiNinno et al. |
| 4,988,703 | 1/1991 | Norbeck et al. |
| 5,003,099 | 3/1991 | Mettler et al. |
| 5,011,832 | 4/1991 | DiNinno et al. |
| 5,011,848 | 4/1991 | Semeraro et al. |
| 5,015,260 | 5/1991 | Tamura et al. |
| 5,023,250 | 6/1991 | Adams et al. |
| 5,025,006 | 6/1991 | DiNinno |
| 5,025,007 | 6/1991 | Greenlee et al. |
| 5,026,869 | 6/1991 | Flaugh |
| 5,034,384 | 7/1991 | Greenlee et al. |

FOREIGN PATENT DOCUMENTS

| | | |
|---|---|---|
| 277743A1 | 8/1988 | European Pat. Off. |
| 472062A1 | 2/1992 | European Pat. Off. |

OTHER PUBLICATIONS

Ihara et al. J Chem Soc Chem Commun. 1988 pp. 9–10.
Bayles, R. et al. "A Versatile Synthesis of Carbapenems from Substituted Dihydropyrans" Tet// :et/ 20(48):6345–6348 (1988).
Bender, D. R. et al. "Diastereoselective Routes to a 1β-Methylcarbapenem Key Intermediate, Scope of Ate Complex Formation between Exter Enolates and Organoboranes and -alanes" J. Org. Chem. 57:2411–2418 (1992).
Bryce, M. R. et al. "Electrophilic Fluorination of Tin and Mercury Derivatives as a Route to Fluoroaromatics" Bull. Soc. Chi. 6:930–932 (1986).
Cama, L. D. et al. "Total Synthesis of Thienamycin Analogs-III Syntheses of 2-Aryl and 2-Heteroaryl Analogs of Thienamycin" Tetrahedron 39(15): 2531 to 2549 (1983).
Endo, M. "Syntheses of Chiral Intermediates of 1β-Methylcarbapenems: (3S),4R)-3-[1(R)-tert-butyl-dimethylsilyoxyethyl]-4-chloroazetidin-2-one and (3S,4S)-3-[1(R)-tert-butyldimethylsilyloxyethyl]4][1(-
(List continued on next page.)

*Primary Examiner*—Johann Richter
*Assistant Examiner*—Rebecca Cook
*Attorney, Agent, or Firm*—Richard C. Billups; Mark R. Daniel; Joseph F. DiPrima

[57] ABSTRACT

Disclosed are carbapenems of the formula

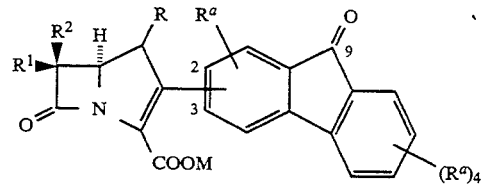

which are 2-(9-fluorenonyl)-carbapenems useful as antibacterial agents. Intermediates for preparation of these compounds is also disclosed.

32 Claims, No Drawings

OTHER PUBLICATIONS

R)-tert-butylthiocarbonylethyl]azetidin-2-one"Can. J. Chem. 65: 2140–2145 (1987).

Endo, M. "1β–Methylcarbapenem Intermediates. Stereoselective Synthesis of (3S,4R)-3-[1(R)-Tert-Butyl-dimethylsilyoxyethyl]-4-](1R)-3-Methoxycarbonyl-1-Methyl-2-Oxopropylazetidin-2-one and its Related Chemistry"Can. J. Chem. 66: 1400–1404 (1988).

Deziel, R. et al. "An Expeditious Synthesis of a 1β–Methylcarbapenem Key Intermediate" Tet. Let. 29(1):61-64(1988).

Fuentes, L. M. et al. "A Sterocontrolled Synthesis of an Important Intermediate for the Preparation of 1β–Methylcarbapenem Antibiotics" J. Org. Chem. 52:2563–2567 (1987).

Guthikonda, R. N. et al. "Structure–Activity Relationships in the 2-Arylcarbapenem Series: Synthesis of 1-Methyl-2-Arylcarbapenems" J. Med. Chem. 30: 871–880 (1987).

Hatanaka, M. "A Stereoselective Approach to 1β–Methylcarbapenem Antibiotic Starting from (R)-(-)-3-Hydroxybutyric Acid Ester" Tet. Let. 28(1): 83–86 (1987).

Ihara, M. et al. "Enantioselective Synthesis of the Key Intermediate of a 1β–Methycarbapenem Antibiotic by Way of Nitrone 1,3-Dipolar Cycloaddition" J. Chem. Soc. Perkin Trans I 2215–2221(1989).

Ihara, M. et al. "Highly Stereocontrolled Synthesis of the Key Intermediate of 1β–Methylcarbapenem Antibiotic via Intramolecular Nitrone 1,3-Dipolar Cycloaddition" J. Chem. Soc. Chem. Commun. 9–10 (1988).

Iimori, T. et al. "Simple, Stereocontrolled Synthesis of 1βMethylcarbapenem Antibiotics from 3(R)-Hydroxybutyric Acid" Tet. Let. 27(19): 2149–2152 (1986).

Ito, Y. et al. "Highly Stereocontrolled Synthesis of the 1β–Methylcarbapenem Key Intermediate by the Reformatsky Reaction of 3-(2-Bromopropionyl-2-Oxazolidone Derivatives with a 4-Acetoxy-2-Azetidinone" Tet. Let. 47(16/17): 2801–2820 (1991).

Ito, Y. et al. "A Highly Stereoselective Synthesis of a Key Intermediate of 1β–Methylcarbapenems Employing the Reformatsky Reaction of 3-(2-Bromopropionyl)-2-Oxazolidone Derivatives" Tet. Let. 28(52): 6625–6628 (1987).

Kaga, H. et al. "A Stereoselective Route to the Key Intermediate of 1β–Methylcarbapenems by Chemico-enzymatic Approach" Tet. Let. 30(1): 113–116 (1989).

Kawabata, T. et al. "A Novel and Efficient Synthesis of the Key Intermediate of 1β–Methylcarbapenem Antibiotics from (S)-Methyl 3-Hydroxy-3-Methylpropionate" Tet. Let. 27(51): 6241–6244 (1986).

Kim, C. U. et al. "Stereoselective Synthesis of 1β–Methylcarbapenem" Tet. Let. 28(5) 507–510 (1987).

Kitamura, M. et al. "Stereoselective Synthesis of a Precursor of 1β–Methylcarbapenems" Tet. Let. 31(4): 549–552 (1990).

Kobayashi, Y. et al. "A Highly Stereoselective Synthesis of the 1β–Methycarbapenem Key Intermediate from (R)-3-Hydroxybutyric Acid" Tet. Let. 48(1): 55–66 (1992).

Martel, A. et al. "2-Picolyl Thioesters; a useful Synthon for the preparation of 1-β-Alkyl Carbapenem Intermediates" Can. J. Chem. 66: 1537–1539 (1988).

Nagao, Y. et al. "Highly Diastereoselective Alkylation onto 4-Acetoxy-2-Azetidinones Employing Tin(II) Enolates of C4-Chiral 3-Acyl-1,3-Thiazolidine-2-Thiones" J. Am. Chem. Soc. 108: 4673–4675 (1986).

Ohta, T. et al. "Asymmetric Hydrogenation of Unsaturated Carboxylic Acids Catalyzed by BINAP–Ruthenium (II) Complexes" J. Org. Chem. 52: 3174–3176 (1987).

Kawabata, T. et al. "A Novel and Efficient Synthesis of the Key Intermediate of 1β–Methylcarbepenem Antibiotics Employing [2+2]-Cycloaddition Reaction of Diketene with a Chiral Imine" Tet. Let. 44(8): 2149–2165 (1988).

Prasad, J. S. et al. "Acyclic Stereochemical Control Using Hexacarbonyldicobalt Stabilized Propargyl Cations. A Highly Stereoselective Route to 1β–Methylcarbapenem Precursors" Tet. Let. 28(17): 1857–1860 (1987).

Rama Rao, A. V. et al. "A Simple Route to the Key Intermediate of 1β–Methyl Thienamycin" Tetrahedron: Asymmetry 2(4): 255–256 (1991).

Rama Rao, A. V. et al. "Stereocontrolled Approaches to the Key Intermediate of 1β–Methylthienamycin" Tet. Let. 31(2): 271–274 (1990).

Shibata, T. et al. "Synthetic Study of 1-Substituted Carbapenem Antibiotics" Tet. Let. 26(39): 4739–4742 (1985).

(List continued on next page.)

OTHER PUBLICATIONS

Sowin, T. J. et al. "Enantioselective Synthesis of the 1β-Methylcarbapenems via Cycoaddition of 3-Siloxypentadiene and 4-Acetoxyazetidinone" J. Org. Chem. 53: 4154–4156 (1988).

Shirai, F. et al. "A Novel, Double-Asymmetric Aldol Approach to the Synthesis of a 1β-Methyl Carbapenem Antibiotic Precursor" Tet. Let. 29(49): 6461–6464 (1988).

Shirai, F. et al. "A New Approach to the Chiral Synthesis of the 1β-Methylcarbapenem Key Precursor Using an Achiral Ketone Sn(II) Enolate" J. Org. Chem. 52: 5491–5492(1987).

Shirai, F. et al. "A New Synthetic Route to the Key Precursor of 1β-Methylcarbapenem Antibiotics from (S)=-Methyl 3-Hydroxy-2-Methylpropanoate" Chem. Let. 445–448 (1989).

Udodong, U. E. et al. "Formal Total Synthesis of 1β-Methylcarbapenem via a Novel Route to Deoxyamino Sugars" J. Org. Chem. 54: 2103–2112 (1989).

Udodong, U. E. et al. "Electrophilic Amination as a Route to Deoxyamino Sugars: Synthesis of the Key Intermediate for 1β-Methylcarbapenem" J. Org. Chem. 53: 2131–2132 (1988).

Uyeo, S. et al. "A Simple and Stereocontrolled Synthesis of a 1β-Methylcarbapenem Key Intermediate by Means of Organosilicon Chemistry" Tet. Let. 32(19): 2143–2144 (1991).

2-(9-FLUORENONYL)-CARBAPENEM INTERMEDIATES

CROSS REFERENCE TO RELATED APPLICATIONS

This application is a continuation in part of U.S. application Ser. No. 07/594,808, filed on Oct. 9, 1990, now abandoned, which was a continuation in part of U.S. application Ser. No. 07/561,547 filed on Aug. 1, 1990, now U.S. Pat. No. 5,034,384, priority of which is claimed hereunder.

BACKGROUND OF THE INVENTION

The present invention relates to antibacterial agents of the carbapenem class, in which the 2-position side-chain is characterized by a 9-fluorenone moiety, substituted by various cationic and neutral substituents, as described in more detail further below.

Thienamycin was an early carbapenem antibacterial agent having a broad spectrum; it has the following formula:

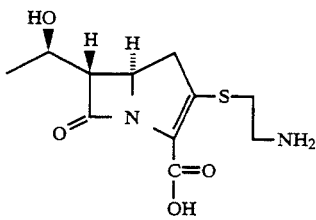

Later, N-formimidoyl thienamycin was discovered; it has the formula:

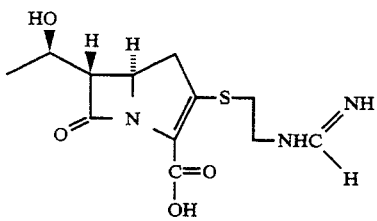

The 2-(9-fluorenonyl)carbapenems of the present invention are not characterized by a broad antibacterial spectrum such as that of thienamycin or N-formimidoyl thienamycin. Rather their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

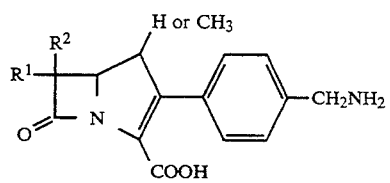

However, there is no description of or suggestion of a substituted-fluoren-9-onyl 2-substituent such as characterizes the compounds of the present invention, nor is there any suggestion of the surprisingly better anti-MRSA/MRCNS activity of the compounds of the present invention.

EP-A-0277 743 describes a particular class of compounds of the formula:

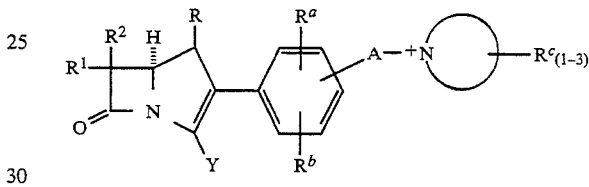

but this limited teaching in no way suggests the totally different compounds of the present invention, nor their surprisingly better anti-MRSA/MRCNS activity.

Recently, Merck & Co. has filed applications, U.S. Ser. Nos. 561,541 and 561,547 (Attorney Docket Numbers 17938 and 18093, respectively), disclosing 2- and 3-fluoren-9-onyl-2-carbapenems as having anti-MRSA/MRCNS activity. The present invention discloses intermediates useful in the preparation of the 2- and 3-fluoren-9-onyl-2-carbapenem antibacterial agents.

SUMMARY OF THE INVENTION

The present invention provides novel carbapenem compounds of the formula:

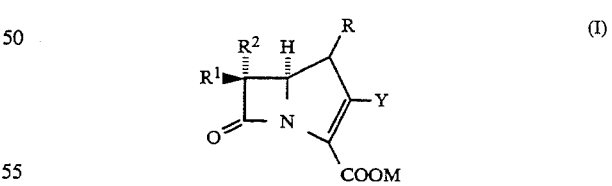

wherein:

Y is:

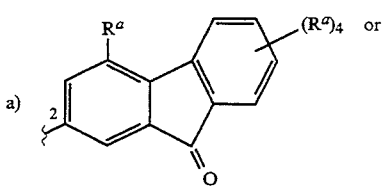

b) 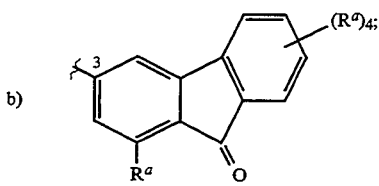

R is H or CH$_3$;

R$^1$ and R$^2$ are independently H, CH$_3$—, CH$_3$CH$_2$,—(CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

R$^a$ are independently selected from the group consisting of hydrogen and the radicals set out below, provided that one, but not more than one, R$^a$ is selected from Type I substitutents and zero to three R$^a$ radicals are selected from Type II substituents; wherein the Type I substituents are:

Type I.

a) 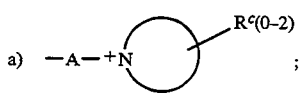

where

A is (CH$_2$)$_m$—Q—(CH$_2$)$_n$, where m is 0 to 6 and n is 1 to 6 and Q is a covalent bond, O, S, SO, SO$_2$, NH, —SO$_2$NH—, —NHSO$_2$—, —CONH—, —NHCO—, —SO$_2$N(C$_1$-C$_4$alkyl)—, —N(C$_1$-C$_4$alkyl)-SO$_2$—, —CON(C$_1$-C$_4$alkyl)—, —N(C$_1$-C$_4$alkyl)-CO—, —CH═CH—, —CO—, —OC(O)—, —C-(O)O— or N(C$_1$-C$_4$alkyl) and (CH$_2$)$_m$ is attached to the fluoren-9-one moiety;

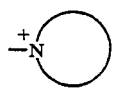

is a 5- or 6-membered monocyclic heterocycle or an 8-, 9- or 10-membered bicyclic heterocycle, the heterocycle containing a first nitrogen in an aromatic 5- or 6-membered first ring, with attachment of the heterocycle to A by way of said first nitrogen and said nitrogen is quaternary by virtue of the attachment in addition to the ring bonds thereto, with the first ring containing 0 or 1 of either O or S, with the first ring containing 0 to 3 additional nitrogen atoms, with the first ring optionally fused to a 3- or 4-membered moiety to form the optional second ring, with the moiety containing at least one carbon atom, with the moiety containing 0 to 1 of either O or S, with the moiety containing 0 to 2 nitrogen atoms, and with the moiety being saturated or unsaturated and the second ring aromatic or non-aromatic;

R$^c$ is R$^a$ as defined under Type II below, hydrogen, or —NR$^y$R$^z$ (where R$^y$ and R$^z$ are defined in II below), but independently selected from R$^a$ and from each other if more than one R$^c$ is present, and is attached to a carbon ring atom or a nitrogen heteroatom the valency of which is not satisfied by the ring bonds;

b) 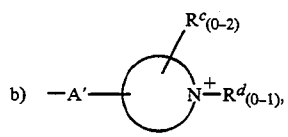

where

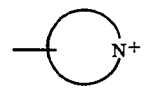

is a 5- or 6-membered monocyclic heterocycle or an 8-, 9- or 10-membered bicyclic heterocycle the heterocycle containing a first nitrogen in an aromatic 5- or 6-membered first ring, with said first nitrogen quaternary by virtue of a substituent R$^d$ in addition to the ring bonds thereto, with said first nitrogen neutral in the absence of a substituent R$^d$, with attachment of the heterocycle to A' by way of a carbon atom of a ring, with the first ring containing 0 or 1 of either O or S, with the first ring containing 0 to 2 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

R$^c$ is as defined above;

R$^d$ is hydrogen, NH$_2$, O$^-$, or C$_1$-C$_4$ alkyl (where the alkyl group is optionally mono-substituted with R$^q$ as defined under IIc below);

A' is (CH$_2$)$_m$—Q—(CH$_2$)$_n$, where m is 0 to 6 and n is 0 to 6, Q is as given above except that when m and n are both 0 then, Q is not a covalent bond and (CH$_2$)$_m$ is attached to the fluoren-9-one moiety;

c) —A$^p$—N$^+$R$^y$(R$^w$)$_{(0-1)}$(R$^z$), where

R$^y$ and R$^z$ are as defined under II below, R$^y$ and R$^z$ may further be together a C$_2$-C$_4$ alkylidene radical to form a ring (optionally mono-substituted with R$^q$ as defined below) interrupted by N(O)R$^e$ or N$^+$(R$^e$)$_2$ (where R$^e$ is hydrogen, C$_1$-C$_4$ alkyl, or C$_1$-C$_4$ alkyl mono-substituted with R$^q$ as defined below), R$^w$ is hydrogen, C$_{1-4}$ alkyl, O$^-$, NH$_2$, or absent in which case the nitrogen is neutral, R$^w$, R$^y$ and R$^z$ may further together form a C$_5$-C$_{10}$ tertiary alkylidene radical which with N$^+$ forms a bicyclic ring, where the tertiary alkylidene radical is optionally mono-substituted with R$^q$ as defined below and where the tertiary carbon of the tertiary alkylidene radical is optionally replaced with nitrogen, N$^+$R$^e$ (where R$^e$ is defined above) or N$^+$—O$^-$, p is 0 or 1, and A is as defined above;

d) 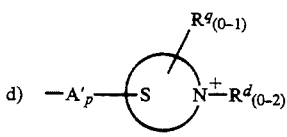

where

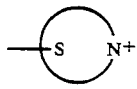

is a 5- or 6-membered monocyclic heterocycle or an 8- 9- or 10-membered bicyclic heterocycle, the heterocycle containing a first nitrogen in a first ring, with the first ring saturated or unsaturated and non-aromatic, with the first nitrogen quaternary by virtue of one or two substituents $R^d$ in addition to the ring bonds thereto, with the first nitrogen alternatively neutral by virtue of zero or one substituent $R^d$ in addition to the ring bonds thereto, with attachment of the heterocycle to A' by way of a carbon atom or non-quaternary nitrogen atom of a ring, with the first ring containing in addition to carbon and the first nitrogen, 0 to 1 of a member selected from the group consisting of the non-quaternary nitrogen of attachment, O, S, S(O), S(O)$_2$ and NR$^e$, where R$^e$ is defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

$R^d$ is defined above and where more than one $R^d$ is present on a nitrogen, at least one $R^d$ is hydrogen or $C_1$–$C_4$ alkyl;

A' is defined above;

is defined above; and $R^q$ is defined below;

and wherein the Type II substituents are:

Type II.

a) a trifluoromethyl group: —CF$_3$;

b) a halogen atom: —Br, —Cl, —F, or —I;

c) $C_1$–$C_4$ alkoxy radical: —OC$_{1-4}$ alkyl, wherein the alkyl is optionally mono-substituted by R$^q$, where
R$^q$ is a member selected from the group consisting of —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl or phenyl), tetrazolyl (where the point of attachment is the carbon atom of the tetrazole ring and one of the nitrogen atoms is mono-substituted by M$^a$ as defined above) and —SO$_3$M$^b$ (where M$^b$ is hydrogen or an alkali metal);

d) a hydroxy group: —OH;

e) a carbonyloxy radical: —O(C=O)R$^s$, where R$^s$ is $C_{1-4}$ alkyl or phenyl, each of which is optionally mono-substituted by R$^q$ as defined above;

f) a carbamoyloxy radical: —O(C=O)N(R$^y$)R$^z$, where
R$^y$ and R$^z$ are independently H, $C_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)— or —S(O)$_2$— to form a ring (where the ring is optionally mono-substituted with R$^q$ as defined above);

g) a sulfur containing radical: —S(O)$_n$—R$^s$ where n=0–2, and R$^s$ is defined above;

h) a sulfamoyl group: —SO$_2$N(R$^y$)R$^z$ where R$^y$ and R$^z$ are as defined above;

i) azido: N$_3$;

j) a formamido group: —N(R$^t$)(C=O)H, where R$^t$ is H or $C_{1-4}$ alkyl, and the alkyl thereof is optionally mono-substituted by R$^q$ as defined above;

k) a ($C_1$–$C_4$ alkyl)carbonylamino radical: —N(R$^t$)(C=O)$C_{1-4}$ alkyl, where R$^t$ is as defined above, and the alkyl group is also optionally mono-substituted by R$^q$ as defined above;

l) a ($C_1$–$C_4$ alkoxy)carbonylamino radical: —N(R$^t$)(C=O)O$C_{1-4}$ alkyl, where R$^t$ is as defined above, and the alkyl group is also optionally mono-substituted by R$^q$ as defined above;

m) a ureido group: —N(R$^t$)(C=O)N(R$^y$)R$^z$ where R$^t$, R$^y$ and R$^z$ are as defined above;

n) a sulfonamido group: —N(R$^t$)SO$_2$R$^s$, where R$^s$ and R$^t$ are as defined above;

o) a cyano group: —CN;

p) a formyl or acetalized formyl radical: —(C=O)H or —CH(OCH$_3$)$_2$;

q) ($C_1$–$C_4$ alkyl)carbonyl radical wherein the carbonyl is acetalized: —C(OCH$_3$)$_2$C$_{1-4}$ alkyl, where the alkyl is optionally mono-substituted by R$^q$ as defined above;

r) carbonyl radical: —(C=O)R$^s$, where R$^s$ is as defined above;

s) a hydroximinomethyl radical in which the oxygen or carbon atom is optionally substituted by a $C_1$–$C_4$ alkyl group: —(C=NOR$^z$)R$^y$ where R$^y$ and R$^z$ are as defined above, except they may not be joined together to form a ring;

t) a ($C_1$–$C_4$ alkoxy)carbonyl radical: —(C=O)O$C_{1-4}$ alkyl, where the alkyl is optionally mono-substituted by R$^q$ as defined above;

u) a carbamoyl radical: —(C=O)N(R$^y$)R$^z$ where R$^y$ and R$^z$ are as defined above;

v) an N-hydroxycarbamoyl or N($C_1$–$C_4$ alkoxy) carbamoyl radical in which the nitrogen atom may be additionally substituted by a $C_1$–$C_4$ alkyl group: —(C=O)—N(OR$^y$)R$^z$ where R$^y$ and R$^z$ are as defined above, except they may not be joined together to form a ring;

w) a thiocarbamoyl group: —(C=S)N(R$^y$)R$^z$ where R$^y$ and R$^z$ are as defined above;

x) carboxyl: —COOM$^b$, where M$^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a $C_1$–$C_4$ alkyl optionally substituted by R$^q$ as defined above;

ab) an anionic function selected from the group consisting of: phosphono: [P=O(OM$^b$)$_2$]; alkylphosphono: {P=O(OM$^b$)—[O($C_1$–$C_4$ alkyl)]}; alkylphosphinyl: [P=O(OM$^b$)—($C_1$–$C_4$ alkyl)]; phosphoramido: [P=O(OM$^b$)N(R$^y$)R$^z$ and P=O(OM$^b$)NHR$^x$]; sulfino: (SO$_2$M$^b$); sulfo: (SO$_3$M$^b$);

acylsulfonamides selected from the structures: $CONM^bSO_2R^x$, $CONM^bSO_2N(R^y)R^z$, $SO_2NM^bCON(R^y)R^z$; and $SO_2NM^bCN$, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5$-$C_7$ cycloalkyl group in which one of the carbon atoms in the ring is replaced by a heteroatom selected from O, S, NH, or $N(C_1$-$C_4$ alkyl) and in which one additional carbon may be replaced by NH or $N(C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above and phenyl which is optionally substituted by $R^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from S and $NR^t$ (where $R^t$ is as defined above) and one of the saturated carbon atoms of the oxazolidinone ring is optionally mono-substituted by one of the substituents a) to ag) above;

M is selected from:
i) hydrogen;
ii) a pharmaceutically acceptable esterifying group or removable carboxyl protecting group;
iii) an alkali metal or other pharmaceutically acceptable cation; or
iv) a negative charge which is balanced by a positively charged group.

The present invention also provides novel intermediate carbapenem compounds of the formula:

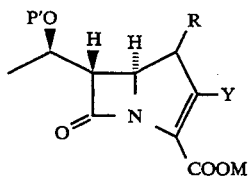

wherein:
Y is as defined above with the following exceptions:
(1) The Type II definition of $R^a$ c), $R^q$ additionally includes —OP′, where P′ is as defined below and $M^a$ and $M^b$ additionally include M, where M is as defined below;

(2) The Type II definition of $R^a$ d) additionally includes a protected hydroxy group, —OP′, where P′ is as defined below; and wherein the Type I, $R^a$ substituent is balanced with the anionic form of Z, where Z is methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo or iodo;

P′ is a removable hydroxyl protecting group such as trialkylsilyl, aryl(alkyl)alkoxysilyl, alkyldiarylsilyl, alkoxydiarylsilyl, aryldialkylsilyl, alkyloxycarbonyl, substituted alkyloxycarbonyl, benzyloxycarbonyl, substituted benzyloxycarbonyl, allyloxycarbonyl, or substituted allyloxycarbonyl;

M is a removable carboxyl protecting group such as alkyl, substituted alkyl, benzyl, substituted benzyl, aryl, substituted aryl, allyl, substituted allyl, or triorganosilyl; and all other substituents are as defined above.

Additional preferred intermediate carbapenem compounds have the following formula:

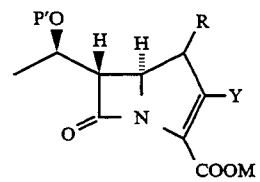

wherein:
Y is a) 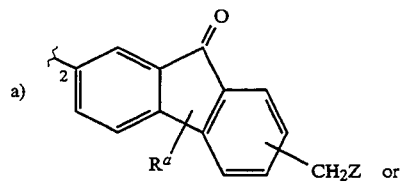

b) 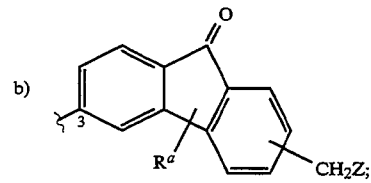

$R^a$ is selected from the group consisting of H, Br, Cl, I, CN, CHO, $CO_2M$, $CO_2CH_3$, $CONH_2$, OP′, $CH_2OP′$, $CH=N-OCH_3$, $SCH_3$, $SOCH_3$, or $SO_2CH_3$;

P′ is trimethylsilyl, triethylsilyl, t-butyldimethylsilyl, t-butoxydiphenylsilyl, t-butylmethoxyphenylsilyl, o-nitrobenzyloxycarbonyl, p-nitrobenzyloxycarbonyl, benzyloxycarbonyl, t-butyloxycarbonyl, 2,2,2-trichloroethyloxycarbonyl or allyloxycarbonyl;

M is benzhydryl, p-nitrobenzyl,2-naphthylmethyl, allyl, 2-chloroallyl, benzyl, 2,2,2-trichloroethyl, t-butyldimethylsilyl, t-butyldiphenylsilyl, 2-(trimethylsilyl)ethyl, phenacyl, p-methoxybenzyl, acetonyl, o-nitrobenzyl, p-methoxyphenyl, 4-pyridylmethyl or t-butyl;

Z is a leaving group such as alkylsulfonyloxy, substituted alkylsulfonyloxy, arylsulfonyloxy, substituted arylsulfonyloxy, fluorosulfonyloxy or halogen; and all other substituents are as defined above.

DETAILED DESCRIPTION OF THE INVENTION

The manufacture of compounds of Formula I may be carried out in a three-stage synthesis scheme followed by removal of protecting groups. The objective of the first synthesis stage is to produce a base fluoren-9-one compound which may be converted to the two-position substituent of the carbapenem of Formula I. The objective of the second synthesis stage is to attach the base fluoren-9-one to the carbapenem. Finally, the objective of the third synthesis stage is to substitute the fluoren-9-one with the desired $R^a$. This third synthesis stage may be performed during or after the first synthesis stage or after the second synthesis stage according to the nature of the various $R^a$ substituents.

Flow Sheets A, B, C and D demonstrate suggested first stage syntheses. Flow Sheets E and F demonstrate two alternative second stage syntheses. The third stage synthesis varies according to the selected $R^a$ and is demonstrated accordingly in Flow Sheets G, H, I and J.

The synthesis of the 1-, 5-, 6-, 7- or 8-substituted fluorenones are described in the schemes below (Flow Sheets A, B and C). The general route involves the preparation of a suitably substituted biphenyl which contains the 2-carboxylic acid group needed for the ring closure to generate the desired fluorenone ring system, as well as other functional groups for further elaboration to the desired fluorenone and the functionality needed for coupling to the carbapenem.

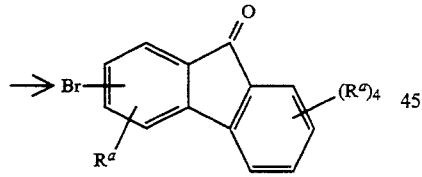

Flow Sheet D suggests a route to the preparation of a 1,7-disubstituted fluoren-9-one using similar chemistry. By altering the substitution pattern of D2 and D4 different disubstituted fluorenones can be obtained. The methyl carboxylate of D9 or D10 can be converted to a hydroxymethyl, aldehyde, carboxyamide or nitrile substituent.

FLOW SHEET A

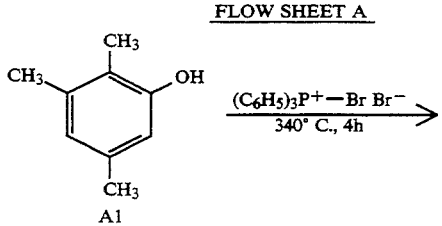

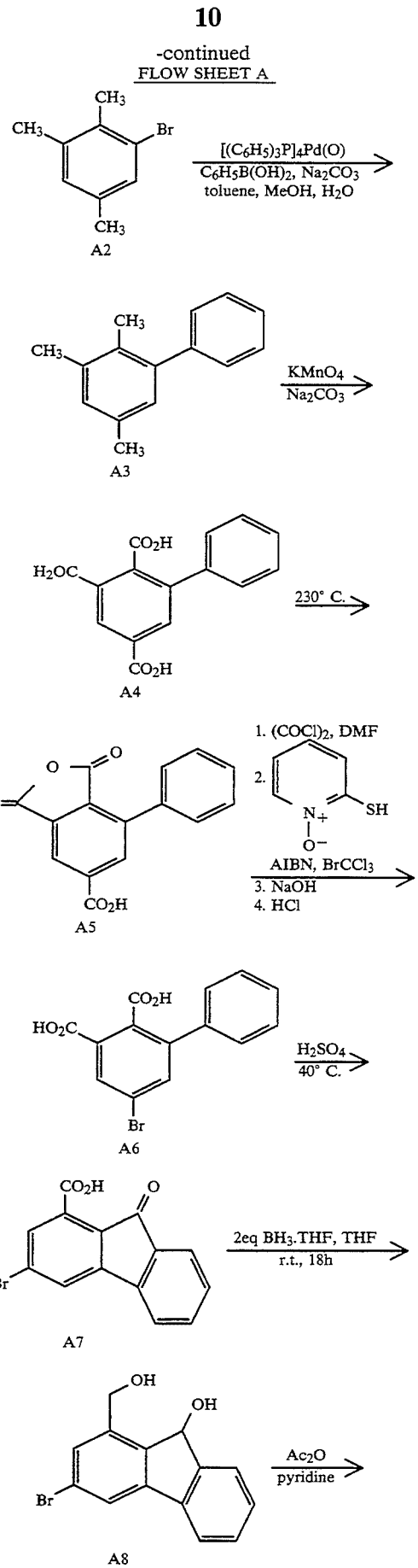

-continued
FLOW SHEET A
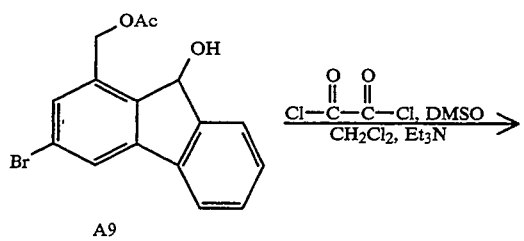
-continued
FLOW SHEET B
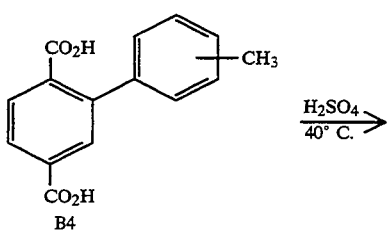
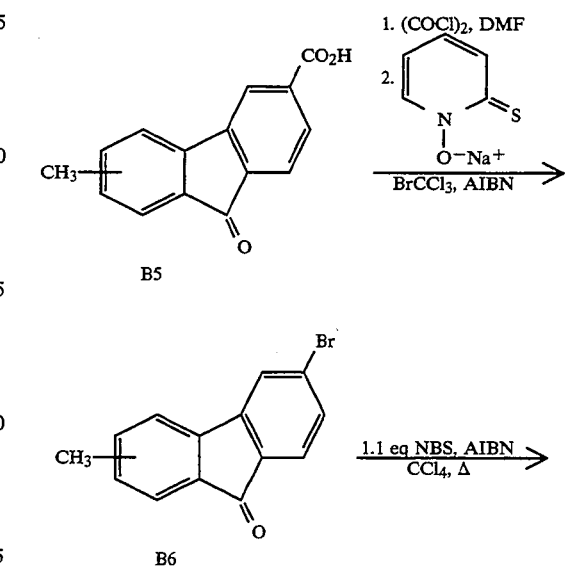
FLOW SHEET B
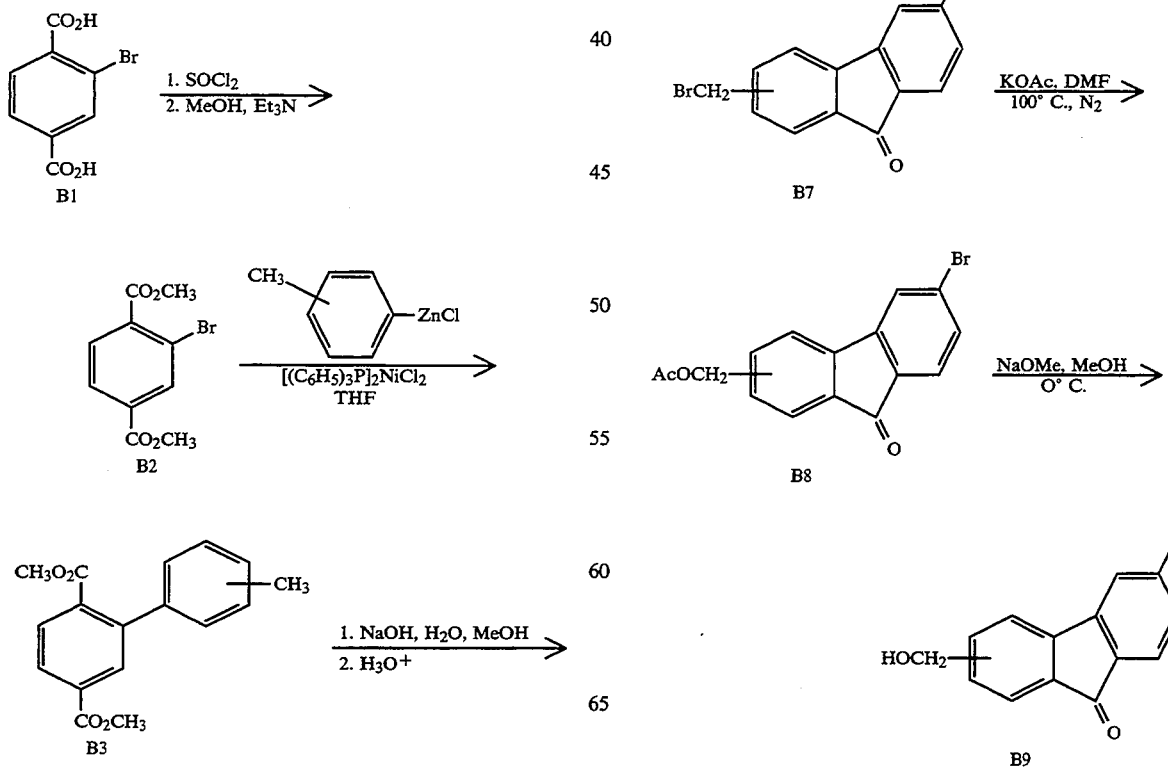

5,356,889
FLOW SHEET C
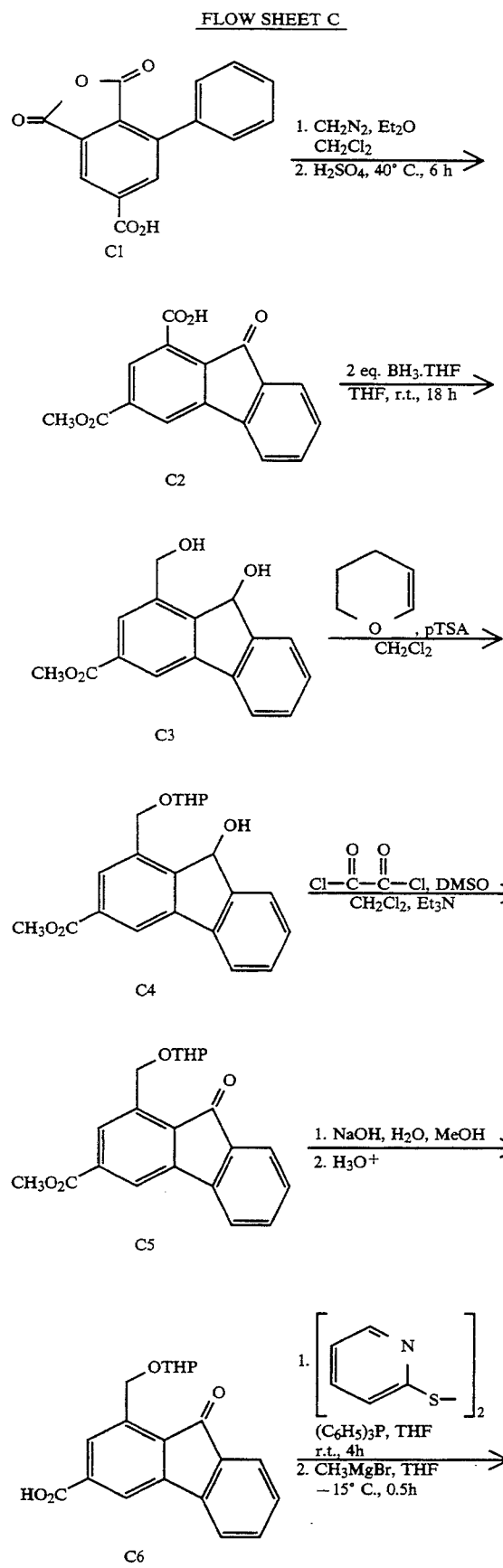
-continued
FLOW SHEET C
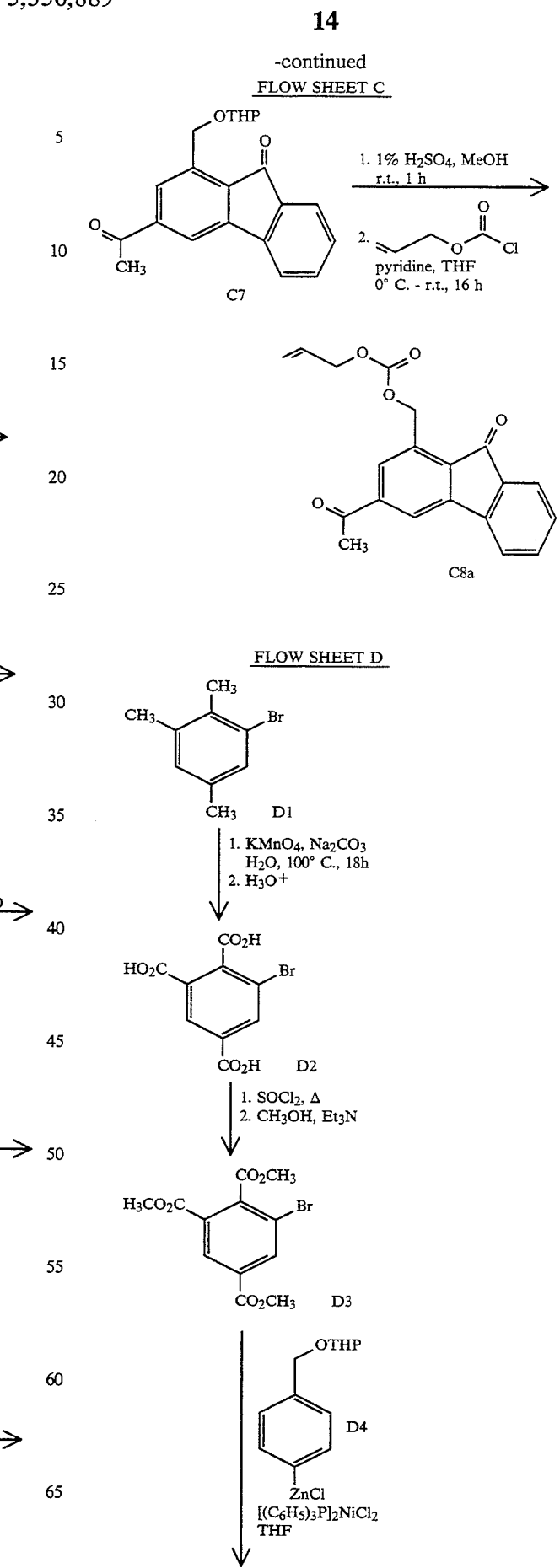

-continued
FLOW SHEET D

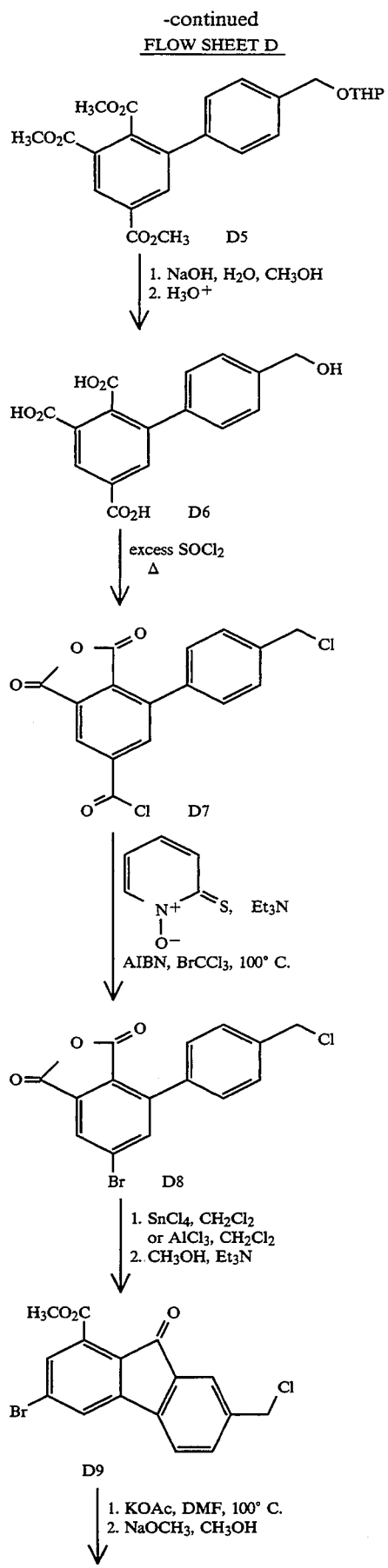

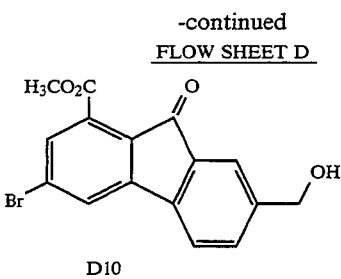

The desired fluorenone, produced in the first synthetic stage, is attached to the carbapenem in the second stage using one of two possible routes:

1) coupling to an acetoxyazetidinone intermediate followed by Wittig cyclization to the carbapenem; or
2) direct coupling to a carbapenem triflate. Flow Sheet E describes the first method and Flow Sheet F describes the direct coupling to the carbapenem.

Referring to Flow Sheet E, the silyl enol ether of an appropriately substituted 3-acetyl-fluoren-9-one such as C8 is coupled to the known azetidinone E1 [P. J. Reider and E. J. Grabowski, *Tetrahedron Letters*, 23, 2293 (1982); K. Hirai, Y. Iwano, and K. Fujimoto, *Heterocycles*, 17, 201 (1982)] using Lewis acid catalysis to give the azetidinone intermediate E2. The azetidinone, E2, can be cyclized to a carbapenem, according to Route B, by acylation of the azetidinone nitrogen with allyl oxalyl chloride and reaction of the resulting oxalimide with triethylphosphite to give a ylide intermediate which on heating in xylene at 90° to 140° C. with or without a small amount of hydroquinone, from 1 to 4 hours, gives the carbapenem E3. Alternatively, cyclization can be carried out according to Route A by condensation of E2 with allyl glyoxylate, chlorination of the resulting hemiaminal with thionyl chloride—2,6-lutidine, reaction with triphenylphosphine followed by sodium bicarbonate and finally cyclization of the ylide intermediate thus produced by heating in xylene at 90° to 140° C. for 1 to 4 hours to give carbapenem E3. It is on an intermediate like E3 that final elaboration of the substituent $R^a$ from a precursor substituent such as hydroxymethyl may be accomplished, if necessary. Removal of the protecting groups then provides the final compound of Formula I. Such final elaboration and deprotection is described in further detail below.

Use of the isomeric 2-methylcarbonyl C8 in Flow Sheet E provides the corresponding 2-fluorenone derivative of the carbapenem E3, where attachment of the carbapenem is at the 2-position of the fluorenone. The isomeric 2-methylcarbonyl C8 is obtained by the use of the appropriately substituted biphenyl in the steps outlined in Flow Sheets A, B and C.

FLOW SHEET E
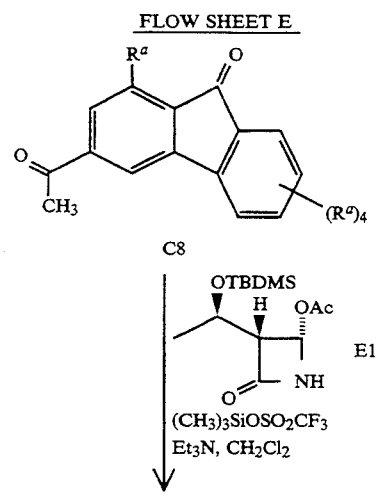
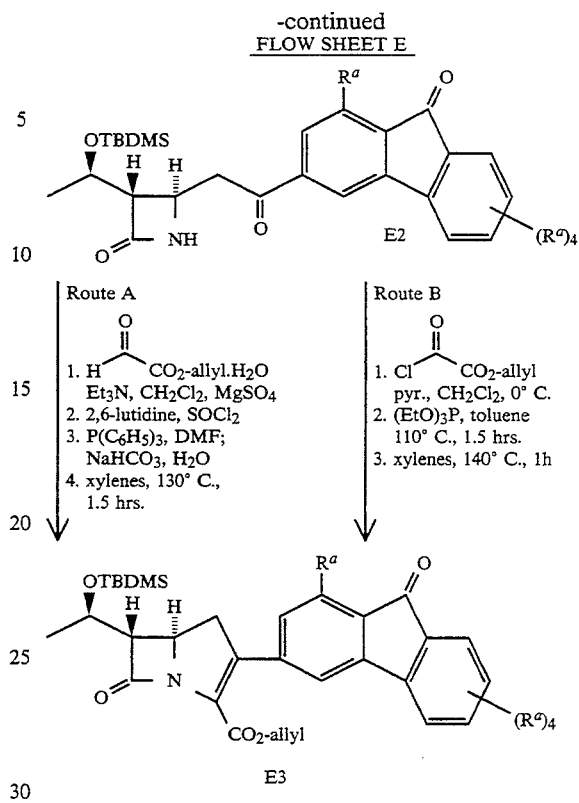
FLOW SHEET F
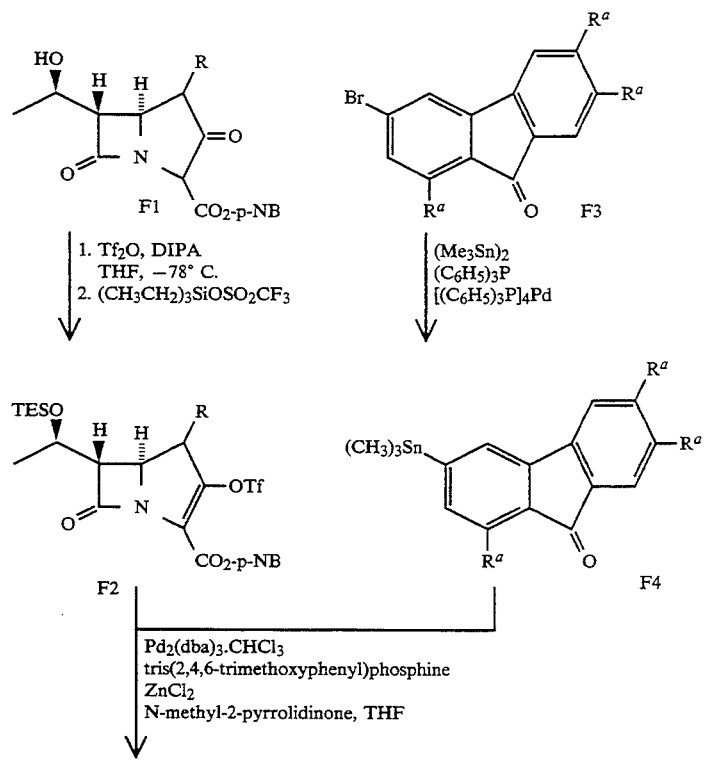

FLOW SHEET F

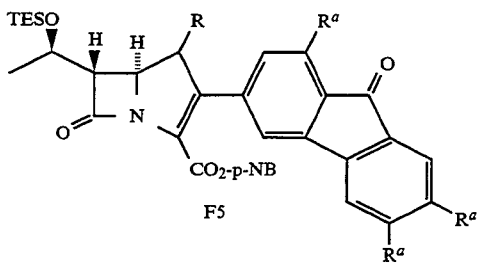

p-NB = para-nitrobenzyl

Flow Sheet F shows an alternative second stage synthesis, i.e. attachment of the base fluorenone to the 2-position of the carbapenem. This synthesis involves a palladium catalyzed cross-coupling reaction between a carbapenem triflate and a suitably substituted arylstannane, a process which is described in U.S. patent application Ser. No. 485,096 filed Feb. 26, 1990. In order to apply this synthesis, it is first necessary to modify the bromofluoren-9-one (e.g. F3) to the trimethylstannyl-fluoren-9-one (e.g. F4). This is accomplished by reacting the bromo compound, hexamethylditin, tetrakis(triphenylphosphine)palladium(0) and triphenylphosphine in toluene at 110° C. Referring to Flow Sheet F, the 2-oxocarbapenam F1 is reacted with a suitable trifluoromethanesulfonyl source, such as trifluoromethanesulfonic anhydride, trifluoromethanesulfonyl chloride and the like, in the presence of an organic nitrogen base, such as triethylamine, diisopropylamine and the like, in a polar aprotic solvent, such as tetrahydrofuran. An organic nitrogen base, such as triethylamine and the like, is then added to the reaction solution followed immediately by a silylating agent, such as trimethylsilyl or triethylsilyl trifluoromethanesulfonate to provide the triflate intermediate F2. An aprotic polar coordinating solvent, such as DMF, 1-methyl-2-pyrrolidinone and the like, is added. This is followed by the addition of a palladium compound, such as tris(dibenzylideneacetone)dipalladiumchloroform, palladium acetate and the like, optionally a suitably substituted phenylphosphine, such as tris(4-methoxyphenyl)phosphine, tris(2,4,6-trimethoxyphenyl)phosphine and the like, and the stannane F4. A metal halide, such as lithium chloride, zinc chloride and the like, is added and the reaction solution is warmed to a suitable temperature, such as 0° C. to 50° C., and allowed to stir for a suitable amount of time such as from a few minutes to 48 hours. The carbapenem F5 is obtained by conventional isolation/purification methodology known in the art.

The corresponding 2-fluoren-9-one regioisomer of F5 can be prepared analogously by starting with the 2-bromofluoren-9-one corresponding to F3, which in turn is derived from appropriately substituted biphenyls by following the steps outlined in Flow Sheets A, B, and C.

Generally speaking, the milder conditions of the synthesis shown in Flow Sheet F allow for a wider range of functional groups $R^a$ to be present when attaching the fluoren-9-one, than the synthesis illustrated in Flow Sheet E. However, in certain cases it is advantageous for the $R^a$ substituent(s) of the stannane F4 to be introduced in a protected or precursory form. Final elaboration of $R^a$ from a precursor substituent, e.g. hydroxymethyl, may be accomplished on carbapenem intermediate F5. Removal of protecting groups then provides the final compound of Formula I.

Azetidin-2-one, E1 is a well known compound in the production of carbapenems. Diverse synthetic schemes useful to make E1 may be imagined by the skilled artisan. The steps for preparing this intermediate are analogous to the procedures described in P. J. Reider and E. J. Grabowski, Tetrahedron Letters, 23, 2293 (1982) and K. Hirai, Y. Iwano and K. Fujimoto, Heterocycles, 17, 201 (1982).

The steps for preparing the 2-oxocarbapenam intermediate, F1, are well known in the art and are explained in ample detail by D. G. Melillo, et al., Tetrahedron Letters, 21, 2783 (1980), T. Salzmann et al., J. Am. Chem. Soc., 102, 6161 (1980), and L. M. Fuentes, I. Shinkai, and T. N. Salzmann, J. Am. Chem. Soc., 108, 4675 (1986). The syntheses are also disclosed in U.S. Pat. Nos. 4,269,772, 4,350,631, 4,383,946 and 4,414,155 all assigned to Merck and Co., Inc.

Final elaboration of $R^a$ from a precursor substituent, e.g. hydroxymethyl, may be accomplished on the carbapenem intermediate F5. Flow Sheets G, H, I and J show representative procedures. Flow Sheet G describes a one step process for introducing the Type Ia cationic substituent and utilizes 2.5 equivalents of a nucleophilic nitrogen base to generate the triflate and undergo nucleophilic substitution. An alternate procedure illustrated in Flow Sheet H describes a two step process utilizing a non-nucleophilic base and triflic anhydride to generate the triflate, H1, followed by treatment with a nucleophilic nitrogen base, to affect nucleophilic substitution. Flow Sheets I and J show suggested syntheses for introducing Type Ib cationic substituents. Further discussion of the elaboration of $R^a$ from a precursor substituent such as hydroxymethyl and removal of protecting groups to give the final compounds of Formula I appears further below.

FLOW SHEET G
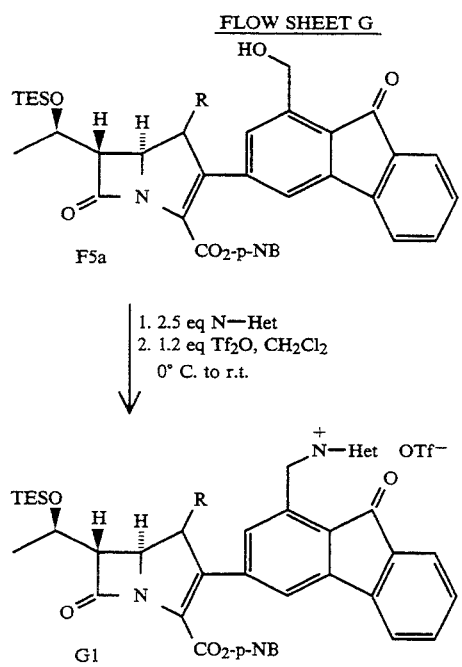
FLOW SHEET H
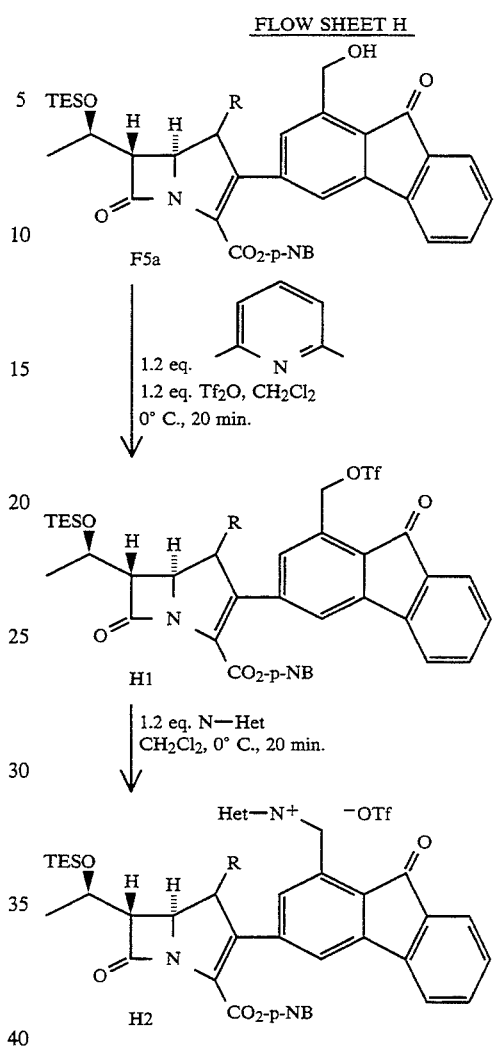
The preferred route for strong, nucleophilic bases. For example where N-Het is
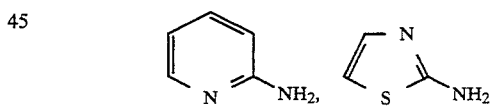
FLOW SHEET I
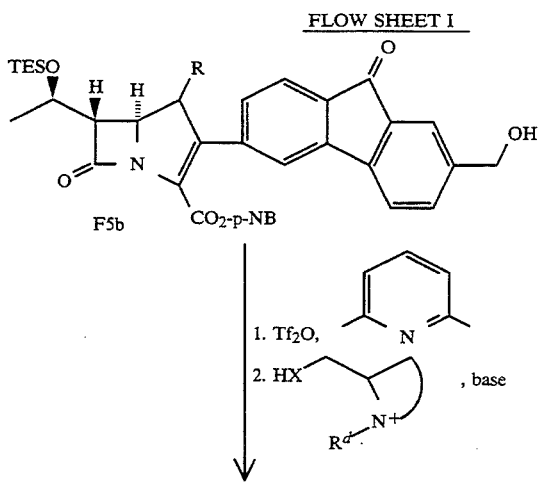

FLOW SHEET I
-continued
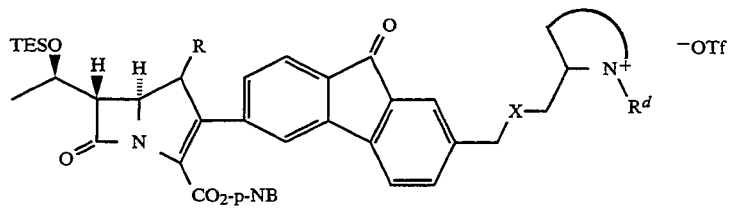
I1
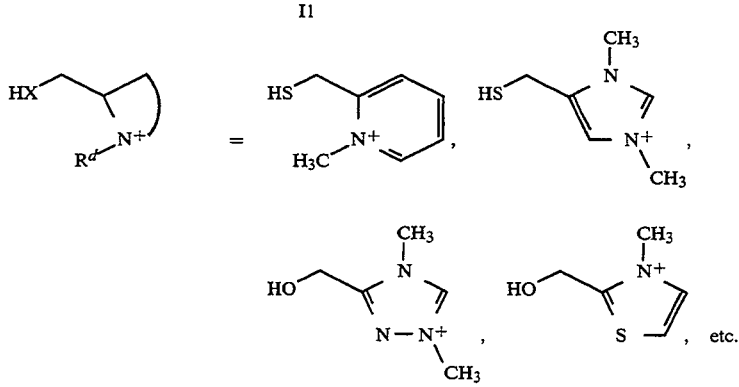
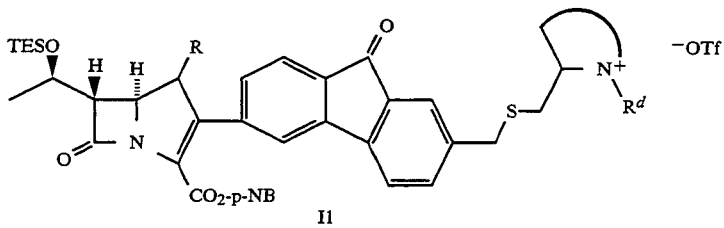
I1
↓ mCPBA, H₂O, CH₂Cl₂, NaHCO₃
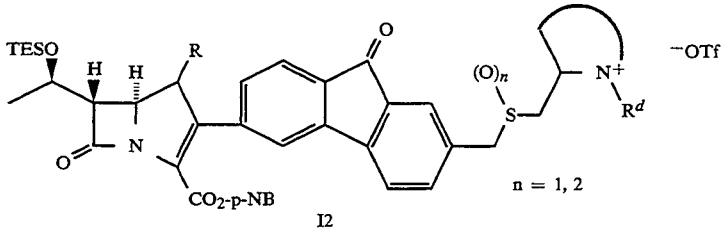
n = 1, 2
I2
FLOW SHEET J
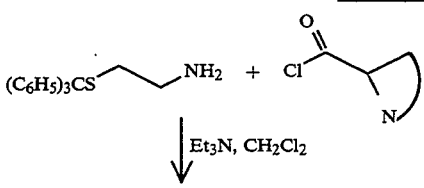
↓ Et₃N, CH₂Cl₂
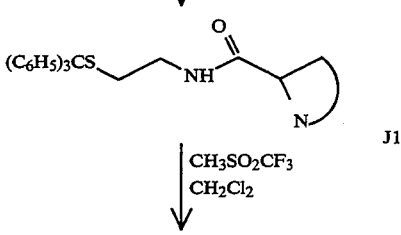
J1
↓ CH₃SO₂CF₃
   CH₂Cl₂

FLOW SHEET J -continued

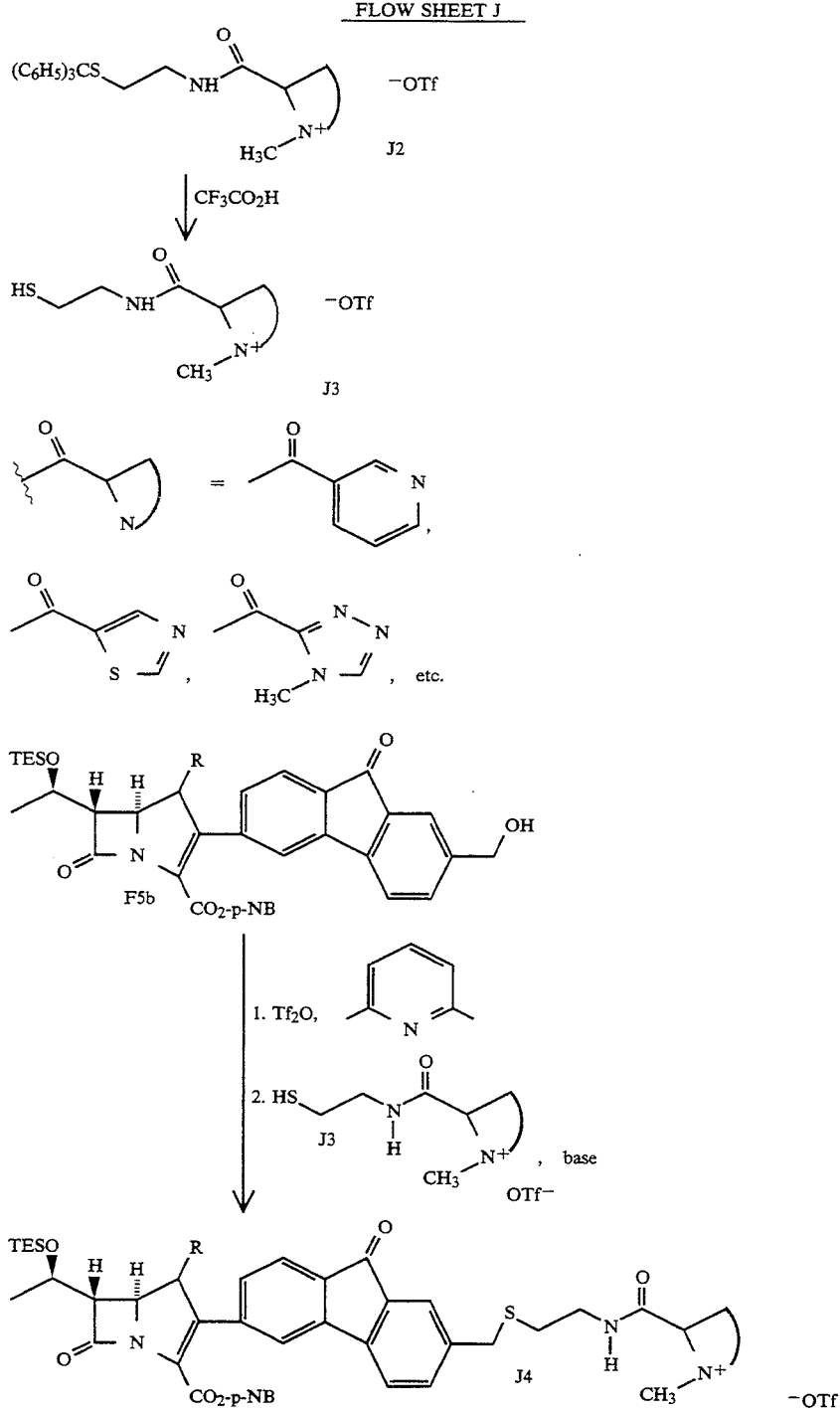

The general synthesis description depicted above in the Flow Sheets shows a protected 1-hydroxyethyl substitution on the 6-position of the carbapenem. After final deprotection, a 1-hydroxyethyl substituent is obtained, which is preferred in most cases. However, it has been found that with certain 2-side-chain selections, the ultimate balance of favorable properties in the overall molecule may be enhanced by selection of the 6-(2-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. de-Vries et al., Heterocycles, 23 (8), 1915 (1985); BE 900 718 A (Sandoz) and Japanese Patent Pub. No. 6-0163-882-A (Sanraku Ocean).

In the compounds of the present invention, one of the $R^a$ substituents must be of Type I. As a general matter, it is conjectured that anti-MSRA/MRCNS activity results from the configuration of the overall molecule uniquely conferred by the fluorenone nucleus. The Type I substituent provides still greater anti-MRSA/MRCNS activity to the molecule. Flow Sheets G, H, I and J describe suggested methods of generating some of the desired Type I R$^a$ substituents.

The Type II R$^a$ substituents are distinguishable from Type I R$^a$ substituents chemically and with respect to the biological properties which they confer. In related compounds, it has been found that the Type II substituted compounds afford greater water solubility and reduced potential for CNS side effects. Substituents which tend to confer improved water solubility on the overall compound have been found useful, since they are contemplated to thereby improve the transport of the compound involved. Although a substantial number and range of Type II substituents have been described herein, all of these are contemplated to be a part of the present invention based on the biological performance of substituents related in terms of their medicinal chemistry.

Since it is possible to combine, in the compounds of the present invention, the required Type I R$^a$ substituent with the optional Type II R$^a$ substituents, there can be obtained a combination of desired attributes in the final overall molecule not attainable with a single substituent, i.e., improved anti-MRSA/MRCNS activity together with enhanced water solubility.

The Type I R$^a$ substituents employed in the compounds of the present invention may have quaternary nitrogen groups, and these include both cyclic and acylic types, as is described under I. As already pointed out above, it is required that one, but no more than one, of the substituents R$^a$ must be a member selected from the group consisting of the definitions under Type I. It is optional that one, or at most three, of the remaining substituents may be a member selected from the group consisting of definitions under Type II. For example, R$^a$ at position 7- may be Type I and R$^a$ at position 1- may be of Type II, while the remaining substituents are hydrogen.

In preferred compounds of Formula I, R$^1$ is hydrogen. More preferably, R$^1$ is hydrogen and R$^2$ is (R)—CH$_3$CH(OH)— or (R)—CH$_3$CH(F)—. In the most preferred case, R$^1$ is hydrogen and R$^2$ is (R)—CH$_3$CH(OH)—. While R=H is usually preferred, there are instances in which R=CH$_3$ may provide improved chemical stability, water solubility, or pharmacokinetic behavior. The substituent R=CH$_3$ may be of either configuration, i.e., the α or β-stereoisomer. Additionally, in preferred compounds of Formula I, in total, up to two R$^a$ substituents in either the 1-, 6-, 7- or 8-positions of the 3-fluoren-9-one or the 4-, 6- or 7-positions of the 2-fluoren-9-one are other than hydrogen. More preferably, Y is b, the 3-fluoren-9-onyl substituent.

Preferred Type Ia substituents include:

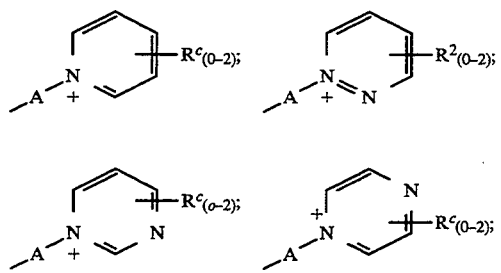

-continued

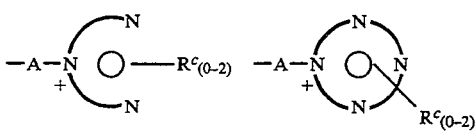

where the ring contains three carbon atoms;   where the ring contains two carbon atoms;

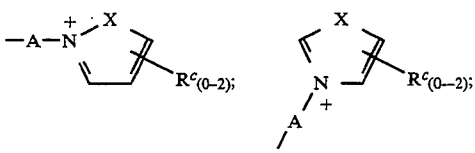

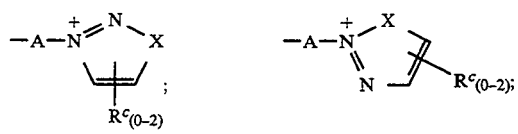

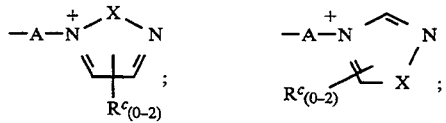

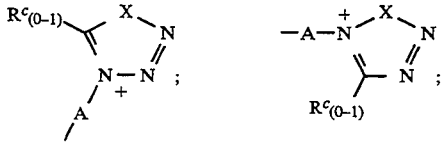

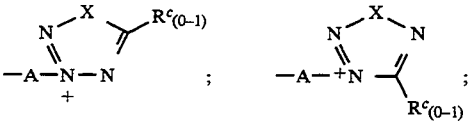

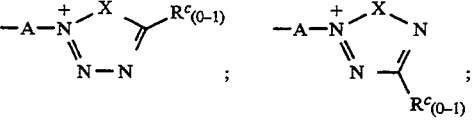

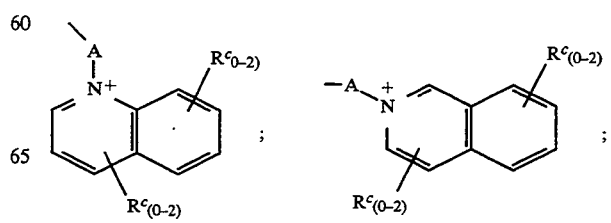

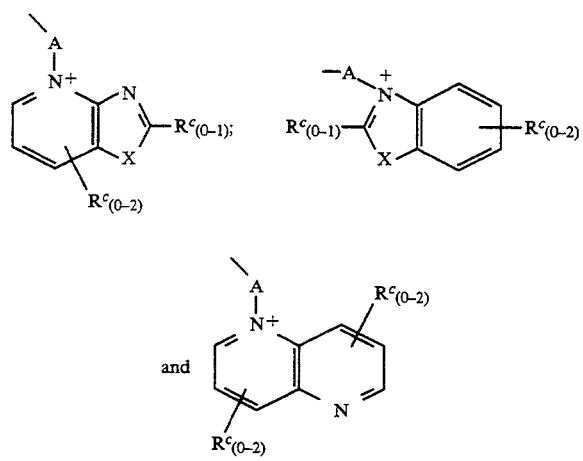

where X=O, S, or NR$^c$. For structures of Type Ia, where R$^c$ is shown to have an indefinite position, it is attached to any carbon of the ring.

Preferred Type Ib substituents include:

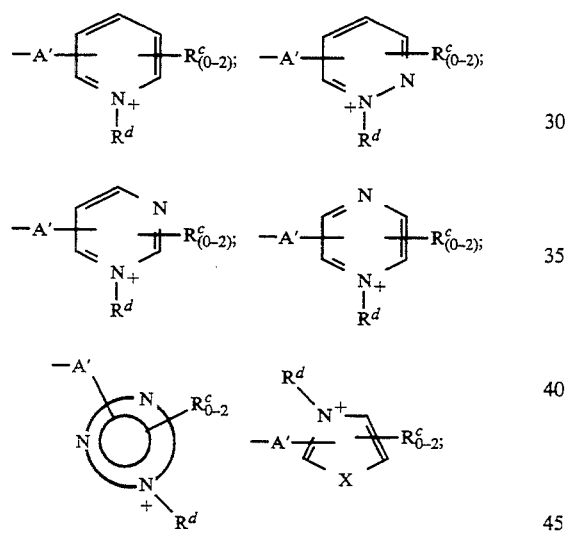

where the ring contains three carbon atoms;

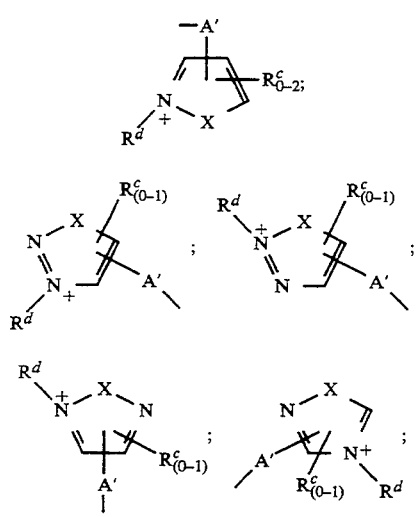

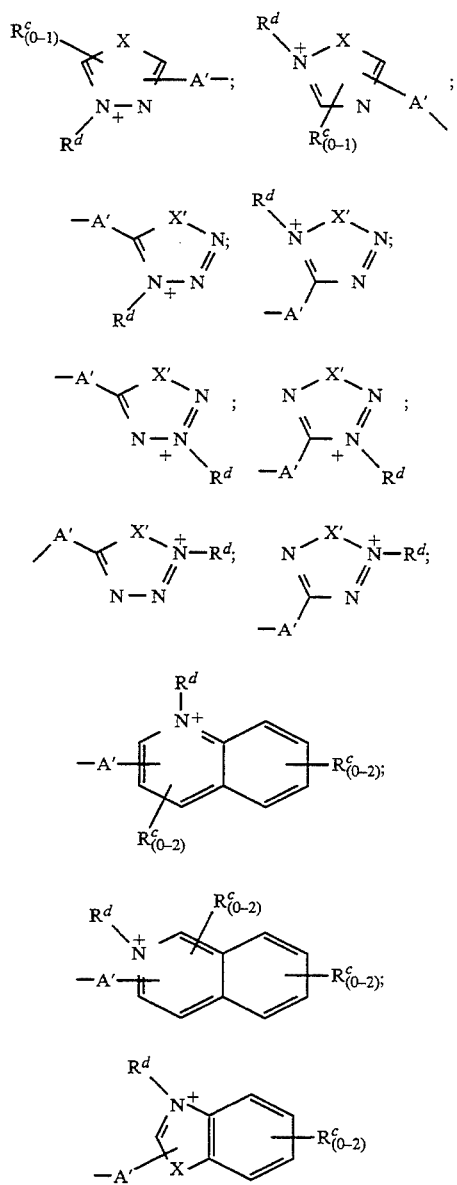

where X=O, S, or NR$^c$ and X'=O or S. For structures of Type Ib, where R$^c$ and/or A' are shown to have indefinite positions, they are independently attached to any carbon atom of the ring.

Preferred Type Ic substituents include:

—Ap—$^+$N(CH$_3$)$_3$,  —Ap—$^+$N(CH$_2$CH$_3$)$_3$,

—Ap—$^+$N(CH$_3$)$_2$CH$_2$R$^q$   —Ap—$^+$N(CH$_2$CH$_3$)$_2$CH$_2$CH$_2$R$^q$,

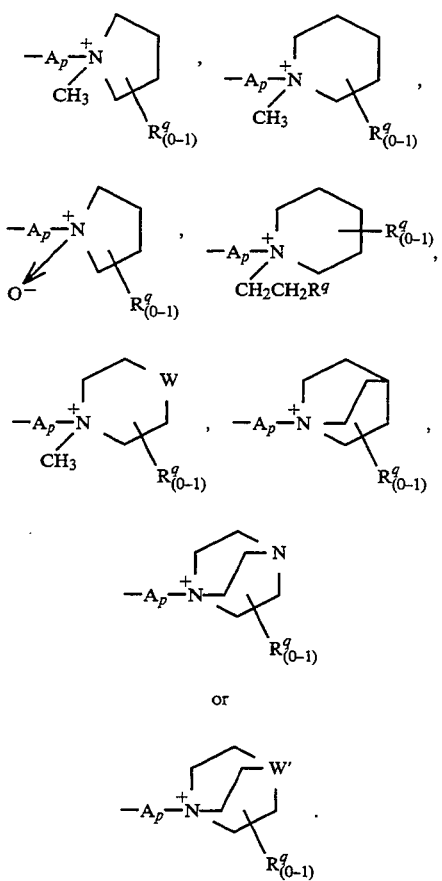

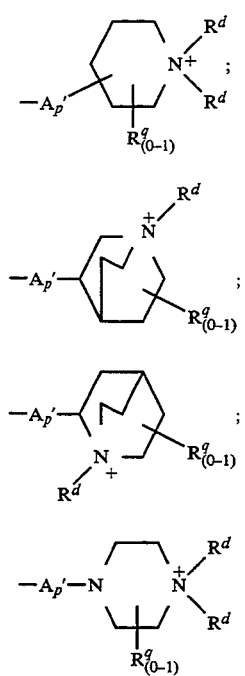

where W is O, S, NR$^e$, N(O)R$^e$, SO, SO$_2$ or N$^+$(R$^e$)$_2$ and W' is N$^+$R$^e$ or NO. For structures of Type Ic, where R$^q$ is shown to have an indefinite position, it may be attached to any carbon atom of the ring.

Preferred Type Id substitutents include:

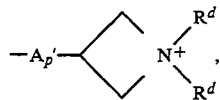

For structures of Type Id where R$^q$ and/or A'$_p$ is shown to have an indefinite position, it may be attached to any carbon atom of the ring.

The R$^c$ substituents herein are intended to represent suitable further substitutents on the Type Ia or Ib substitutents for the fluorenonyl ring. As seen above, these Type Ia or Ib substitutents are monocyclic or bicyclic aromatic groups containing heteroatoms. Given this class primary substituent, further suitable substituents may be readily discovered in the carbapenem art. For example, suitable substituents for Type Ia or Ib substituents are generally taught in U.S. Pat. No. 4,729,993 assigned to Merck and Co. or in U.S. Pat. No. 4,746,736 assigned to Bristol-Myers Co.

Broadly, R$^c$ may be the same or different and may be selected on an independent basis from the group as defined above. While a single such substitution is preferred, there is occasion to use up to two such substituents on an R$^a$, e.g., where it is desired to enhance the effect of a particular substituent group by employing multiple substituents. The particular choice of R$^c$ will depend upon the situation. For instance, a specific R$^c$ may lend particular stability to a nitrogen cation. At other times it may be desired to employ a substituent known to enhance antibacterial activity of the overall molecule against a particular bacterium, for example, while also employing a substituent known to improve some other property such as water solubility or the duration of action of the overall molecule.

The scope of R$^c$ herein includes two specific types of further substitutent attached to the Type Ia or Ib substitutent. A first type of R$^c$ are those attached to a ring carbon and a second type of R$^c$ are those attached to a neutral ring nitrogen. Persons skilled in the art will readily recognize that a wide range of organic substituents are suitably used as R$^c$. Persons skilled in the art will also recognize that some substituents including the —NR$^y$R$^z$ substituents, useful for one purpose of R$^c$, i.e. carbon substitution, are not equally useful in the other, i.e. nitrogen substitution Preferred R$^c$ attached to ring carbon atoms are —NH$_2$, —SCH$_3$, —SOCH$_3$, —CH$_2$OH, —(CH$_2$)$_2$OH, —OCH$_3$, —COOM$^b$, —CH$_2$COOM$^b$, —CH$_2$CH$_2$COOM$^b$, —CH$_2$SOCH$_3$, —CH$_2$SCH$_3$, —SO$_3$M$^b$, —CH$_2$SO$_3$M$^b$, —CH$_2$CH$_2$SO$_3$M$^b$, —Br, —Cl, —F, —I, —CH$_3$, CH$_2$CH$_3$, CH$_2$CONH$_2$ and CH$_2$CON(C$_1$-C$_4$alkyl)$_2$ where M$^b$ is defined above. Preferred R$^c$ attached to neutral ring nitrogen atoms are —CH$_2$OH, —(CH$_2$)$_2$OH, —CH$_2$COOM$^b$, —CH$_2$CH$_2$COOM$^b$, —CH$_2$SOCH$_3$, —CH$_2$SCH$_3$, —CH$_2$SO$_3$M$^b$, —CH$_2$CH$_2$SO$_3$M$^b$, —CH$_3$, CH$_2$CH$_3$, CH$_2$CONH$_2$ and CH$_2$CON(C$_1$-C$_4$alkyl)$_2$ where M$^b$ is defined above.

It is preferred that each Type Ia or Ib substituent have no more that two R$^c$ substituents which are other than hydrogen. Thus, the formula shown above for Type Ia substitutents has up two R$^c$ substituents with the remainder of course being hydrogen. Further, the formula for the Type Ib substitutents also allows up to two R$^c$. In accordance with these formulae, the previously listed more specific structures should be interpreted to have no more than two $R^c$ for each monocyclic or bicyclic group. Similarly for Type Ic or Id substituents it is preferred that any monocyclic or bicyclic group have no more than a single $R^q$ substituent.

The scope of $R^d$ includes a single type of further substituents attached to a Type Ib or Id substituent. The $R^d$ substituents are attached to a cationic nitrogen which may or may not be aromatic. Preferred $R^d$ attached to cationic nitrogen atoms are hydrogen, —CH$_3$, —CH$_2$CH$_3$, —CH$_2$CH$_2$CH$_3$, —CH$_2$COOM$^b$, —CH$_2$SO$_3$M$^b$, —NH$_2$ and O$^{(-)}$, where M$^b$ is defined above.

The formulas depicting Type Ib, Ic, and Id substituents show positively charged states for those substituents. It is understood that certain of those substituents, which are cationic by virtue of having a protonating hydrogen atom attached to the nitrogen, may also exist or be produced under certain conditions as a neutral substituent by virtue of the absence of such a hydrogen atom (i.e. in Type Ib, when there is no $R^d$; in Type Ic, when there is no $R^w$; and in Type Id, when there is zero to one $R^d$, depending on type of heterocycle). Whether such a Type Ib, Ic, or Id substituent will be predominately cationic or neutral in a given physical state will be governed by principles of acid-base chemistry, which are well known to those skilled in the art. For example, the particular ratio of neutral form to cationic form will depend upon the basicity of the amine and acidity of a solution. When such a substituent is in a protonated quaternized state, the compound exists as a zwitterion which is internally balanced as to charge or as an ammonium salt which is externally balanced. In illustration, if there is no $R^d$ on a Type Ib substituent, it is understood that such a substituent is neutral (there is no positive charge on the nitrogen). A compound containing such a substituent is typically produced in this form as a salt, wherein M is an alkali metal, and may exist in solution in its neutral form. However, depending upon conditions, a compound containing a neutral Type Ib substituent may be in equilibrium with, and may also be represented by a formula showing, the corresponding compound containing the quaternized protonated substituent where $R^d$ is present and is a hydrogen atom. Furthermore the same compound may exist with the group Ib substituent in a completely protonated quaternized form, for instance in an aqueous solution in the presence of a stoichiometric amount of a strong mineral acid. It is intended herein that both the protonated (cationic) and the unprotonated (neutral) forms of Types Ib, Ic and Id substituents of the kinds just described are within the scope of the present invention.

Suitable A spacer moieties include —CH$_2$—, —CH$_2$—CH$_2$—, —CH$_2$—CH$_2$—CH$_2$—, —CH$_2$—CH$_2$—CH$_2$—CH$_2$—, —OCH$_2$CH$_2$—, —SOCH$_2$—, —SO$_2$CH$_2$—, —SCH$_2$CH$_2$—, —SOCH$_2$CH$_2$—, —SO$_2$CH$_2$CH$_2$—, —NHCH$_2$CH$_2$—, —N(CH$_3$)CH$_2$CH$_2$—, CH$_2$N(CH$_3$)CH$_2$CH$_2$—, —CONHCH$_2$CH$_2$—, —SO$_2$NHCH$_2$CH$_2$—, —COCH$_2$—, —CH=CHCH$_2$— and —CH$_2$OCH$_2$CH$_2$—. Preferably, where Q is O, S, NH or N(C$_{1-4}$alkyl), then n is 2–6.

Suitable A' are listed for A above. Further A' may suitable be —O—, —S—, —NH—, —SO$_2$—, —SO$_2$NH—, —CONH—, —CH=CH—, —CH$_2$S—, —CH$_2$NH—, —CONHCH$_2$— or —SO$_2$NHCH$_2$—.

The Type I cationic substituents are generally added to the fluoren-9-one following attachment of the fluoren-9-one to the carbapenem. Conveniently, the fluoren-9-one side-chain should be synthesized with a precursor substituent which may be elaborated into the desired cationic substituent. The identity of the precursor substituent will vary according to the particular $R^a$ desired. For example, one such precursor substituent is —A—OH, such as hydroxymethyl.

The hydroxymethyl precursor substituent may be elaborated into cationic substituents of Type Ia by converting the hydroxyl into an active leaving group, Z, such as an iodide (giving —A—I) followed by reaction with a desired nitrogen containing aromatic compound. More particularly, two alternative procedures may be utilized to produce a leaving group on the moiety —A— and subsequently to replace such a leaving group with cationic substituents of the type just described.

For the first procedure, the hydroxyl group of —A—OH may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate, which itself is a good leaving group, may be converted to the reactive iodide derivative by treatment with sodium iodide in a suitable solvent, e.g., acetone, at reduced or ambient temperatures. Alternatively, the hydroxyl group may be directly converted into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. Once the iodide has been formed, the introduction of the cationic substituent is accomplished simply by treating the iodide with the desired nitrogen containing compound, e.g. a heteroaromatic compound such as pyridine. The reaction will proceed in a suitable solvent, such as acetonitrile, at or about room temperature. This displacement reaction may also be facilitated by the addition of excess silver trifluoromethanesulfonate to the reaction mixture, in which case reduced temperatures are often desirable.

For a second procedure, the hydroxyl group of —A—OH may be converted into the reactive trifluoromethanesulfonate (triflate) group. However, such an activating group cannot be isolated by conventional techniques but may be formed and used in situ. Thus, treatment of the hydroxyl group with a slight excess of trifluoromethanesulfonic (trific) anhydride in the presence of a hindered, non-nucleophilic base such as 2,6-lutidine, 2,4,6-collidine, or 2,6-di-tert-butyl-4-methylpyridine in a suitable solvent, such as dichloromethane, at reduced temperatures provides for the generation of the triflate activating group. The fluorosulfonate group can be prepared in an analogous manner. Introduction of the cationic group is then accomplished by reacting the above triflate in situ with the desired nitrogen containing compound at reduced temperature. In certain cases it is possible and desirable to use the reacting nitrogen containing compound as the base for the formation of the triflate activating group. In this case treatment of the hydroxyl group with triflic anhydride in the presence of at least two equivalents of the reacting nitrogen compound under the conditions described above provides the cationic substituent.

The above are representative of suitable leaving groups such as: alkyl and substituted alkylsulfonates, aryl and substituted arylsulfonates, and halides. The common sulfonate leaving groups are: methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy and p-nitrobenzenesulfonyloxy. The preferred halo leaving groups are bromo and iodo. These alkyl and arylsulfonate leaving groups may be prepared using an analogous route to the one described above using the sulfonyl chloride or the sulfonic anhydride. The preferred halo leaving groups are bromo and iodo.

Where the cationic substitution has a substituent $R^c$, the most facile method of providing such a substituent is to employ as the reactant in the preparation methods described above a nitrogen containing compound which already has the desired substituent. Such substituted compounds are readily available starting materials or may be prepared in a straight-forward manner using known literature methods.

The Type Ib cationic substituents may prepared by quaternization of an aromatic ring nitrogen of a neutral precursor substituent on the fluoren-9-one ring. Examples of neutral precursor substituents are —CONHCH$_2$—(2-pyridyl), —CONHCH$_2$—(4-pyridyl) or —SO$_2$CH$_2$—(4-pyridyl). Quaternization is accomplished by reacting the nitrogen compound in an inert organic solvent (e.g. CH$_2$Cl$_2$) at about 0° C. to room temperature with an alkylating agent $R^d$—G where $R^d$ is given above and G is a leaving group such as iodide, bromide, mesylate (methanesulfonate), tosylate (p-toluenesulfonate) or triflate (trifluoromethanesulfonate). Alternatively, the aromatic ring nitrogen may be quaternized by reaction with an oxidizing agent such as 3-chloroperbenzoic acid (giving the N-oxide) or an amidinating reagent such as O-(2,4,6-triisopropylbenzenesulfonyl)hydroxylamine (giving the N-amino derivative) in a suitable solvent (e.g. CH$_2$Cl$_2$ or CH$_3$CN) at about room temperature. In addition, the neutral precursor substituent may be rendered cationic through protonation of the basic aromatic ring nitrogen. This may be accomplished by treatment of the neutral precursor with a suitable inorganic or organic acid, e.g. hydrochloric acid, phosphoric acid, hydrobromic acid, acetic acid or benzoic acid. Protonation may further be accomplished by a carboxylic acid function elsewhere in the molecule, including the C-3 carboxyl on the carbapenem. The neutral precursor substituent may be already attached to the fluoren-9-one ring at the time of its connection to the carbapenem, or it may be elaborated from a simpler precursor after connection to the carbapenem. An example of a precursor substituent for elaboration is —A'—OH such as hydroxymethyl. In one suggested synthesis, the hydroxyl may be converted to a reactive leaving group such as iodo as described above. The iodide is then reacted in a nucleophilic displacement reaction with a nitrogen containing aromatic compound which has a nucleophilic side-chain substituent such as CH$_2$SH or CH$_2$NH$_2$. In this displacement reaction, it is the side-chain substituent that is the reacting nucleophile and not the aromatic ring nitrogen. Suitable substrates for this reaction include 2-(mercaptomethyl)pyridine, 2-aminopyridine, 2-(aminomethyl)pyridine or 4-(mercaptomethyl)pyridine. The reaction is carried-out in an inert organic solvent, e.g. methylene chloride, at from about 0° C. to room temperature in the presence of a non-nucleophilic base such as triethylamine or diisopropylethylamine. Quaternization or protonation as described above then gives the Type Ib cationic substituent. A second suggested synthesis of a Type Ib cationic substituent starting from a precursor A'—OH (e.g. hydroxymethyl) consists of oxidation of the alcohol functionally to an aldehyde followed by Wittig-type olefination with an appropriate nitrogen-containing aromatic substituted reagent, and finally quaternization. The oxidation may be conveniently accomplished by a Swern oxidation employing oxalyl chloride-dimethylsulfoxide followed by triethylamine. The reaction is conducted in methylene chloride as a solvent at from $-70°$ C. to 0° C. The Wittig reaction is carried-out by reacting the aldehyde with the desired Wittig reagent in a polar solvent such as acetonitrile or dimethylsulfoxide at about room temperature. Suitable Wittig reagents include: pyridylmethylenetriphenylphosphorane, quinolylmethylenetriphenylphosphorane and thiazolylmethylenetriphenylphosphorane. Quaternization or protonation as described above then completes the synthesis of the Type Ib cationic substituent. Depending on the particular $R^a$ of Type Ib that is desired, many other synthesis schemes may be employed, as would be apparent to an organic chemist skilled in the art.

The Type Ic cationic substituents may be prepared in an analogous manner to that described for Type Ia substituents except that the nitrogen containing compound employed in the displacement reaction is an aliphatic amine (i.e. NR$^y$R$^z$R$^w$). However, in cases where the amino group is directly bonded to the fluoren-9-one nucleus (i.e. —A$_p$N$^+$R$^y$R$^z$R$^w$ where p=0) the amine is most conveniently attached to the fluoren-9-one prior to its incorporation into the carbapenem system. If such an amine is primary or secondary, it may require protection with a suitable amine protecting group during the steps employed to attach the fluoren-9-one to the carbapenem. Tertiary amines require no protection and may be quaternized or protonated as described for the Type Ib cationic substituents.

The Type Id cationic substituents may be prepared by quaternization or protonation of a non-aromatic ring nitrogen of an appropriate neutral precursor substituents on the fluoren-9-one ring. Quaternization or protonation is accomplished as described above for the Type Ib substituents. As with the Type Ib substituents, the neutral precursor may already be attached to the fluoren-9-one ring at the time of its connection to the carbapenem, or the neutral precursor may be elaborated from a simpler precursor substituent on the fluoren-9-one ring after its connection to the carbapenem. Examples of neutral precursor substituents are: —CONH(3-quinuclidinyl), —CO[4-(N-methylpiperidinyl)], —SO$_2$CH$_2$CH$_2$[2-(N-methylpyrrolidinyl)], —SO$_2$[1-(4-methylpiperazinyl)] and —CH$_2$[1-(4-methylpiperazinyl)]. Elaboration of the neutral precursor substituent from a simpler substituent such as hydroxymethyl may be accomplished in an analogous manner to that described previously for the Type Ib substituents by employing appropriate reagents to introduce the Type Id non-aromatic ring nitrogen moiety which is subsequently to be quaternized or protonated.

Among preferred $R^a$ of Type II are $C_{1-4}$ alkyl mono-substituted with hydroxy, such as, hydroxymethyl; formyl; carboxy, such as, —COOM; carbamoyl, such as, —CONH$_2$; hydroximinomethyl, such as, —CH=NOH or cyano.

In regard to this preferred substitution, the hydroxymethyl may be obtained in any of the 1-, 5-, 6-, 7- and 8-positions of the fluoren-9-one ring as shown in Flow Sheets A, B and C. Flow Sheet A shows the synthesis of the 1-substituted isomer. The hydroxymethyl may be obtained in positions 5, 6, 7 or 8 by starting with the appropriate isomer of B6 and following the procedure of Flow Sheet B. The methyl of isomeric B6 may be oxidized e.g. to carboxy with chromium trioxide or to bromomethyl with N-bromosuccinimide. This oxidation of the precursor substituent, methyl, is advantageously performed prior to coupling with the carbapenem as the oxidizing conditions are incompatible with the subsequent carbapenem. The resultant 5-, 6-, 7- or 8-carboxy or bromomethyl substituted fluoren-9-one may be further elaborated to prepare the desired hydroxymethyl compound B9.

Proceeding according to Flow Sheet F, and employing A11 or isomeric B9 as starting material F3, the corresponding hydroxymethyl substituted F5 may be obtained. Alternatively, elaboration of the hydroxymethyl substituent into another preferred Type II $R^a$ substituent may be carried-out as described below prior to coupling of the fluoren-9-one side chain to the carbapenem. In certain instances, depending on the particular $R^a$ substituent being sought, such elaboration may also be performed on F5 after attachment of the fluoren-9-one side chain to the carbapenem. As previously described, the corresponding 2-fluoren-9-one regioisomers of F5 can be prepared analogously by starting with the appropriate 2-bromofluoren-9-one isomer of F3, which in turn is derived from appropriately substituted biphenyls by following the steps outlined in Flow Sheets A, B and C.

The preferred formyl substitution on the fluoren-9-one may be obtained from the hydroxymethyl substitution of A11 or isomeric B9 just described by a Swern oxidation. For example, isomeric B9 is oxidized in methylene chloride at from −70° C. to room temperature employing oxalyl chloride-dimethyl sulfoxide as the active agent. Obviously, the position of the resultant formyl substitution will depend upon the position of the hydroxymethyl substitution in isomeric B9.

The preferred —CH=NOH substitution on the fluoren-9-one may be conveniently obtained from the formyl substitution just described. This is accomplished simply by exposing the formyl substituted compound to hydroxylamine in an appropriate solvent at room temperature.

The preferred cyano substitution on the fluoren-9-one may be obtained from the —CH=NOH substitution just described. The —CH=NOH substituted compound is dehydrated with triflic anhydride and triethylamine in a solvent at −70° C.

The preferred —COOM substitution on the fluoren-9-one may be obtained from the hydroxymethyl Of isomeric B9. For example, an isomeric B9 is oxidized with Jones reagent to convert the hydroxymethyl substituent into a carboxyl group. The oxidation with Jones reagent may be incompatible with the carbapenem and thus is optimally performed before coupling with the carbapenem. Prior to coupling, the carboxy is protected as its p-nitrobenzyl ester. Protection is carried out by alkylating with p-nitrobenzyl bromide and triethylamine. The 1-substituted isomer may be prepared by analogous protection of A7. Deprotection is carried out by hydrogenolysis in the final step to yield the desired sodium or potassium salt.

The preferred carbamoyl substitution on the fluoren-9-one, may be obtained from isomeric B9 by oxidizing the hydroxymethyl with Jones reagent to the corresponding carboxylic acid as described above. This carboxy or A7 is converted to —CONH$_2$ by sequentially contacting with 1-ethyl-3-(3-dimethylaminopropyl)carbodiimide hydrochloride, 1-hydroxybenzotriazole, and ammonia in an organic solvent at room temperature. Substituted amides may of course be obtained by replacing ammonia with the corresponding substituted amine.

In addition to or including the above, suitable $R^a$ of Type II include:

| | |
|---|---|
| —OCH$_3$ | |
| —OCH$_2$CH$_2$OH | —OCH$_2$CO$_2$Na |
| —F | —CF$_3$ |
| —Br | —Cl |
| —OH | —I |
| —OCONH$_2$ | —OCOCH$_3$ |
| —SOCH$_3$ | —SCH$_3$ |
| —SCH$_2$CH$_2$OH | —SO$_2$CH$_3$ |
| —SO$_2$NH$_2$ | —SOCH$_2$CH$_2$OH |
| —NHCHO | —SO$_2$N(CH$_3$)$_2$ |
| —NHCO$_2$CH$_3$ | —NHCOCH$_3$ |
| —CN | —NHSO$_2$CH$_3$ |
| —COCH$_3$ | —CHO |
| —CH=NOH | —COCH$_2$OH |
| —CH=NOCH$_2$CO$_2$H | —CH=NOCH$_3$ |
| —SO$_2$CH$_2$CH$_2$OH | —CH=NOCMe$_2$CO$_2$H |
| —CH=NOCMe$_2$CO$_2$Me | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$H |
| —CONHOH | —CONHCH$_3$ |
| -tetrazolyl | —CO$_2$Na |
| —SCF$_3$ | —PO$_3$NaH |
| —CONHSO$_2$Ph | —CONHSO$_2$NH$_2$ |
| —SO$_3$Na | —SO$_2$NHCN |
| —SO$_2$NHCONH$_2$ | —CH=CHCN |
| —CH=CHCONH$_2$ | —CH=CHCO$_2$Na |
| —C≡C—CONH$_2$ | —C≡C—CN |
| —CH$_2$OH | —CH$_2$N$_3$ |
| —CH$_2$CO$_2$Na and | —CH$_2$I. |

In the preparation methods described above, the carboxyl group at the 3-position and the hydroxyl group at the 8-position of the carbapenem remain blocked by protecting groups until the final product is prepared. These blocking groups are readily removable, i.e.,they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation. Suitable hydroxyl protecting groups, P', in addition to or including those shown in the schemes, are t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Suitable carboxyl protecting groups, M, in addition to and including those shown in the schemes are: benzhydryl, o-nitrobenzyl, p-nitrobenzyl, 2-naphthylmethyl, allyl, 2-chloroallyl, benzyl, 2,2,2-trichloroethyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl. Many other suitable hydroxyl and carboxyl protecting groups are known in the art [see for example T. W. Greene, *Protective Groups in Organic Synthesis*, John Wiley & Sons, Inc., 1981 (Chapters 2 and 5)].

Deblocking may be carried out in a conventional manner. For compounds prepared according to Flow Sheet E, deprotection may be carried out first by desilylation using tetrabutylammonium fluoride and acetic acid and second by deallylation using a palladium catalyzed reaction in a solution containing potassium 2-ethylhexanoate or, alternatively, another suitable nucleophile such as pyrrolidine. Alternatively, for those prepared via Flow Sheet F, deprotection is conducted sequentially. Thus, compound F5 is exposed initially to aqueous acidic conditions, acetic acid or dilute HCl or the like, in an organic solvent such as tetrahydrofuran at 0° C. to 50° C. for from a few minutes to several hours. The resulting desilylated carbapenem may be isolated by conventional techniques, but is more conveniently taken into the final deprotection process. Thus, addition of an inorganic base such as $NaHCO_3$ or $KHCO_3$ or buffer such as sodium phosphate and 10% Pd/C followed by hydrogenation provides for the removal of the p-nitrobenzyl protecting group and the formation of the final compound of Formula I.

The overall molecule must be electronically balanced. Since a quaternary nitrogen is present in the compounds of the present invention, a balancing anion must also, in that case, be present. This is usually accomplished by allowing COOM to be $COO^-$. However, where M is, e.g., a pharmaceutically acceptable ester, a counterion (anion) $X^-$ must be provided, or alternatively, an anionic substituent might be utilized. A counterion must also be provided, or additional anionic substituent utilized where there is more than one quaternary nitrogen. Further, it is within the scope of this invention to utilize an anionic substituent where the quaternary nitrogen is already balanced by $COOM = COO^-$. In that case, it will be understood that it is necessary to provide a counterion (cation) for the anionic substituent. However, it is well within the skill of a medicinal chemist, to whom there is available many suitable anionic and cationic counterions, to make such choices.

With reference to the above definitions, "alkyl" means a straight or branched chain aliphatic hydrocarbon radical.

The term "quaternary nitrogen" as used herein refers to a tetravalent cationic nitrogen atom including the cationic nitrogen atom in a tetra-alkylammonium group (e.g. tetramethylammonium, N-methylpyridinium), the cationic nitrogen atom in a protonated ammonium species (e.g. trimethylhydroammonium, N-hydropyridinium), the cationic nitrogen atom in an amine N-oxide (e.g. N-methylmorpholine-N-oxide, pyridine-N-oxide), and the cationic nitrogen atom in an N-amino-ammonium group (e.g. N-aminopyridinium).

The term "heteroatom" means N, S, or O, selected on an independent basis.

The term "heteroaryl" has been defined herein, in relation to the $R^x$ group, to have a specific and limited meaning, being only monocyclic. While the cationic groups of Type I. a) and b) also clearly include heteroaryl groups, being both monocyclic and bicyclic, the term "heteroaryl" has not been used in association with the definitions of those cationic groups above. It is required that the monocyclic heteroaryl have at least one nitrogen atom, and optionally at most only one additional oxygen or sulfur heteroatom may be present. Heteroaryls of this type are pyrrole and pyridine (one N); and oxazole, thiazole or oxazine (one N+one O or one S). While additional nitrogen atoms may be present together with the first nitrogen and oxygen or sulfur, giving, e.g., a thiadiazole (two N's+one S), the preferred heteroaryls are those where only nitrogen heteroatoms are present when there is more than one. Typical of these are pyrazole, imidazole, pyrimidine and pyrazine (two N's) and triazine (three N's).

The heteroaryl group of $R^x$ is always optionally monosubstituted by $R^q$, defined above, and substitution can be on one of the carbon atoms or one of the heteroatoms, although in the latter case certain substitutent choices may not be appropriate.

Listed in Tables I, II, III and IV are specific compounds of the instant invention:

TABLE I

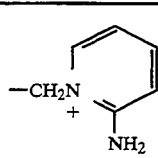

| M | $R^a$ | $R^a$ Position |
|---|---|---|
| (−) | 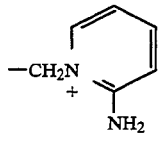 —CH$_2$N$^+$ ... NH$_2$ | 4 |
| (−) | —CH$_2$N$^+$ ... NH$_2$ | 5 |
| (−) | —CH$_2$N$^+$ ... NH$_2$ | 6 |
| (−) | —CH$_2$N$^+$ ... NH$_2$ | 7 |
| (−) | —CH$_2$N$^+$ ... NH$_2$ | 8 |
| (−) | —CH$_2$N$^+$ ... NH$_2$ | 4 |
| (−) | —CH$_2$N$^+$ ... NH$_2$ | 5 |
| (−) | —CH$_2$N$^+$ ... NH$_2$ | 6 |

TABLE I-continued

[Structure: β-lactam fused with pyrroline bearing COOM group, with hydroxyethyl substituent and fluorenone-linked aryl group at position 2; R^a shown on fluorenone ring with positions 4, 6, 7]

| M | R^a | R^a Position |
|---|-----|--------------|
| (−) | −CH₂N⁺=CH−C₆H₄−NH₂ (pyridinium-4-amino) | 7 |
| (−) | −CH₂N⁺=CH−C₆H₄−NH₂ (pyridinium-4-amino) | 8 |
| (−) | −CH₂N⁺(imidazolium)−N−CH₃ | 4 |
| (−) | −CH₂N⁺(imidazolium)−N−CH₃ | 5 |
| (−) | −CH₂N⁺(imidazolium)−N−CH₃ | 6 |
| (−) | −CH₂N⁺(imidazolium)−N−CH₃ | 7 |
| (−) | −CH₂N⁺(imidazolium)−N−CH₃ | 8 |
| (−) | −CH₂N⁺(imidazolium)−N−CH₂C₆H₅ | 4 |
| (−) | −CH₂N⁺(imidazolium)−N−CH₂C₆H₅ | 5 |
| (−) | −CH₂N⁺(imidazolium)−N−CH₂C₆H₅ | 6 |
| (−) | −CH₂N⁺(imidazolium)−N−CH₂C₆H₅ | 7 |
| (−) | −CH₂N⁺(imidazolium)−N−CH₂C₆H₅ | 8 |
| (−) | −CH₂N⁺(pyrazolium)−N−CH₃ | 4 |
| (−) | −CH₂N⁺(triazolium)−N−CH₃ | 5 |
| (−) | −CH₂N⁺(triazolium)−N−CH₃ | 6 |
| (−) | −CH₂N⁺(triazolium)−N−CH₃ | 7 |
| (−) | −CH₂N⁺(triazolium)−N−CH₃ | 8 |
| (−) | −CH₂N⁺(pyrazolium)−N−CH₃ | 4 |
| (−) | −CH₂N⁺(pyrazolium)−N−CH₃ | 5 |
| (−) | −CH₂N⁺(pyrazolium)−N−CH₃ | 6 |
| (−) | −CH₂N⁺(pyrazolium)−N−CH₃ | 7 |
| (−) | −CH₂N⁺(pyrazolium)−N−CH₃ | 8 |
| (−) | −CH₂N⁺(pyrazolium)−N−NH₂ | 4 |
| (−) | −CH₂N⁺(pyrazolium)−N−NH₂ | 5 |
| (−) | −CH₂N⁺(pyrazolium)−N−NH₂ | 6 |
| (−) | −CH₂N⁺(pyrazolium)−N−NH₂ | 7 |

TABLE I-continued

[Structure: carbapenem with HO-CH(CH3)- group, beta-lactam fused to pyrroline with COOM, attached at position 2 to a fluorenone bearing Rᵃ at indicated position; H or CH3 at ring position]

| M | Rᵃ | Rᵃ Position |
|---|---|---|
| (−) | −CH₂N⁺(=CH-N=CH-)N−NH₂ (imidazole-like with NH₂) | 8 |
| (−) | −CH₂N⁺(pyrrole)–N(CH₃) | 4 |
| (−) | −CH₂N⁺(pyrrole)–N(CH₃) | 5 |
| (−) | −CH₂N⁺(pyrrole)–N(CH₃) | 6 |
| (−) | −CH₂N⁺(pyrrole)–N(CH₃) | 7 |
| (−) | −CH₂N⁺(pyrrole)–N(CH₃) | 8 |

TABLE II

[Structure: same carbapenem core attached to fluorenone bearing (Rᵃ)₂ substituents at two positions]

| M | Rᵃ | Rᵃ Position | Rᵃ | Rᵃ Position |
|---|---|---|---|---|
| (−) | CO₂K | 4 | −CH₂N⁺(pyridine-2-NH₂) | 7 |
| (−) | tetrazole-NK (CH₃-C=N-N=N-NK) | 4 | −CH₂N⁺(pyridine-2-NH₂) | 7 |
| (−) | tetrazole-NK | 4 | −CH₂N⁺(pyridine-4-NH₂) | 7 |
| (−) | SO₃K | 4 | −CH₂N⁺(pyridine-4-NH₂) | 7 |

TABLE II-continued
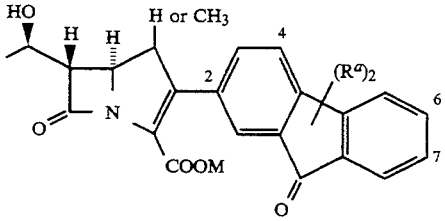
| M | $R^a$ | $R^a$ Position | $R^a$ | $R^a$ Position |
|---|---|---|---|---|
| (−) | CHO | 4 | 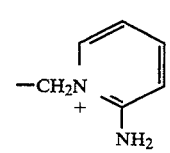 | 7 |
| (−) | CN | 4 | 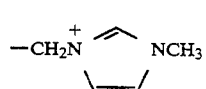 | 7 |
| (−) | $SOCH_3$ | 4 | 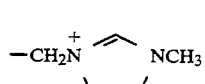 | 7 |
| (−) | $CO_2K$ | 4 | 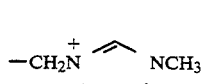 | 7 |
| (−) | $CO_2K$ | 4 | 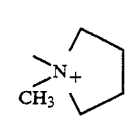 | 7 |
| (−) | $SO_3K$ | 4 | 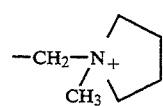 | 7 |
| (−) | $SO_3K$ | 6 | 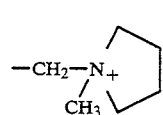 | 7 |
| (−) | $CH_2OH$ | 4 | 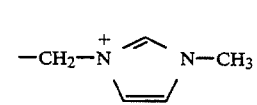 | 7 |
| (−) | $CH_2OH$ | 4 | 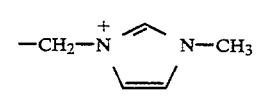 | 6 |
| (−) | $CONH_2$ | 4 | 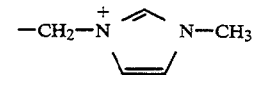 | 7 |
| (−) | $CONH_2$ | 4 | 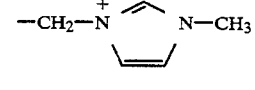 | 8 |
| (−) | $SCH_3$ | 4 |  | 7 |

TABLE II-continued

[Structure: fused β-lactam with HO-CH(CH3)- substituent, H or CH3 at position adjacent, connected via C=C with COOM to a fluorenone system bearing (Rᵃ)₂ substituents at positions 4, 6, 7]

| M | Rᵃ | Rᵃ Position | Rᵃ | Rᵃ Position |
|---|---|---|---|---|
| (−) | SCH₃ | 4 | −CH₂−N⁺(=CH−CH=CH−)N−CH₂C₆H₅ (imidazolium) | 6 |
| (−) | CH=N−OCH₃ | 4 | −CH₂−N⁺(imidazolium)−CH₂C₆H₅ | 7 |
| (−) | CH=N−OCH₃ | 4 | −CH₂−N⁺(imidazolium)−CH₂C₆H₅ | 6 |
| (−) | CH=N−OCH₃ | 4 | −CH₂−N⁺(imidazolium)−CH₂C₆H₅ | 8 |
| (−) | CH₃ | 4 | −CH₂−N⁺(imidazolium)−CH₃ | 7 |
| (−) | CHO | 4 | −CH₂−N⁺(imidazolium)−CH₃ | 6 |
| (−) | CHO | 4 | −CH₂−N⁺(imidazolium)−CH₃ | 7 |
| (−) | CO₂CH₃ | 4 | −CH₂−N⁺(imidazolium)−CH₃ | 7 |
| (−) | CH=N−OCH₃ | 4 | −CH₂−N⁺(imidazolium)−CH₃ | 8 |
| (−) | CN | 4 | −CH₂−N⁺(imidazolium)−CH₂C₆H₅ | 7 |
| (−) | CHO | 4 | −CH₂−N⁺(imidazolium)−CH₂C₆H₅ | 6 |
| (−) | CONH₂ | 4 | −CH₂−N⁺(imidazolium)−CH₂C₆H₅ | 7 |
| (−) | CH₂OH | 4 | −CH₂−N⁺(imidazolium)−CH₂C₆H₅ | 8 |
| (−) | CH₂OH | 7 | −CH₂−N⁺(imidazolium)−CH₃ | 4 |

TABLE II-continued

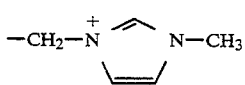

| M | $R^a$ | $R^a$ Position | $R^a$ | $R^a$ Position |
|---|---|---|---|---|
| (−) | CHO | 6 | $-CH_2-\overset{+}{N}\diagup\diagdown N-CH_3$ | 4 |
| (−) | $CO_2CH_3$ | 7 | $-CH_2-\overset{+}{N}\diagup\diagdown N-CH_3$ | 4 |
| (−) | $CH=N-OCH_3$ | 8 | $-CH_2-\overset{+}{N}\diagup\diagdown N-CH_3$ | 4 |
| (−) | CN | 7 | $-CH_2-\overset{+}{N}\diagup\diagdown N-CH_2C_6H_5$ | 4 |
| (−) | CHO | 6 | $-CH_2-\overset{+}{N}\diagup\diagdown N-CH_2C_6H_5$ | 4 |
| (−) | $CONH_2$ | 7 | $-CH_2-\overset{+}{N}\diagup\diagdown N-CH_2C_6H_5$ | 4 |
| (−) | $CH_2OH$ | 6 | $-CH_2-\overset{+}{N}\diagup\diagdown N-CH_2C_6H_5$ | 4 |
| (−) | $CH_2OH$ | 4 | $-CH_2-\overset{+}{N}\diagup\diagdown N-CH_3$ (triazole) | 7 |
| (−) | CHO | 7 | $-CH_2-\overset{+}{N}\diagup\diagdown N-CH_3$ (triazole) | 4 |
| (−) | $CO_2CH_3$ | 6 | $-CH_2-\overset{+}{N}\diagup\diagdown N-CH_3$ (triazole) | 4 |
| (−) | $CH=N-OCH_3$ | 4 | $-CH_2-\overset{+}{N}\diagup\diagdown N-CH_3$ (triazole) | 6 |
| (−) | CN | 8 | $-CH_2-\overset{+}{N}\diagup\diagdown N-CH_3$ (triazole) | 4 |
| (−) | CHO | 6 | $-CH_2-\overset{+}{N}\diagup\diagdown N-CH_3$ (triazole) | 4 |

TABLE II-continued

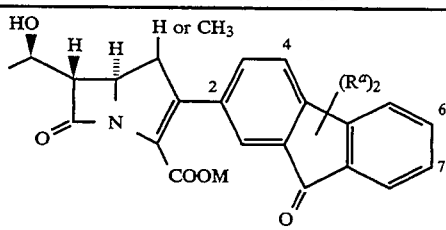

| M | $R^a$ | $R^a$ Position | $R^a$ | $R^a$ Position |
|---|---|---|---|---|
| (−) | $CONH_2$ | 4 | −CH$_2$−N$^+$=CH−N(NH$_2$)−CH=CH (imidazole-type, N−NH$_2$) | 7 |
| (−) | $CH_2OH$ | 4 | −CH$_2$−N$^+$=CH−N(NH$_2$)−CH=CH | 6 |
| (−) | $CONH_2$ | 4 | −CH$_2$−N$^+$(CH$_3$)−N=CH−CH=CH (pyrazolium) | 7 |
| (−) | $CH_2OH$ | 4 | −CH$_2$−N$^+$(CH$_3$)−N=CH−CH=CH | 6 |

TABLE III

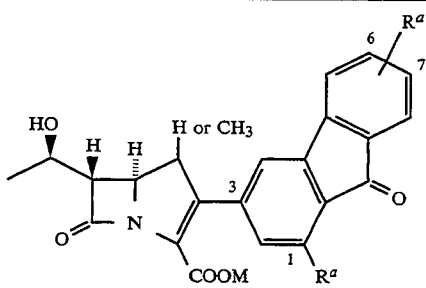

| M | $R^a$ | $R^a$ Position |
|---|---|---|
| (−) | −CH$_2$N$^+$=pyridinium-2-NH$_2$ | 1 |
| (−) | −CH$_2$N$^+$=pyridinium-2-NH$_2$ | 5 |
| (−) | −CH$_2$N$^+$=pyridinium-2-NH$_2$ | 6 |
| (−) | −CH$_2$N$^+$=pyridinium-2-NH$_2$ | 7 |

TABLE III-continued

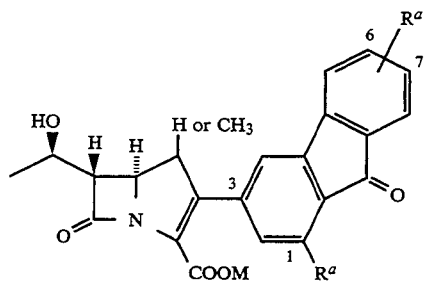

| M | $R^a$ | $R^a$ Position |
|---|---|---|
| (−) | −CH$_2$N$^+$=pyridinium-2-NH$_2$ | 8 |
| (−) | −CH$_2$N$^+$=pyridinium-4-NH$_2$ | 1 |
| (−) | −CH$_2$N$^+$=pyridinium-4-NH$_2$ | 5 |
| (−) | −CH$_2$N$^+$=pyridinium-4-NH$_2$ | 6 |

TABLE III-continued

Structure (left column, entries at position 3 of fluorenone):

| M | Rᵃ | Rᵃ Position |
|---|---|---|
| (−) | −CH₂N⁺(pyridinium)-NH₂ | 7 |
| (−) | −CH₂N⁺(pyridinium)-NH₂ | 8 |
| (−) | −CH₂N⁺(imidazolium)−N−CH₃ | 1 |
| (−) | −CH₂N⁺(imidazolium)−N−CH₃ | 5 |
| (−) | −CH₂N⁺(imidazolium)−N−CH₃ | 6 |
| (−) | −CH₂N⁺(imidazolium)−N−CH₃ | 7 |
| (−) | −CH₂N⁺(imidazolium)−N−CH₃ | 8 |
| (−) | −CH₂N⁺(imidazolium)−N−CH₂C₆H₅ | 1 |
| (−) | −CH₂N⁺(imidazolium)−N−CH₂C₆H₅ | 5 |
| (−) | −CH₂N⁺(imidazolium)−N−CH₂C₆H₅ | 6 |
| (−) | −CH₂N⁺(imidazolium)−N−CH₂C₆H₅ | 7 |
| (−) | −CH₂N⁺(imidazolium)−N−CH₂C₆H₅ | 8 |
| (−) | −CH₂N⁺(1,2,4-triazolium)−N−CH₃ | 1 |

TABLE III-continued

| M | Rᵃ | Rᵃ Position |
|---|---|---|
| (−) | −CH₂N⁺(1,2,4-triazolium)−N−CH₃ | 5 |
| (−) | −CH₂N⁺(1,2,4-triazolium)−N−CH₃ | 6 |
| (−) | −CH₂N⁺(1,2,4-triazolium)−N−CH₃ | 7 |
| (−) | −CH₂N⁺(1,2,4-triazolium)−N−CH₃ | 8 |
| (−) | −CH₂N⁺(1,2,4-triazolium)−N−CH₃ | 1 |
| (−) | −CH₂N⁺(1,2,4-triazolium)−N−CH₃ | 5 |
| (−) | −CH₂N⁺(1,2,4-triazolium)−N−CH₃ | 6 |
| (−) | −CH₂N⁺(1,2,4-triazolium)−N−CH₃ | 7 |
| (−) | −CH₂N⁺(1,2,4-triazolium)−N−CH₃ | 8 |
| (−) | −CH₂N⁺(1,2,4-triazolium)−N−NH₂ | 1 |
| (−) | −CH₂N⁺(1,2,4-triazolium)−N−NH₂ | 5 |
| (−) | −CH₂N⁺(1,2,4-triazolium)−N−NH₂ | 6 |

TABLE III-continued

Structure (columns 55 and 56 show the same core structure):

Core: fluorenone-substituted carbapenem with HO-CH(CH₃)- group, H or CH₃ at C-4, COOM, and R$^a$ substituent on the fluorenone ring (positions 1, 6, 7, 8).

| M | R$^a$ | R$^a$ Position |
|---|---|---|
| (−) | −CH₂N⁺(pyrazole-NH₂, triazole-type) with N−NH₂ | 7 |
| (−) | −CH₂N⁺(triazole) N−NH₂ | 8 |
| (−) | −CH₂N⁺(pyrazole)−N−CH₃ | 1 |
| (−) | −CH₂N⁺(pyrazole)−N−CH₃ | 5 |
| (−) | −CH₂N⁺(pyrazole)−N−CH₃ | 6 |
| (−) | −CH₂N⁺(pyrazole)−N−CH₃ | 7 |
| (−) | −CH₂N⁺(pyrazole)−N−CH₃ | 8 |
| K | −CH₂N⁺(pyridine)−NCH₂SO₃⁻ | 1 |
| K | −CH₂N⁺(pyridine)−NCH₂CO₂⁻ | 1 |
| K | −CH₂N⁺(pyridine)−CH₂CH₂SO₃⁻ | 1 |
| K | −CH₂N⁺(pyridine)−CO₂⁻ | 1 |
| (−) | −CH₂N⁺(pyridine)−NCH₂CH₂OH | 1 |
| K | −CH₂N⁺(pyridine)−NCH₂SO₃⁻ | 6 |
| K | −CH₂N⁺(pyridine)−NCH₂CO₂⁻ | 6 |
| K | −CH₂N⁺(pyridine)−CH₂CH₂SO₃⁻ | 6 |
| K | −CH₂N⁺(pyridine)−CO₂⁻ | 6 |
| (−) | −CH₂N⁺(pyridine)−NCH₂CH₂OH | 6 |
| K | −CH₂N⁺(pyridine)−NCH₂SO₃⁻ | 7 |
| K | −CH₂N⁺(pyridine)−NCH₂CO₂⁻ | 7 |
| K | −CH₂N⁺(pyridine)−CH₂CH₂SO₃⁻ | 7 |
| K | −CH₂N⁺(pyridine)−CO₂⁻ | 7 |
| (−) | −CH₂N⁺(pyridine)−NCH₂CH₂OH | 7 |
| K | −CH₂N⁺(pyridine)−NCH₂SO₃⁻ | 8 |

TABLE III-continued
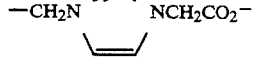
| M | $R^a$ | $R^a$ Position |
|---|---|---|
| K | 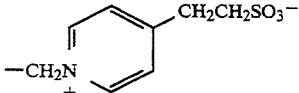 | 8 |
| K | 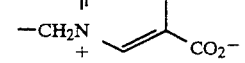 | 8 |
| K | 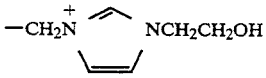 | 8 |
| (−) | 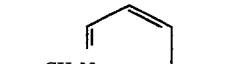 | 8 |
| (−) | 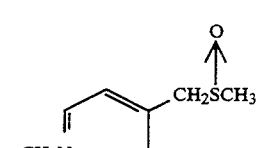 | 1 |
| (−) | 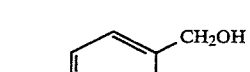 | 1 |
| (−) | 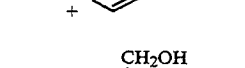 | 1 |
| (−) | 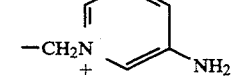 | 1 |
| (−) | $-CH_2\overset{+}{N}H(CH_3)_2$ | 1 |
| (−) | $-CO_2CH_2CH_2\overset{+}{N}H(CH_3)_2$ | 1 |
| (−) | 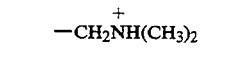 | 1 |
TABLE III-continued
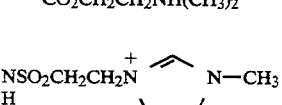
| M | $R^a$ | $R^a$ Position |
|---|---|---|
| (−) | 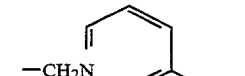 | 6 |
| (−) |  | 6 |
| (−) | 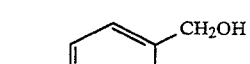 | 6 |
| (−) | 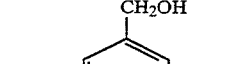 | 6 |
| (−) | $-CH_2\overset{+}{N}H(CH_3)_2$ | 6 |
| (−) | $-CO_2CH_2CH_2\overset{+}{N}H(CH_3)_2$ | 6 |
| (−) | 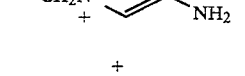 | 6 |
| (−) | 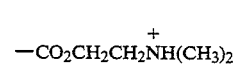 | 7 |
| (−) | 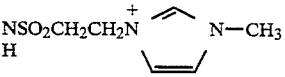 | 7 |
| (−) | 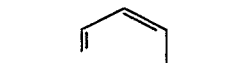 | 7 |

TABLE III-continued

[Structure: fused β-lactam with hydroxyethyl group, connected at position 3 to a fluorenone bearing R^a substituents at positions 6/7 and 1; N-substituted with COOM]

| M | R^a | R^a Position |
|---|---|---|
| (−) | −CH₂N⁺(pyridyl-CH₂OH, NH₂) | 7 |
| (−) | −CH₂N⁺H(CH₃)₂ | 7 |
| (−) | −CO₂CH₂CH₂N⁺H(CH₃)₂ | 7 |
| (−) | −NHSO₂CH₂CH₂N⁺(imidazolyl-N−CH₃) | 7 |
| (−) | −CH₂N⁺(pyridyl-NH₂) | 8 |
| (−) | −CH₂N⁺(pyridyl-CH₂S(O)CH₃, NH₂) | 8 |
| (−) | −CH₂N⁺(pyridyl-CH₂OH) | 8 |
| (−) | −CH₂N⁺(pyridyl-CH₂OH, NH₂) | 8 |
| (−) | −CH₂N⁺H(CH₃)₂ | 8 |
| (−) | −CO₂CH₂CH₂N⁺H(CH₃)₂ | 8 |
| (−) | −NHSO₂CH₂CH₂N⁺(imidazolyl-N−CH₃) | 8 |
| (−) | −OCH₂CH₂N⁺(pyridyl-NH₂) | 1 |
| (−) | −SCH₂CH₂N⁺(pyridyl-NH₂) | 1 |
| (−) | −SO₂CH₂CH₂N⁺(pyridyl-NH₂) | 1 |
| (−) | −CH₂OCH₂CH₂N⁺(pyridyl-NH₂) | 1 |
| (−) | −CH₂SCH₂CH₂N⁺(pyridyl-NH₂) | 1 |
| (−) | −CH₂S(O)₂CH₂CH₂N⁺(pyridyl-NH₂) | 1 |
| (−) | −OCH₂CH₂N⁺(pyridyl-NH₂) | 6 |
| (−) | −SCH₂CH₂N⁺(pyridyl-NH₂) | 6 |

TABLE III-continued

Structure: fluorenone-substituted pyrroline with (HO)CH(CH₃)- group, H or CH₃ at position adjacent, COOM, positions 1, 3, 6, 7 indicated, Rᵃ substituent.

| M | Rᵃ | Rᵃ Position |
|---|---|---|
| (−) | −SO₂CH₂CH₂N⁺=⟨pyridyl⟩-NH₂ | 6 |
| (−) | −CH₂OCH₂CH₂N⁺=⟨pyridyl⟩-NH₂ | 6 |
| (−) | −CH₂SCH₂CH₂N⁺=⟨pyridyl⟩-NH₂ | 6 |
| (−) | −CH₂S(O)₂N⁺=⟨pyridyl⟩-NH₂ | 6 |
| (−) | −OCH₂CH₂N⁺=⟨pyridyl⟩-NH₂ | 7 |
| (−) | −SCH₂CH₂N⁺=⟨pyridyl⟩-NH₂ | 7 |
| (−) | −SO₂CH₂CH₂N⁺=⟨pyridyl⟩-NH₂ | 7 |
| (−) | −CH₂OCH₂CH₂N⁺=⟨pyridyl⟩-NH₂ | 7 |

TABLE III-continued

Same core structure as above.

| M | Rᵃ | Rᵃ Position |
|---|---|---|
| (−) | −CH₂SCH₂CH₂N⁺=⟨pyridyl⟩-NH₂ | 7 |
| (−) | −CH₂S(O)₂N⁺=⟨pyridyl⟩-NH₂ | 7 |
| (−) | −OCH₂CH₂N⁺=⟨pyridyl⟩-NH₂ | 8 |
| (−) | −SCH₂CH₂N⁺=⟨pyridyl⟩-NH₂ | 8 |
| (−) | −SO₂CH₂CH₂N⁺=⟨pyridyl⟩-NH₂ | 8 |
| (−) | −CH₂OCH₂CH₂N⁺=⟨pyridyl⟩-NH₂ | 8 |
| (−) | −CH₂SCH₂CH₂N⁺=⟨pyridyl⟩-NH₂ | 8 |
| (−) | −CH₂S(O)₂N⁺=⟨pyridyl⟩-NH₂ | 8 |

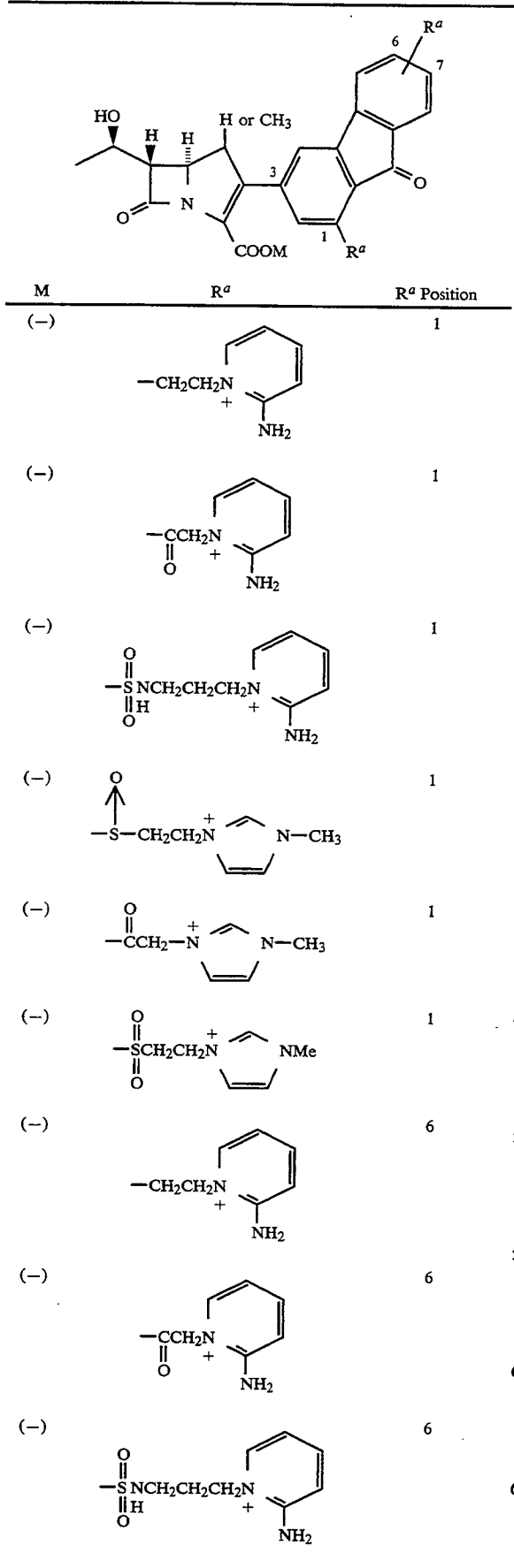
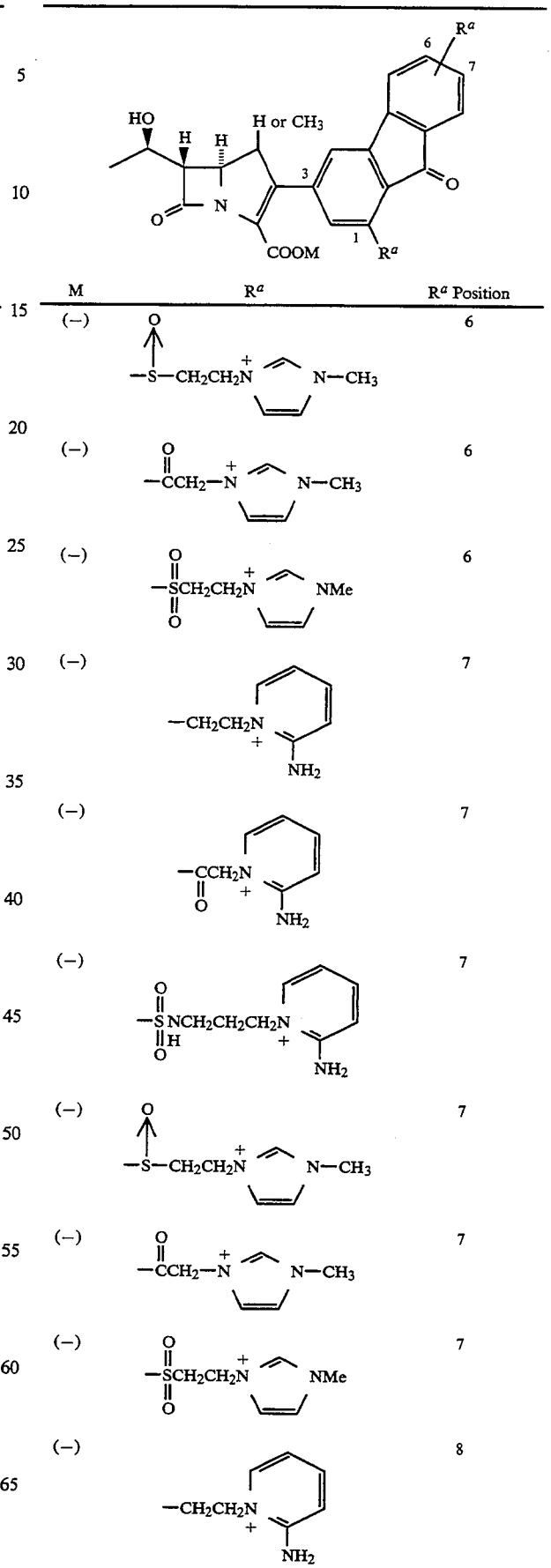

TABLE III-continued
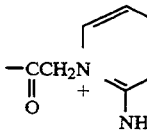
| M | $R^a$ | $R^a$ Position |
|---|---|---|
| (—) | 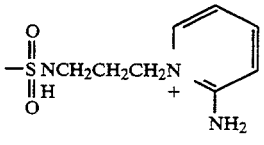 | 8 |
| (—) | 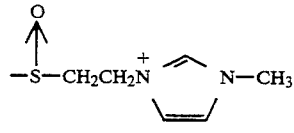 | 8 |
| (—) | 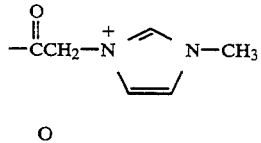 | 8 |
| (—) | 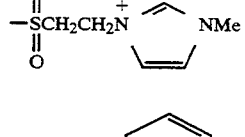 | 8 |
| (—) | 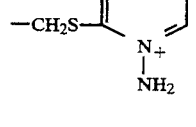 | 8 |
| (—) | 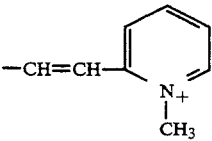 | 1 |
| (—) | 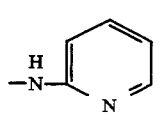 | 1 |
| H | 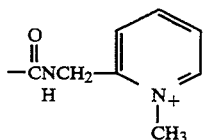 | 1 |
| (—) | 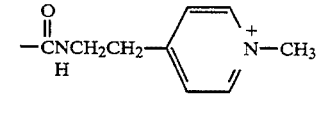 | 1 |
TABLE III-continued
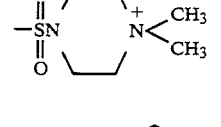
| M | $R^a$ | $R^a$ Position |
|---|---|---|
| (—) | 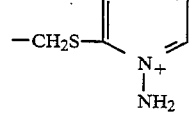 | 1 |
| (—) | 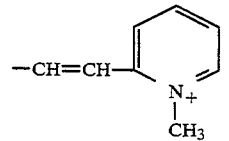 | 1 |
| (—) | 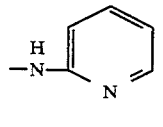 | 6 |
| (—) | 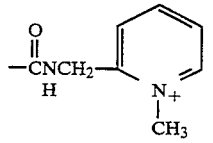 | 6 |
| H | 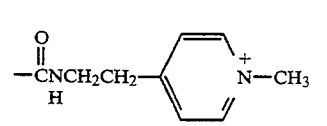 | 6 |
| (—) | 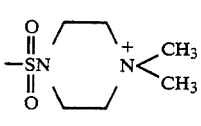 | 6 |
| (—) |  | 6 |
| (—) |  | 6 |
| (—) |  | 7 |

TABLE III-continued

| M | $R^a$ | $R^a$ Position |
|---|---|---|
| (−) | −CH=CH− (2-(1-methylpyridinium)) | 7 |
| H | −NH− (2-pyridyl) | 7 |
| (−) | −C(O)NHCH₂− (2-(1-methylpyridinium)) | 7 |
| (−) | −C(O)NHCH₂CH₂− (4-(1-methylpyridinium)) | 7 |
| (−) | −SO₂−N(thiomorpholine dioxide N-dimethyl ammonium) | 7 |
| (−) | −CH₂S− (2-(1-aminopyridinium)) | 8 |
| (−) | −CH=CH− (2-(1-methylpyridinium)) | 8 |
| H | −NH− (2-pyridyl) | 8 |
| (−) | −C(O)NHCH₂− (2-(1-methylpyridinium)) | 8 |

TABLE III-continued

| M | $R^a$ | $R^a$ Position |
|---|---|---|
| (−) | −C(O)NHCH₂CH₂− (4-(1-methylpyridinium)) | 8 |
| (−) | −SO₂−N(thiomorpholine dioxide N-dimethyl ammonium) | 8 |
| (−) | −SO₂CH₂− (2-(1-methylpyridinium)) | 1 |
| (−) | −CH₂− (2-amino-1-methylpyridinium at 4-position) | 1 |
| (−) | −CH₂− (1-(carbamoylmethyl)pyridinium at 4-position) | 1 |
| K | −C(O)NHCH₂CH₂− (2-pyridinium N-oxide) | 1 |
| K | −SO₂CH₂− (4-pyridinium N-oxide) | 1 |
| (−) | −C(O)NH− (1-methylquinuclidinium) | 1 |
| (−) | −SO₂CH₂CH₂− (2-(1-methylpyridinium)) | 6 |

TABLE III-continued

| M | $R^a$ | $R^a$ Position |
|---|---|---|
| (−) | −CH$_2$−(4-pyridinium-1-methyl-2-amino) | 6 |
| (−) | −CH$_2$−(4-pyridinium-N-CH$_2$CONH$_2$) | 6 |
| K | −C(O)NHCH$_2$CH$_2$−(2-pyridinium-N-oxide) | 6 |
| K | −S(O$_2$)CH$_2$−(4-pyridinium-N-oxide) | 6 |
| (−) | −C(O)NH−(quinuclidinium-N-CH$_3$) | 6 |
| (−) | −S(O$_2$)−CH$_2$CH$_2$−(2-pyridinium-N-CH$_3$) | 7 |
| (−) | −CH$_2$−(4-pyridinium-N-CH$_3$-2-amino) | 7 |
| (−) | −CH$_2$−(4-pyridinium-N-CH$_2$CONH$_2$) | 7 |
| K | −C(O)NHCH$_2$CH$_2$−(2-pyridinium-N-oxide) | 7 |
| K | −S(O$_2$)CH$_2$−(4-pyridinium-N-oxide) | 7 |
| (−) | −C(O)NH−(quinuclidinium-N-CH$_3$) | 7 |
| (−) | −S(O$_2$)−CH$_2$CH$_2$−(2-pyridinium-N-CH$_3$) | 8 |
| (−) | −CH$_2$−(4-pyridinium-N-CH$_3$-2-amino) | 8 |
| (−) | −CH$_2$−(4-pyridinium-N-CH$_2$CONH$_2$) | 8 |
| K | −C(O)NHCH$_2$CH$_2$−(2-pyridinium-N-oxide) | 8 |
| K | −S(O$_2$)CH$_2$−(4-pyridinium-N-oxide) | 8 |
| (−) | −C(O)NH−(quinuclidinium-N-CH$_3$) | 8 |
| (−) | N-methylpyrrolidinium | 1 |
| (−) | −CH$_2$−(N-methylmorpholinium) | 1 |

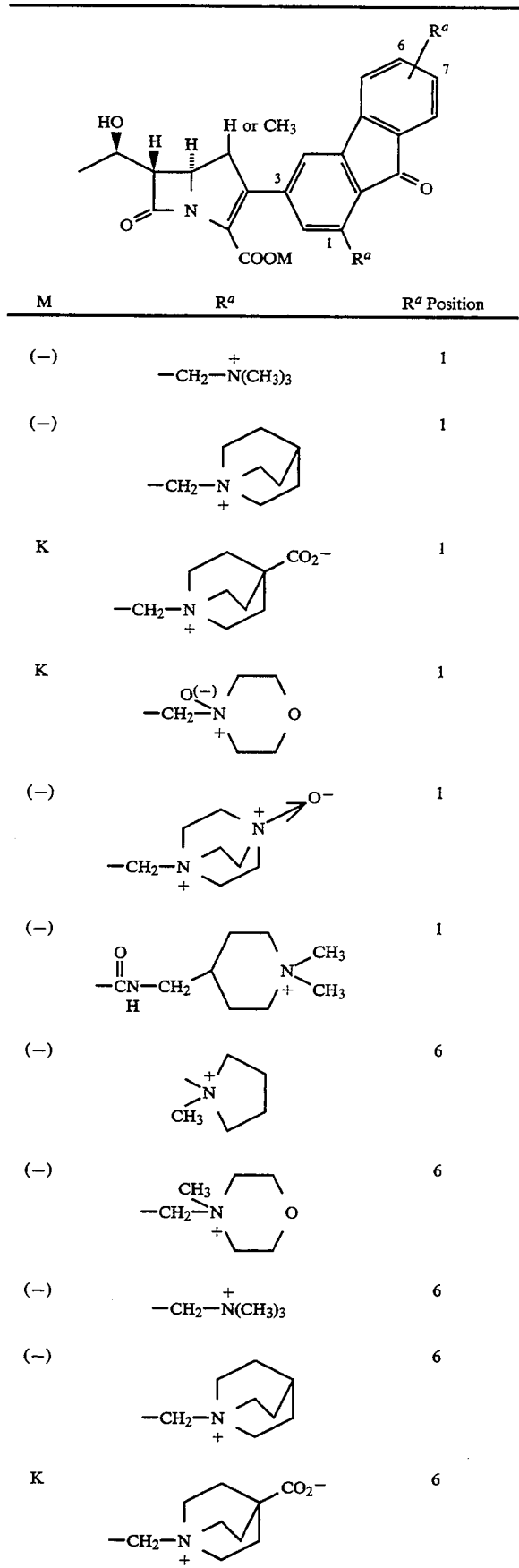
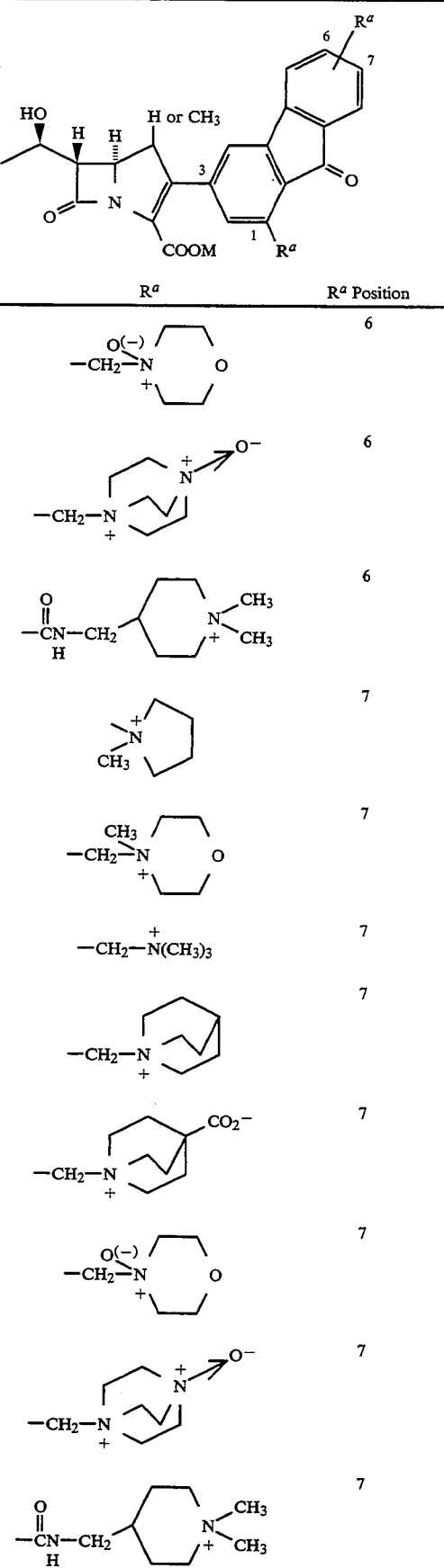

TABLE III-continued
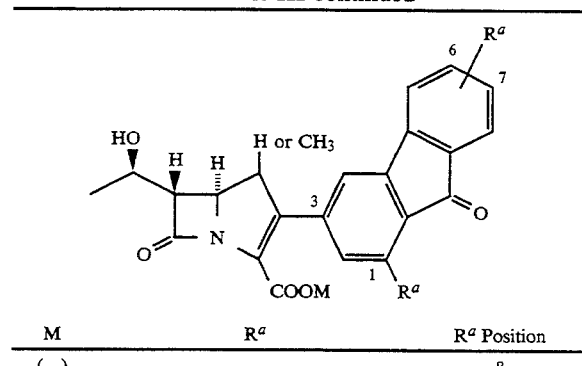
| M | R$^a$ | R$^a$ Position |
|---|---|---|
| (−) | 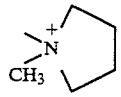 | 8 |
| (−) | 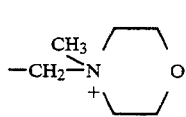 | 8 |
| (−) | −CH$_2$−N$^+$(CH$_3$)$_3$ | 8 |
| (−) | 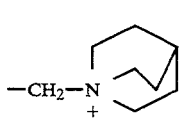 | 8 |
TABLE III-continued
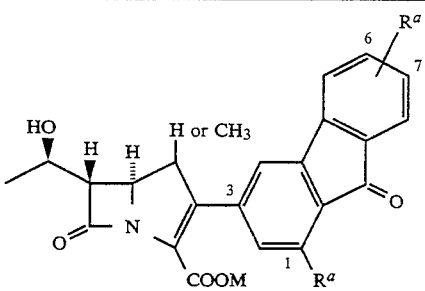
| M | R$^a$ | R$^a$ Position |
|---|---|---|
| K | 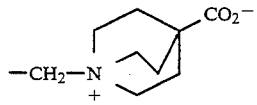 | 8 |
| K | 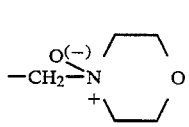 | 8 |
| (−) | 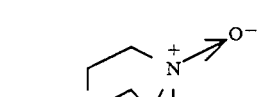 | 8 |
| (−) | 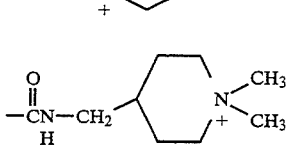 | 8 |
TABLE IV
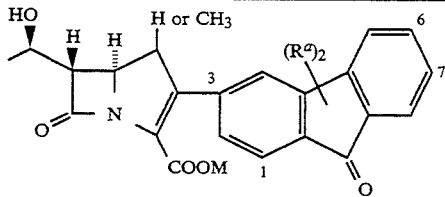
| M | R$^a$ | R$^a$ Position | R$^a$ | R$^a$ Position |
|---|---|---|---|---|
| (−) | CO$_2$K | 1 | 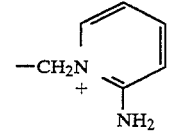 | 7 |
| (−) | 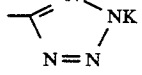 | 1 | 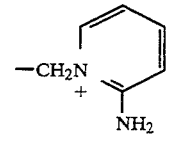 | 7 |
| (−) | 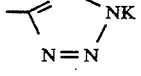 | 1 | 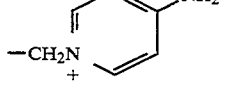 | 7 |
| (−) | SO$_3$K | 1 | 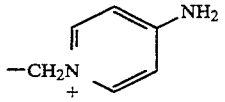 | 7 |

TABLE IV-continued

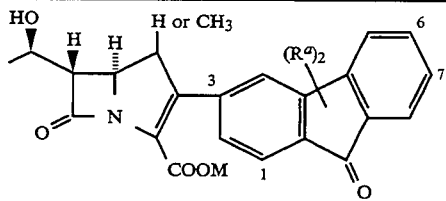

| M | $R^a$ | $R^a$ Position | $R^a$ | $R^a$ Position |
|---|---|---|---|---|
| (−) | CHO | 1 | −CH₂N⁺(pyridinyl-NH₂) | 7 |
| (−) | CN | 1 | −CH₂N⁺(imidazolyl)NCH₃ | 7 |
| (−) | SOCH₃ | 1 | −CH₂N⁺(imidazolyl)NCH₃ | 7 |
| (−) | CO₂K | 1 | −CH₂N⁺(imidazolyl)NCH₃ | 7 |
| (−) | CO₂K | 1 | N-methylpyrrolidinium | 7 |
| (−) | SO₃K | 1 | −CH₂−N⁺(pyrrolidinyl)CH₃ | 7 |
| (−) | SO₃K | 6 | −CH₂−N⁺(pyrrolidinyl)CH₃ | 7 |
| (−) | CH₂OH | 1 | −CH₂−N⁺(imidazolyl)N−CH₃ | 7 |
| (−) | CH₂OH | 1 | −CH₂−N⁺(imidazolyl)N−CH₃ | 6 |
| (−) | CONH₂ | 1 | −CH₂−N⁺(imidazolyl)N−CH₃ | 7 |
| (−) | CONH₂ | 1 | −CH₂−N⁺(imidazolyl)N−CH₃ | 8 |
| (−) | SCH₃ | 1 | −CH₂−N⁺(imidazolyl)N−CH₂C₆H₅ | 7 |

TABLE IV-continued

[Structure: bicyclic β-lactam core with HO-CH(CH3)- group, H and H stereochemistry, H or CH3 at position, attached at C3 to a fluorenone system with (Rª)2 substituents at positions 1, 6, 7, 8; COOM group; 9-oxo group]

| M | Rª | Rª Position | Rª | Rª Position |
|---|---|---|---|---|
| (−) | SCH₃ | 1 | −CH₂−N⁺(=CH−N−CH₂C₆H₅)(imidazolium) | 6 |
| (−) | CH=N−OCH₃ | 1 | −CH₂−N⁺(=CH−N−CH₂C₆H₅)(imidazolium) | 7 |
| (−) | CH=N−OCH₃ | 1 | −CH₂−N⁺(=CH−N−CH₂C₆H₅)(imidazolium) | 6 |
| (−) | CH=N−OCH₃ | 1 | −CH₂−N⁺(=CH−N−CH₂C₆H₅)(imidazolium) | 8 |
| (−) | CH₃ | 1 | −CH₂−N⁺(=CH−N−CH₃)(imidazolium) | 7 |
| (−) | CHO | 1 | −CH₂−N⁺(=CH−N−CH₃)(imidazolium) | 6 |
| (−) | CHO | 1 | −CH₂−N⁺(=CH−N−CH₃)(imidazolium) | 7 |
| (−) | CO₂CH₃ | 1 | −CH₂−N⁺(=CH−N−CH₃)(imidazolium) | 7 |
| (−) | CH=N−OCH₃ | 1 | −CH₂−N⁺(=CH−N−CH₃)(imidazolium) | 8 |
| (−) | CN | 1 | −CH₂−N⁺(=CH−N−CH₂C₆H₅)(imidazolium) | 7 |
| (−) | CHO | 1 | −CH₂−N⁺(=CH−N−CH₂C₆H₅)(imidazolium) | 6 |
| (−) | CONH₂ | 1 | −CH₂−N⁺(=CH−N−CH₂C₆H₅)(imidazolium) | 7 |
| (−) | CH₂OH | 1 | −CH₂−N⁺(=CH−N−CH₂C₆H₅)(imidazolium) | 8 |
| (−) | CH₂OH | 1 | −CH₂−N⁺(=CH−N−CH₃)(triazolium) | 7 |

TABLE IV-continued
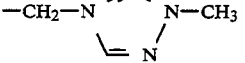
| M | $R^a$ | $R^a$ Position | $R^a$ | $R^a$ Position |
|---|---|---|---|---|
| (−) | CHO | 7 | 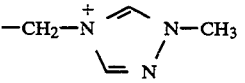 | 1 |
| (−) | $CO_2CH_3$ | 6 |  | 1 |
| (−) | $CH=N-OCH_3$ | 1 |  | 6 |
| (−) | CN | 8 | 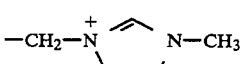 | 1 |
| (−) | CHO | 6 | 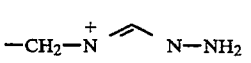 | 1 |
| (−) | $CONH_2$ | 1 |  | 7 |
| (−) | $CH_2OH$ | 1 | 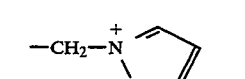 | 6 |
| (−) | $CONH_2$ | 1 | 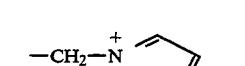 | 7 |
| (−) | $CH_2OH$ | 1 | 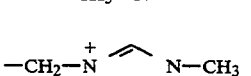 | 6 |
| (−) | $CH_2OH$ | 7 |  | 1 |
| (−) | CHO | 6 |  | 1 |
| (−) | $CO_2CH_3$ | 7 | 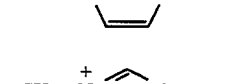 | 1 |
| (−) | $CH=N-OCH_3$ | 8 | 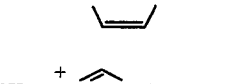 | 1 |
| (−) | CN | 7 | $-CH_2-\overset{+}{N}\diagup\hspace{-6pt}=\hspace{-6pt}\diagdown N-CH_2C_6H_5$ | 1 |

TABLE IV-continued

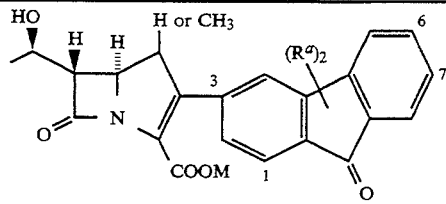

| M | $R^a$ | $R^a$ Position | $R^a$ | $R^a$ Position |
|---|---|---|---|---|
| (−) | CHO | 6 | $-CH_2-\overset{+}{N}\underset{\diagdown\!=\!\diagup}{\diagup\phantom{xx}\diagdown}N-CH_2C_6H_5$ | 1 |
| (−) | CONH$_2$ | 7 | $-CH_2-\overset{+}{N}\underset{\diagdown\!=\!\diagup}{\diagup\phantom{xx}\diagdown}N-CH_2C_6H_5$ | 1 |
| (−) | CH$_2$OH | 6 | $-CH_2-\overset{+}{N}\underset{\diagdown\!=\!\diagup}{\diagup\phantom{xx}\diagdown}N-CH_2C_6H_5$ | 1 |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist. i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalare, pamoate, pectinate, persulfate, 3-phenylpropionate, picrate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protecting groups include benzhydryl, o-nitrobenzyl, p-nitrobenzyl, 2-naphthylmethyl, allyl, benzyl, 2,2,2-trichloroethyl, 2-(trimethylsilyl)ethyl, phenacyl, p-methoxybenzyl, t-butyldiphenylsilyl, acetonyl, p-methoxyphenyl, 4-pyridylmethyl, and t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder from for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occurring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4, filed Jul. 24, 1979 (Patent No. 0 007 614); and NO. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

EXAMPLE 1

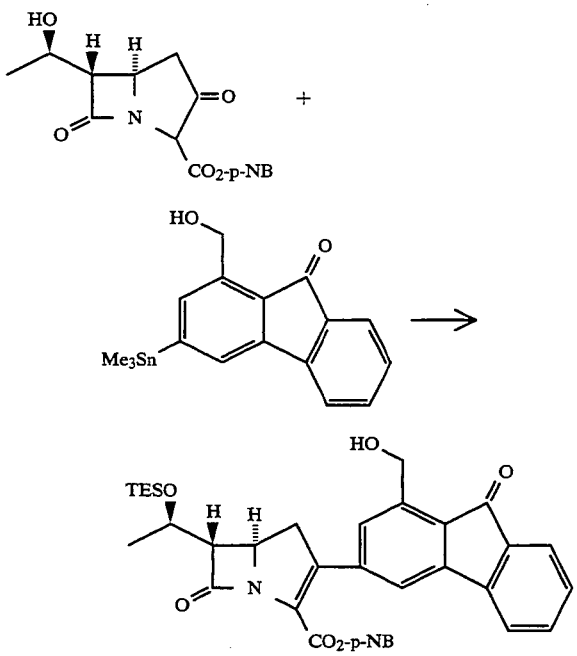

p-Nitrobenzyl
(5R,6S)-2-(1-hydroxymethyl-9-fluorenon-3-yl)-6-(1R-triethysilyloxyethyl)carbapen-2-em-3-carboxylate p-Nitrobenzyl (5R,6S)-2-oxo-6-(1R-hydroxyethyl)-carbapenem-3-carboxylate (143 mg, 0.41 mmoles) was dissolved in 2 ml THF and cooled to −78° under $N_2$, diisopropylamine (63 microliter, 1.1 eq) added followed 10 min later by trifluoromethanesulfonic anhydride (75 microliter, 1.1 eq). The reaction mixture allowed to stir at −78° for 15 min. Triethylamine (62 μl, 1.1 eq) was then added followed by triethylsilyl trifluoromethanesulfonate (108 μl, 1.1 eq). The reaction mixture was allowed to stir at −78° for 20 min. Pd₂(DBA)₃.CHCl₃ (8.5 mg, 0.02 eq) and tris(2,4,6-trimethoxyphenyl)phosphine (17.4 mg, 0.08 eq) were added followed by 3-trimethylstannyl-1-hydroxymethyl-9-fluorenone (100 mg, 0.27 mmoles) in THF (1 ml). N-methylpyrrolidone (3 ml) was added followed by ZnCl₂ (0.45 ml, 1M soln in Et₂O). The cooling bath was removed and the reaction mixture was brought rapidly to r.t. and allowed to stir 0.5 hr. The reaction mixture diluted with Et₂O/EtOAc 4:1, 25 ml and washed with pH 7 phosphate buffer (0.2M), then with water and brine then dried over Na₂SO₄ and evaporated gave a residue which when purified by preparative tlc (30% EtOAc/hexane elution) gave the product (128 mg, 73%).

¹H-NMR (CDCl₃,200 MHz): δ0.62 (q, J=7, CH₃—CH₂—Si); 0.96 (t, J=7, CH₃—CH₂—Si ); 1.32 (d, J=7, CH₃—C); 3.32 (m, C-6H and C-1H); 4.32 (m, C-5H and CH₃—CH—); 4.86 (s, CH₂OH); 5.21, 5.37 (2d, J=12, ArCH₂O); 7.13–8.2 (m, ArH).

EXAMPLE 2

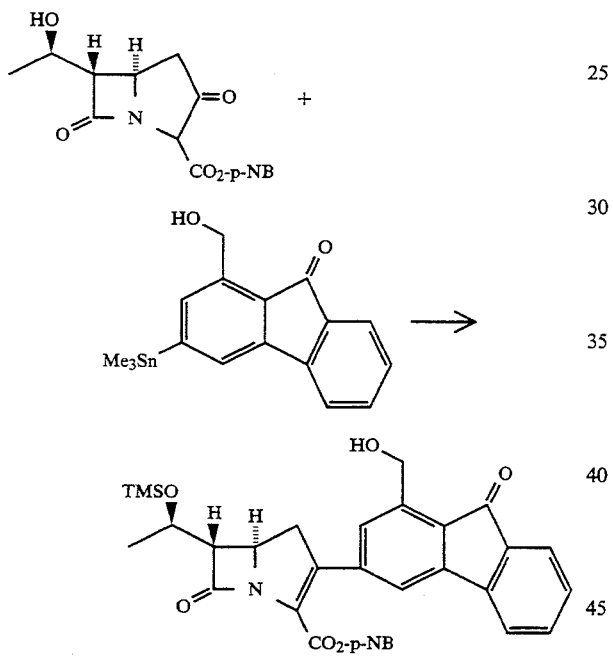

p-Nitrobenzyl (5R,6S)-2-(1-hydroxymethyl-9-fluorenon-3-yl)-6-(1R-trimethylsilyloxyethyl)carbapen-2-em-3-carboxylate Using 1.1 eq of trimethylsilyl trifluoromethane sulfonate in place of triethysilyl trifluoromethane sulfonate in Example 1 gave the desired product.

¹H-NMR (CDCl₃,200 MHz): δ0.096 (s, CH₃—Si); 1.32 (d, J=7, CH₃—C); 3.32 (m, C-6H and C-1H); 4.32 (m, C-5H and CH₃—CH—); 4.86 (s, CH₂OH); 5.21, 5.37 (2d, J=12, ArCH₂O); 7.13–8.2 (m, ArH).

EXAMPLE 3

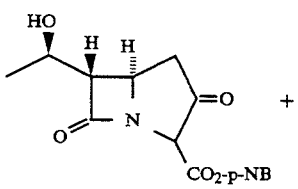

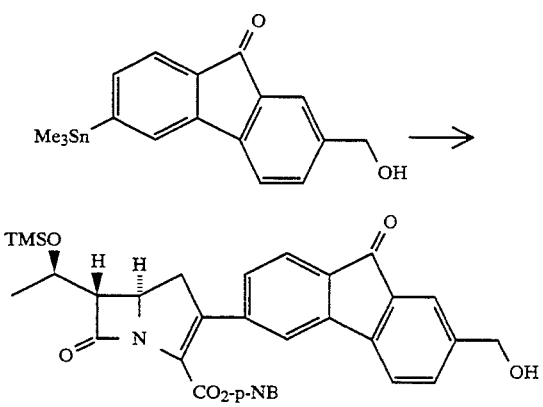

p-Nitrobenzyl (5R,6S)-2-(7-hydroxymethyl-9-fluorenon-3-yl)-6-(1R-trimethylsilyloxyethyl)carbapen-2-em-3-carboxylate Using 1.1 eq of trimethylsilyl triflate in place of triethylsilyl triflate and 3-trimethylstannyl-7-hydroxymethyl-9- fluorenone in place of 3-trimethylstannyl-1-hydroxymethyl-9-fluorenone in Example 1 gave the desired product.

¹H-NMR (CDCl₃, 200 MHz): δ0.16 (s, CH₃—Si); 1.33 (d, J=7, CH₃—C); 3.30 (m, C-6H and C-1H); 4.31 (m, C-5H and CH₃—CH—); 4.74 (s, CH₂OH); 5.27 (ABq, J=14, ArCH₂O); 7.18–8.04 (m, ArH).

EXAMPLE 4

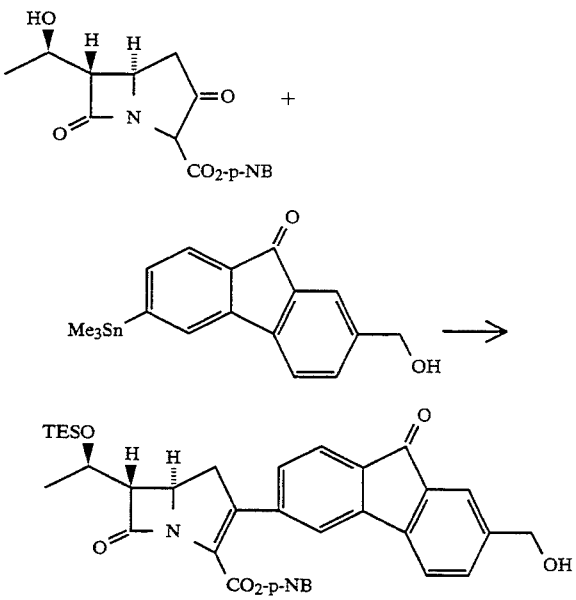

p-Nitrobenzyl (5R,6S)-2-(7-hydroxymethyl-9-fluorenon-3-yl)-6-(1R-triethylsilyloxyethyl)carbapen-2-em-3-carboxylate Using 3-trimethylstannyl-7-hydroxymethyl-9-fluorenone in place of 3-trimethylstannyl-1-hydroxymethyl-9-fluorenone in Example 1 gave the desired product.

¹H-NMR (CDCl₃, 200 MHz): δ0.63 (q, J=7, CH₃—CH₂—Si); 0.96 (t, J=7, CH₃—CH₂—Si); 1.30 (d, J=7, CH₃—C); 3.32 (m, C-6H and C-1H); 4.31 (m, C-5H and CH₃—CH—); 4.72 (s, CH₂OH); 5.25 (ABq, J=12, ArCH₂O); 7.18–8.04 (m, ArH). IR (CH₂Cl₂, cm⁻¹): 1778, 1715.

EXAMPLE 5

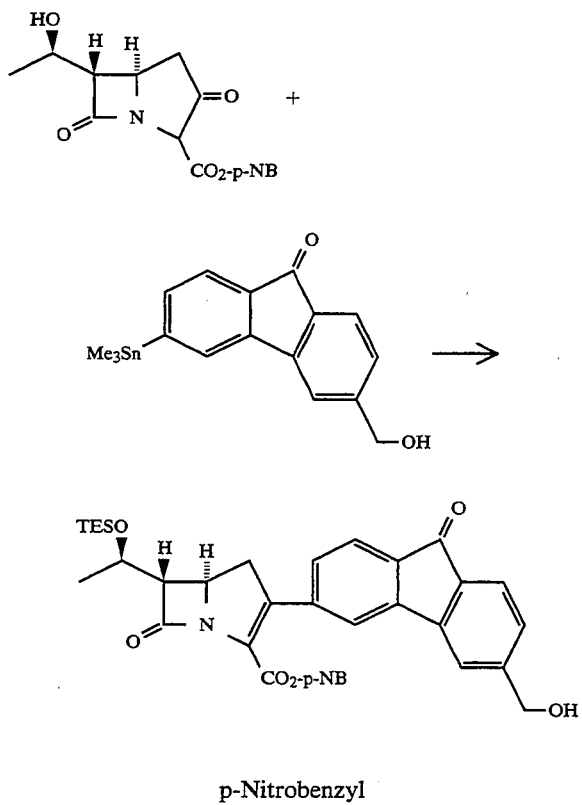

p-Nitrobenzyl (5R,6S)-2-(6-hydroxymethyl-9-fluorenon-3-yl)-6-(1R-triethylsilyloxyethyl)carbapen-2-em-3-carboxylate Using 3-trimethylstannyl-6-hydroxymethyl-9-fluorenone in place of 3-trimethylstannyl-1-hydroxymethyl-9-fluorenone in Example 1 one can obtain the named product.

EXAMPLE 6

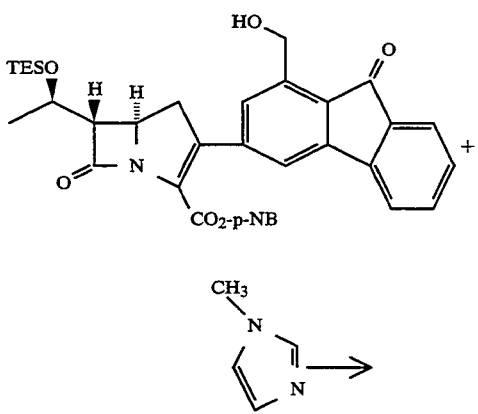

(5R,6S)-2-[1-(1-methylimidazolium-3-yl)methyl-9-fluorenon-3-yl]-6-(1R-hydroxyethyl)carbapen-2-em-3-carboxylate p-Nitrobenzyl (5R,6S)-2-(1-hydroxymethyl-9-fluorenon-3-yl)-6-(1R-triethylsilyloxyethyl)carbapen-2-em-3-carboxylate (27 mg) was dissolved in CH₂Cl₂ (1 ml, sieve dried) under N₂ and treated with 1-methylimidazole (8.12 mg, 2.4 eq) followed by trifluoromethanesulfonic anhydride (8.3 µl, 1.2 eq). The reaction mixture was stirred at room temperature for 0.5 hour. The reaction mixture was diluted with CH₂Cl₂ and washed once with pH 7 buffer and then with brine, dried over Na₂SO₄ and evaporated which gave p-Nitrobenzyl (5R,6S)-2-[1-(1-methylimidazolium-3-yl)methyl-9-fluorenon-3-yl]-6-(1R-triethylsilyloxyethyl)carbapen-2-em-3-carboxylate chloride.

¹H-NMR CDCl₃, 200 MHz): $\delta$0.63 (q, J=7, CH₃—CH₂—Si); 0.98 (t, J=7, CH₃—CH₂—Si); 1.31 (d, J=7, CH₃—C); 3.32 (d of d, C-1 Ha); 3.21 (d of d, C-6H); 3.62 (d of d, C-1 Hb); 3.97 (s, N—CH₃); 4.37 (m, C-5H and CH₃—CH—); 5.27, 5.43 (2d, J=12, ArCH₂O); 5.75 (s, CH₂N); 7.13–8.2 (m, ArH); 9.45 (s, C-2H of imidazolium).

This was dissolved in THF (1 ml) under N₂. HOAc (15 µl, 6 eq) was added and followed by tetrabutylammonium fluoride (82.5 µl, 1M soln, 2 eq). The reaction mixture was stirred at r.t. for 3 hours then diluted with CHCl₃ and washed once with pH 7 phosphate buffer, then with brine and dried over Na₂SO₄ and evaporated.

The residue which was impure p-Nitrobenzyl (5R,6S)-2-[1-(1-methylimidazolium-3-yl)methyl-9-fluorenon-3-yl]-6-(1R-hydroxyethyl)carbapen-2-em-3-carboxylate (IR (neat, cm⁻¹), 1770, 1720, 1702); was dissolved in THF (1 ml), EtOH (1 ml), H₂O (0.5 ml) and pH 7 sodium phosphate buffer (0.5 ml, 0.2M). 5% Pd/C catalyst 8 mg) was added and the mixture was hydrogenated at atmospheric pressure for 1 hour. The catalyst was filtered off, washed with water and the combined filtrate and washings are extracted three times with CHCl₃ and then evaporated to a small volume. The product was purified by reverse phase HPLC on a Whatman Partisil ODS3 column using a water/CH₃CN gradient elution which gave the product.

¹H-NMR (D₂O, 300 MHz): $\delta$1.43 (d, J=7, CH₃—C); 3.18 (d of d, J=16, J=9.5, C-1 Ha); 3.45 (d of d, J=16, J=10, C-1 Hb); 3.63 (d of d, J=6, J=2.5, C-6H); 3.96 (s, N—CH₃); 4.375 (m, CH₃—CH—); 4.68 (d of t, J=9, J=2.5, C-5H); 5.43, 5.54 (2d, J=15, ArCH₂N); 7.1–7.6 (m, ArH); 8.83 (s, imidazolium H). UV (H₂O, λmax): 257, 307, 368.

EXAMPLE 7

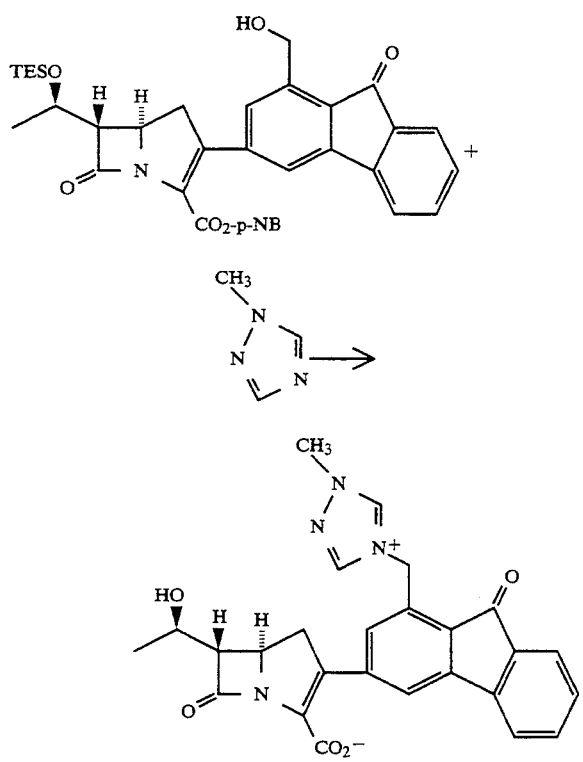

(5R,6S)-2-[1-(1-methyl-1,2,4-triazolium-4-yl)methyl-9-fluorenon-3-yl]-6-(1R-hydroxyethyl)carbapen-2-em-3-carboxylate Substituting 1-methyl-1,2,4-triazole in place of 1-methylimidazole in Example 6 gave (5R,6S)-2-[1-(1-methyl-1,2,4-triazolium-4-yl)methyl-9-fluorenon-3-yl]-6-(1R-hydroxyethyl)carbapen-2-em-3-carboxylate.

$^1$H-NMR (D$_2$O, 300 MHz): δ1.43 (d, J=7, CH$_3$—C); 3.26 (d of d, J=17, J=10, C-1 Ha); 3.45 (d of d, J=17, J=8.5, C-1 Hb); 3.7 (d of d, J=7, J=3, C-6H); 4.17 (s, N—CH$_3$); 4.384 (m, CH$_3$—CH—); 4.74 (d of t, J=9, J=3.0, C-5H); 5.64, 5.73 (2d, J=15, ArCH$_2$N); 7.1–7.6 (m, ArH); 3.91 (s, imidazolium H). UV (H$_2$O, λmax): 257, 307, 365.

EXAMPLE 8

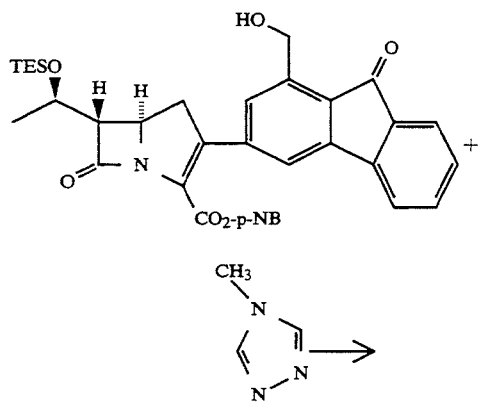

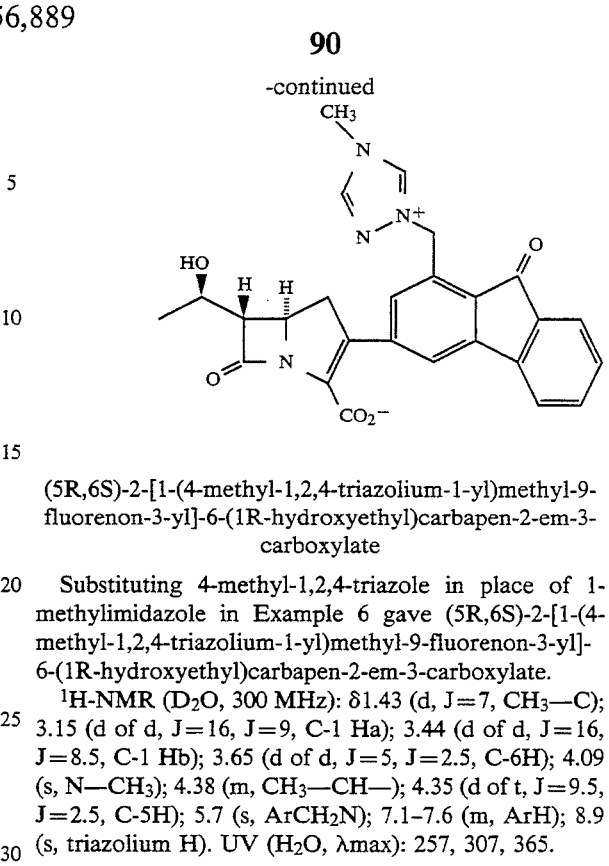

(5R,6S)-2-[1-(4-methyl-1,2,4-triazolium-1-yl)methyl-9-fluorenon-3-yl]-6-(1R-hydroxyethyl)carbapen-2-em-3-carboxylate Substituting 4-methyl-1,2,4-triazole in place of 1-methylimidazole in Example 6 gave (5R,6S)-2-[1-(4-methyl-1,2,4-triazolium-1-yl)methyl-9-fluorenon-3-yl]-6-(1R-hydroxyethyl)carbapen-2-em-3-carboxylate.

$^1$H-NMR (D$_2$O, 300 MHz): δ1.43 (d, J=7, CH$_3$—C); 3.15 (d of d, J=16, J=9, C-1 Ha); 3.44 (d of d, J=16, J=8.5, C-1 Hb); 3.65 (d of d, J=5, J=2.5, C-6H); 4.09 (s, N—CH$_3$); 4.38 (m, CH$_3$—CH—); 4.35 (d of t, J=9.5, J=2.5, C-5H); 5.7 (s, ArCH$_2$N); 7.1–7.6 (m, ArH); 8.9 (s, triazolium H). UV (H$_2$O, λmax): 257, 307, 365.

EXAMPLE 9

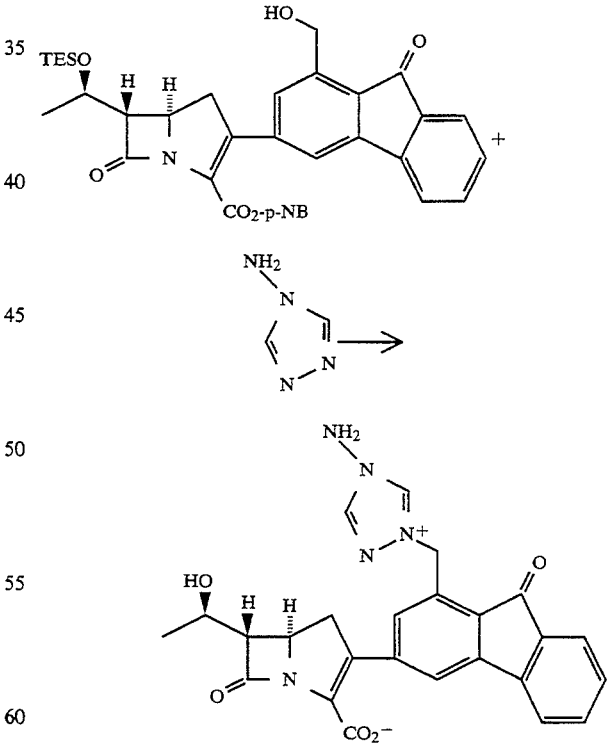

(5R,6S)-2-[1-(4-amino-1,2,4-triazolium-1-yl)methyl-9-fluorenon-3-yl]-6-(1R-hydroxyethyl)carbapen-2-em-3-carboxylate Substituting 4-amino-1,2,4-triazole in place of 1-methylimidazole in Example 6 gave (5R,6S)-2-[1-(4- amino-1,2,4-triazolium-1-yl)methyl-9-fluorenon-3-yl]-6-(1R-hydroxyethyl)carbapen-2-em-3-carboxylate.

1H-NMR (D2O, 300 MHz): δ1.45 (d, J=7, CH3—C); 3.17 (d of d, J=16, J=10, C-1 Ha); 3.46 (d of d, J=16, J=9, C-1 Hb); 3.65 (d of d, J=5, J=2.5, C-6H); 4.38 (m, CH3—CH—); 4.35 (d of t, J=9.5, J=2.5, C-5H); 5.72 (s, ArCH2N); 7.1–7.6 (m, ArH); 8.93 (s, triazolium H). UV (H2O, λmax): 257, 307, 365.

EXAMPLE 10

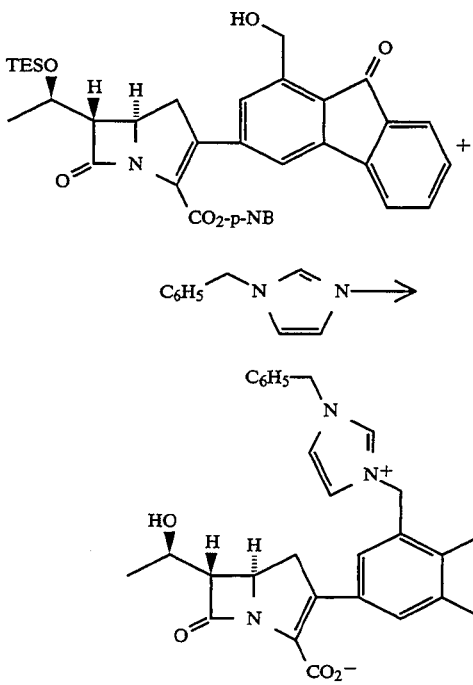

(5R,6S)-2-[1-(1-benzylimidazolium-3-yl)methyl-9-fluorenon-3-yl]-6-(1R-hydroxyethyl)carbapen-2-em-3-carboxylate Substituting 1-benzylimidazole in place of 1-methylimidazole in Example 6 gave (5R,6S)-2-[1-(1-benzylimidazolium-3-yl)methyl-9-fluorenon-3-yl]-6-(1R-hydroxyethyl)carbapen-2-em-3-carboxylate.

1H-NMR (D2O, 300 MHz): δ1.45 (d, J=7, CH3—C); 3.15 (d of d, J=16, J=10, C-1 Ha); 3.46 (d of d, J=16, J=7.5, C-1 Hb); 3.64 (d of d, J=6, J=2.5, C-6H); 4.38 (m, CH3—CH—); 4.45 (d of t, J=9.5, J=2.5, C-5H); 5.46 (s, ArCH2N); 5.44, 5.56 (2d, J=13, ArCH2N); 7.1–7.6 (m, ArH); 8.97 (s, imidazolium H). UV (H2O, λmax): 258, 307, 360.

EXAMPLE 11

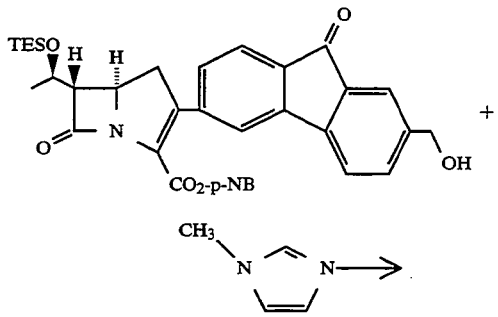

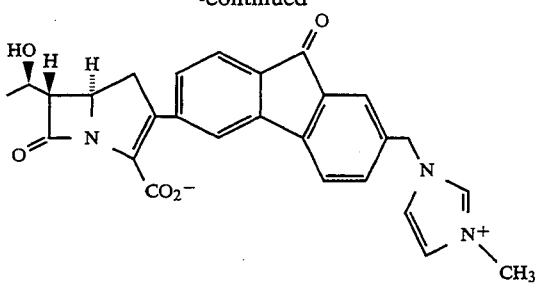

(5R,6S) 2-[7-(1-methylimidazolium-3-yl)methyl-9-fluorenone-3-yl]-6-(1R-hydroxyethyl)carbapen-2-em-3-carboxylate Substituting the 7-hydroxymethyl-9-fluorenone derivative of Example 4 as the starting material in place of 1-hydroxymethyl-9-fluorenone in Example 6 gave the desired compound.

1H-NMR (D2O, 300 MHz): δ1.43 (d, J=6, CH3—C); 3.14 (d of d, J=17, J=11, C-1 Ha); 3.47 (d of d, J=17, J=9, C-1 Hb); 3.65 (d of d, J=6, J=3.0, C-6H); 4.01 (s, N—CH3); 4.39 (m, CH3—CH—); 4.44 (d of t, J=9, J=3.0, C-5H); 5.40 (s, ArCH2N); 7.06–7.7 (m, ArH); 8.93 (s, imidazolium H). UV (H2O, λmax): 257, 305, 367.

EXAMPLE 12

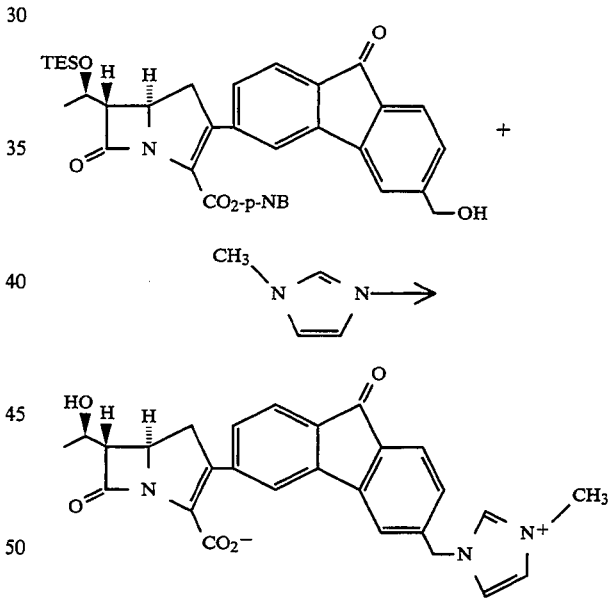

(5R,6S)-2-[6-(1-methylimidazolium-3-yl)methyl-9-fluroenon-3-yl]-6-(1R-hydroxyethyl)carbapen-2-em-3-carboxylate Substituting the 6-hydroxymethyl-9-fluorenone derivative of Example 5 in place of the 1-hydroxyfluorenone of Example 6 one obtains the named compound.

EXAMPLE 13

(5R,6S)-2-[7-(4-methyl-1,2,4-triazolium-1-yl)methyl-9-fluorenon-3-yl]-6-(1R-hydroxyethyl)carbapen-2-em-3-carboxylate Substituting the 7-hydroxymethyl-9-fluorenone derivative of Example 4 in place of 1-hydroxymethyl-9-fluorenone in Example 7 gave the desired compound.

$^1$H-NMR (D$_2$O, 300 MHz): δ1.44 (d, J=7, CH$_3$—C); 3.12 (d of d, J=17, J=9.5, C-1 Ha); 3.45 (d of d, J=17, J=8.5, C-1 Hb); 3.65 (d of d, J=5, J=2, C-6H); 4.12 (s, N—CH$_3$); 4.40 (m, CH$_3$—CH); 4.94 (m, C-5H) 5.58 (s, ArCH$_2$N); 7.02–7.50 (m, ArH); 8.98 (s, triazolium H). UV (H$_2$O, λmax): 255, 304.

EXAMPLE 14

(5R,6S)-2-[6-(4-methyl-1,2,4-triazolium-1-yl)methyl-9-fluorenon-3-yl]-6-(1R-hydroxyethyl)carbapen-2-em-3-carboxylate Substituting 6-hydroxymethyl-9-fluorenone derivatives of Example 5 in place of the 1-hydroxymethyl-9-fluorenone of Example 7 one obtains the named compound.

EXAMPLE 15

(5R,6S)-2-[7-(1-methyl-1,2,4-triazolium-4-yl)methyl-9-fluorenon-3-yl]-6-(1R-hydroxyethyl)carbapen-2-em-3-carboxylate Substituting the 7-hydroxymethyl-9-fluorenone derivative of Example 4 in place of 1-hydroxymethyl-9-fluorenone in Example 8 gave the desired compound.

$^1$H-NMR (D$_2$O, 300 MHz): δ1.45 (d, J=7, CH$_3$—C); 3.23 (d of d, J=16, J=10, C-1 Ha); 3.56 (d of d, J=16, J=8, C-1 Hb); 3.68 (d of d, J=2.5, J=6, C-6H); 4.23 (s, N—CH$_3$), 4.395 (m, CH$_3$—CH), 4.47 (d of t, J=8, J=2.5, C-5H); 5.6 (s, ArCH$_2$N); 7.2–7.7 (m, ArH); 9.05 (s, triazolium H). UV (H$_2$O, λmax): 257, 305, 365.

EXAMPLE 16

(5R,6S)-2-[6-(1-methyl-1,2,4-triazolium-4-yl)methyl-9-fluorenon-3-yl]-6-(1R-hydroxyethyl)carbapen-2-em-3-carboxylate Substituting 6-hydroxymethyl-9-fluorenone derivatives of Example 5 in place of the 1-hydroxymethyl-9-fluorenone of Example 8 one obtains the named compound.

EXAMPLE 17

(5R,6S)-2-[7-(4-amino-1,2,4-triazolium-1-yl)methyl-9-fluorenon-3-yl]-6-(1R-hydroxyethyl)carbapen-2-em-3-carboxylate Substituting a 7-hydroxymethyl-9-fluorenone derivative of Example 4 in place of 1-hydroxymethyl-9-fluorenone in Example 9 gave the desired compound.

$^1$H-NMR (D$_2$O, 300 MHz): δ1.47 (d, J=7, CH$_3$C); 3.11 (d of d J=16, J=9, C-1 Ha); 3.45 (d of d, J=16, J=9, C-1 Hb); 3.65 (d of d J=5, J=2.5, C-6H); 4.42 (m, CH$_3$—CH); 4.9 (m, C-5H), 5.54 (s, ArCH$_2$N); 7.0–7.38 (m, ArH), 9.04 (s, triazolium H). UV (H$_2$O, λmax): 259, 303.

EXAMPLE 18

(5R,6S)-2-[6-(4-amino-1,2,4-triazolium-1-yl)methyl-9-fluorenon-3-yl]-6-(1R-hydroxyethyl)carbapen-2-em-3-carboxylate Substituting 6-hydroxymethyl-9-fluorenone derivatives of Example 5 in place of the 1-hydroxymethyl-9-fluorenone of Example 9 one obtains the named compound.

EXAMPLE 19

(5R,6S)-2-[7-(1-benzylimidazolium-3-yl)methyl-9-fluorenon-3-yl]-6-(1R-hydroxyethyl)carbapen-2-em-3-carboxylate Substituting the 7-hydroxymethyl-9-fluorenone derivative of Example 4 in place of 1-hydroxymethyl-9-fluorenone in Example 10 one obtains the-named compound.

$^1$H-NMR (D$_2$O, 300 MHz): δ1.40 (d, J=7, CH$_3$C), 3.16 (m, C-1 Ha); 3.47 (m, C-1 Hb); 3.62 (m, C-6H); 4.39, (m, CH$_3$—CH); 4.89 (m, C-5H); 5.38 (d, J=3, CH$_2$—Ar); 5.48 (s, CH$_2$—N); 7.16–7.64 (m, ArH); 9.09 (s, imidazolium H). UV (H$_2$O, λmax): 259, 303.

EXAMPLE 20

(5R,6S)-2-[6-(1-benzylimidazolium-3-yl)methyl-9-fluorenon-3-yl]-6-(1R-hydroxyethyl)carbapen-2-em-3-carboxylate Substituting 6-hydroxymethyl-9-fluorenone derivatives of Example 5 in place of the 1-hydroxymethyl-9-fluorenone of Example 10 one obtains the named compound.

EXAMPLE 21

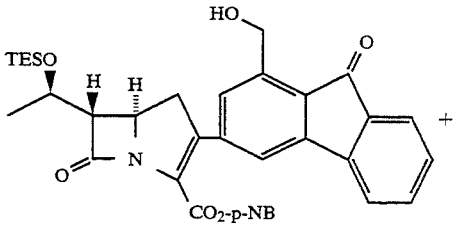

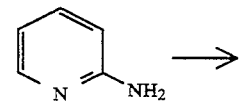

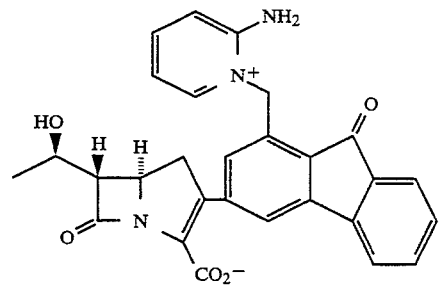

(5R,6S)-2-[1-(2-aminopyridinium)methyl-9-fluorenone-3-yl]-6-(1R-hydroxyethyl)carbapen-2-em-3-carboxylate p-Nitrobenzyl (5R,6S)-2-(1-hydroxymethyl-9-fluorenon-3-yl)-6-(1R-triethylsilyloxyethyl)carbapen-2-em-3-carboxylate (24 mg) was dissolved in CH$_2$Cl$_2$ (1 ml) and cooled to 0° under N$_2$. 2,6-Lutidine (5.2 μl, 1.2 eq) was added followed by trifluormethanesulfonic anhydride (7.4 μl, 1.2 eq). The reaction mixture was stirred at 0° for 0.5 hour. 2-Aminopyridine (4 mg, 1.2 eq) was added and the mixture was stirred at 0° for 1 hour and then evaporated to dryness which gave the impure p-nitrobenzyl (5R,6S)-2-[1-(2-aminopyridinium)methyl-9-fluorenon-3-yl]-6-(1R-triethylsilyloxyethyl)carbapen-2-em-3-carboxylate trifluoromethanesulfonate.

The triethylsilyl and p-nitrobenzyl groups were deblocked as described in Example 6, which gave the final product.

¹H-NMR (D₂O, 300 MHz): δ1.41 (d, J=7, CH₃—C); 2.94 (m, 9.5, C-1 Ha); 3.44 (m, C-1 Hb); 3.56 (d of d, J=6, J=2.5, C-6H; 4.32 (m, CH₃—CH and C-5H); 5.38, 5.47 (2d, J=18); 6.7-8.05 (m, ArH). UV (H2O, δmax): 256, 305, 355, 362.

EXAMPLE 22

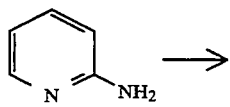

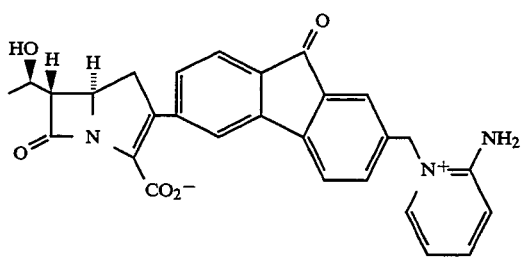

(5R,6S)-2-[7-(2-aminopyridinium)methyl-9-fluorenon-3-yl]-6-(1R-hydroxyethyl)carbapen-2-em-3-carboxylate Substituting the 7-hydroxymethyl-9-fluorenone of Example 4 and following the procedure of Example 21 one can obtain the named compound.

EXAMPLE 23

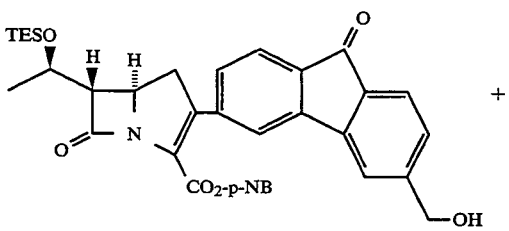

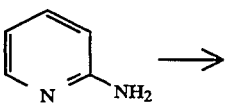

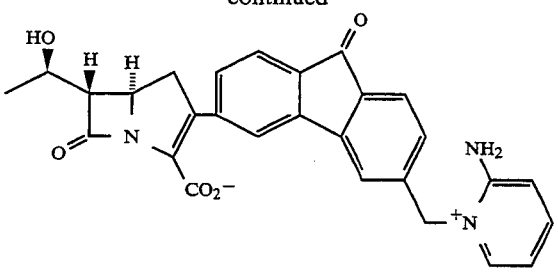

(5R,6S)-2-[6-(2-aminopyridinium)methyl-9-fluorenon-3-yl]-6-(1R-hydroxyethyl)carbapen-2-em-3-carboxylate Substituting the 6-hydroxymethyl-9-fluorenone of Example 5 and following the procedure of Example 21 one can obtain the named compound.

EXAMPLE 24

3-Bromo-9-fluorenone-1carboxylic acid

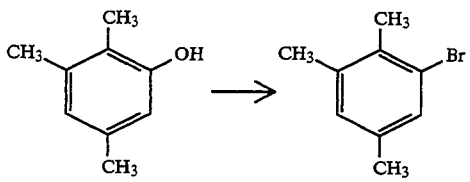

Step A: Preparation of 1-Bromo-2,3,5-trimethylbenzene

Triphenylphosphine 57.6 g was suspended in 50 ml CH₃CN and cooled to 0° under nitrogen. Bromine 11.2 ml (35.2 g) in 60 ml CH₃CN was added dropwise over 0.5 hour. The ice bath was removed and 27.2 g of the phenol in 40 ml CH₃CN was added all at once. The reaction mixture was heated to 60°-70° for 30 minutes, the solids went into solution. The acetonitrile was distilled off under house vac while the oil bath temperature was raised to 110°. When CH₃CN stopped distilling the reaction flask was fitted with a wide bore glass tubing, the top of which was connected by rubber tubing to a 500 ml 3 neck flask filled with 200 ml H₂O, one neck was stoppered and the other neck was connected to a nitrogen bubbler. The reaction mixture was heated in a sand bath to 340° for 4 hours. After a short while, a liquid started to reflux in the glass tubing. The glass tubing was replaced with a distillation unit and the liquid in the flask was distilled off at a boiling point of about 190° using the line vacuum. The distillation gave 22 g of desired product. Care should be taken to turn the vacuum on gradually as the high sand bath temperature will make the liquid flash out, a high temperature was required to get most of the product from the pot residue which was molten triphenylphosphine oxide.

¹H-NMR (CDCl₃, 200 MHz): δ2.25, 2.28, 3.01 (3 s, CH₃—Ar): 6.88, 7.21 (2s, ArH).

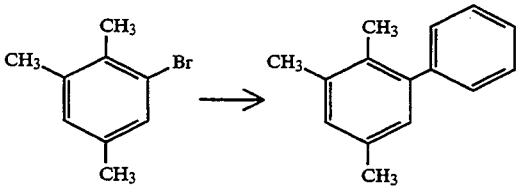

Step B: Preparation of 1-Phenyl-2,3,5-trimethylbenzene

The bromo compound 5 g was treated with 4.6 g $C_6H_5B(OH)_2$, 50 ml toluene, 25 ml $Na_2CO_3$ (2M), 12.5 ml MeOH and 0.21 g tetrakis(triphenylphosphine)palladium. The reaction mixture was heated under nitrogen overnight and worked up by extraction with ether, washing with water, sat'd. NaCl and drying and evaporation. The dark brown residue was passed through silica gel (120 g) using hexane as eluant. The hexane eluant after evaporation gave 4.5 g product.

$^1$H-NMR (CDCl$_3$, 200 MHz): δ2.17 (s, Ar—CH$_3$); 2.33 (s, 2s, Ar—CH$_3$); 6.92 (s, Ar—H); 7.01 (s, Ar—H); 7.2–7.5 (m, Ar—H).

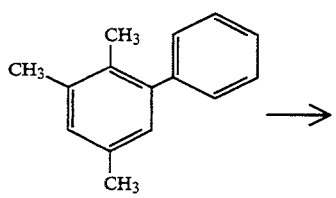

Step C: Preparation of 1-phenyl-benzene-2,3,5-tricarboxylic acid

The trimethylbiphenyl 18 g was suspended in 1.8 L of water, KMnO$_4$ (103 g) was added followed by 14.2 g Na$_2$CO$_3$. The reaction was refluxed gently overnight. The KMnO$_4$ was completely reacted but an oil was still floating on the surface (unreacted starting material). The solution was filtered and the residue (MnO$_2$) was washed with water. The filtrate and washings are extracted with ether. The aqueous phase was acidified and extracted with EtOAc 3×300 ml. The EtOAc extract was dried and evaporated which gave 11.5 of triacid.

From the ether extract after drying and evaporation, 4.8 g of s.m. was recovered.

$^1$H-NMR (D$_2$O, NaOD, 200 MHz): δ7.23 (m, Ar—H); 7.78 (s, Ar—H); 7.95 (s, Ar—H).

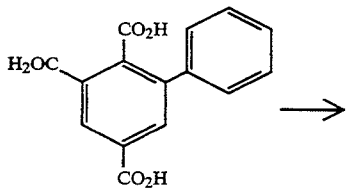

Step D: Preparation of 1-phenyl-benzene-2,3,5-tricarboxylic acid 2,3-anhydride The triacid 11.5 g was heated at 230° under line vac for 1 hour, allowed to cool to r.t. which gave the anhydride.

$^1$H-NMR (CD$_3$COCD$_3$, 200 MHz): δ7.34 (m, Ar—H); 7.72 (m, Ar—H); 8.46 (s, Ar—H); 8.49 (s, Ar—H). IR (neat, cm$^{-1}$) 1830, 1782, 1705.

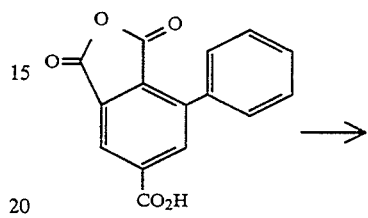

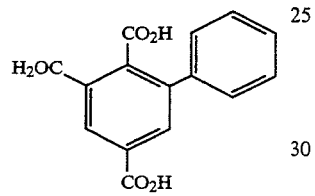

Step E: Preparation of 1-Phenyl-5-bromobenzene-2,3-dicarboxylic acid

1-Phenylbenzene-2,3,5-tricarboxylic acid 2,3-anhydride 4.2 g was suspended in 200 ml CH$_2$Cl$_2$, under N$_2$ and treated with 15.7 ml of a 2M solution of oxalyl chloride in CH$_2$Cl$_2$. Dimethylformamide 0.2 ml was added and the mixture allowed to stir at room temperature for three hours during which the original solid dissolved and a new solid precipitated out. The solvent and excess oxalyl chloride were evaporated off under reduced pressure which gave the acid chloride. This was suspended in BrCCl$_3$ (20 ml) and heated under N$_2$ to 100°. A solution of 2-mercaptopyridine-N-oxide (2.5 g) and azobisisobutyronitrile (1.4 g) in 2 ml CH$_2$Cl$_2$, and pyridine 1.24 ml in 25 ml BrCCl$_3$, was added dropwise over 0.5 hour and heating was continued another 0.5 hour. The reaction mixture was cooled and evaporated to remove the BrCCl$_3$ and the residue was stirred with excess 2N NaOH for 10 minutes. The basic solution was extracted twice with ether, then acidified and extracted again with EtOAc. The second EtOAc extract was dried and evaporated which gave a solid mixture of acids. Extraction with hot CHCl$_3$ gave the desired product 1.22 g. The CHCl$_3$ insoluble material was 1-phenylbenzene-2,3,5-tricarboxylic acid (3.2 g).

$^1$H-NMR (CDCl$_3$, 200 MHz): δ7.36 (broad s, Ar—H); 7.7 (s, Ar—H); 8.13 (s, Ar—H).

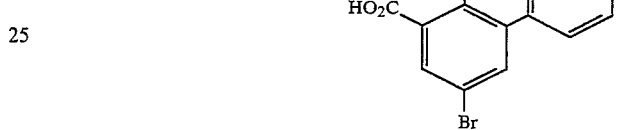

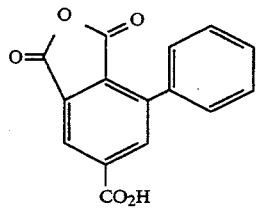

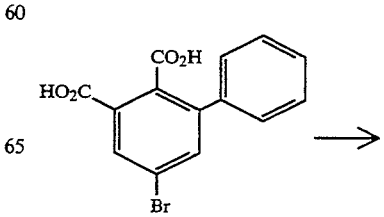

Step F: Preparation of 3-bromo-9-fluorenone-1-carboxylic acid

1-Phenyl-5-bromobenzene-2,3-dicarboxylic acid (1.2 g) was dissolved in H₂SO₄ (20 ml) and heated at 40° for 6 hours. The solution was cooled and added to ice (50 g). The precipitated yellow product was filtered and washed with water and air dried. The filtrate and washings were extracted with CH₂Cl₂ and washed once with saturated NaCl solution, then dried and evaporated which gave more of the product. Total yield 0.84 g.

¹H-NMR (CDCl₃, 200 MHz): δ7.3–7.8 (m, Ar—H); 7.84 (s, Ar—H); 8.33 (s, Ar—H).

EXAMPLE 25

3-Methoxycarbonyl-9-fluorenone-1-carboxylic acid

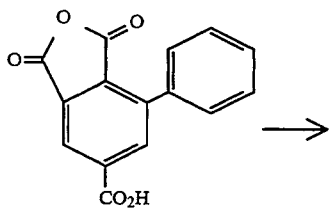

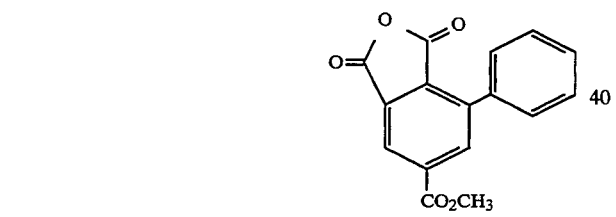

Step A: Preparation of 1-phenylbenzene-2,3,5-tricarboxylic acid-2,3-anhydride-5-methyl-ester The product from Step D, Example 24 was dissolved in 1:1 Et₂O/CH₂Cl₂ 200 ml (not completely dissolved). This solution was cooled to 0° and treated with a solution of diazomethane prepared from 20 g of N-nitrosomethylurea in 200 ml of Et₂O.

After addition the reaction mixture was stirred until N₂ evolution ceases and a yellow color persisted in the reaction mixture. The solution was full of crystals at this point. Excess diazomethane was removed by blowing N₂ through the mixture and the crystals are filtered off and washed with a little ether and dried by suction which gave 6.1 g of product. The filtrate was evaporated to dryness and the residue triturated with ether and cooled to 0° and filtered which gave a further 2.5 g of slightly yellow crystals which was also the desired product.

¹H-NMR (CDCl₃, 200 MHz): δ4.03 (s, O—CH₃); 7.54 (m, Ar—H); 8.5 (s, Ar—H); 8.59 (s, Ar—H).

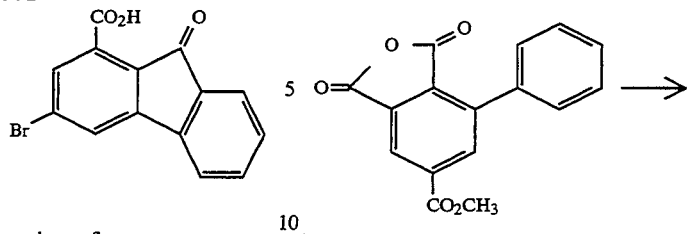

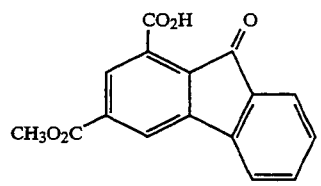

Step B: Preparation of 3-methoxycarbonyl-9-fluorenone-1-carboxylic acid

The 1-phenylbenzene-2,3,5-tricarboxylic acid-2,3-anhydride-5-methyl-ester (4 g) was dissolved in 80 ml of conc H₂SO₄ and heated to 40° C. for 6 hours. The reaction mixture was cooled and added to solid ice 400 g. The yellow precipitate was filtered (very slow filtration) and washed with a little water. The wet cake was dissolved in THF 100 ml and diluted with 400 ml of CH₂Cl₂. The solution was washed with brine, dried over MgSO₄ and evaporated to a small volume, which gave the desired product which crystalizes out during the evaporation. The product was filtered and dried which gave 3.6 g of yellow product.

¹H-NMR (CDCl₃, 200 MHz): δ4.02 (s, O—CH₃); 7.3–7.85 (m, Ar—H); 8.34 (s, Ar—H); 8.81 (s, Ar—H).

EXAMPLE 26

3-Bromo-1-hydroxymethyl-9-fluorenone

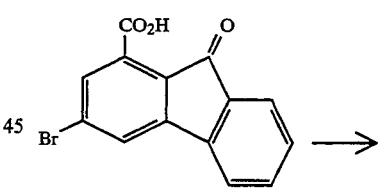

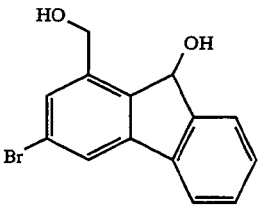

Step A: Preparation of 3-bromo-1-hydroxymethyl-9-fluorenol

3-Bromo-9-fluorenone-1-carboxylic acid (1.23 g) was dissolved in 20 ml THF and treated with BH₃. THF (8 ml, 1M soln in THF, 2 eq). The reaction mixture was allowed to stir overnight at room temperature under N₂. Hydrochloric acid (2N soln) was added and stirring continued until H₂ evolution ceased. The reaction mixture was diluted with water and extracted with EtOAc, dried and evaporated which gave the solid product (1.23 g), which was used without further purification in the next step.

$^1$H-NMR (CDCl$_3$, 200 MHz): δ4.71, 4.98 (2d, J=12, Ar—CH$_2$OH); 5.73 (s, ArCHOHAr); 7.3–7.8 (m, Ar—H).

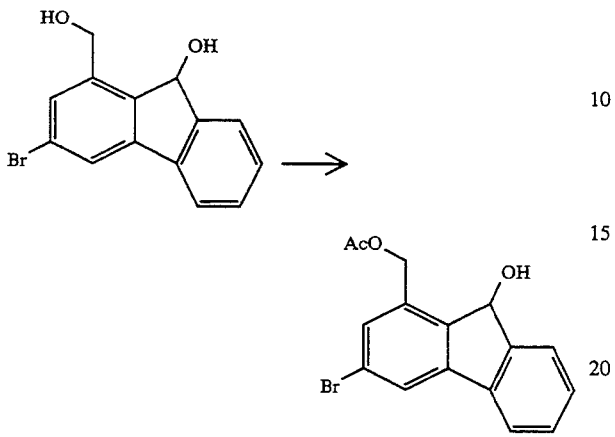

Step B: Preparation of 3-bromo-1-acetoxymethyl-9-fluorenol

3-Bromo-1-hydroxymethyl-9-fluorenol (1.23 g) was dissolved in pyridine (5 ml) and treated with Ac$_2$O (1.1 eq). The reaction mixture was allowed to stir at r.t. for 1 hour. The pyridine was evaporated off under reduced pressure, the residue dissolved in EtOAc, washed with 1N HCl followed by NaHCO$_3$ (10% sol'n) then dried and evaporated which gave the crude product which on chromatography on silicagel gave the desired product (0.406 g) along with starting material (0.252 g) and 3-bromo-1-acetoxymethyl-9-acetoxyfluorene (0.406 g).

$^1$H-NMR (CDCl$_3$, 200 MHz): δ2.16 (s, CH$_3$—C=O); 5.30, 5.44 (2d, J=14, Ar—CH$_2$O—); 5.68 (s, ArCHO-HAr); 7.3–7.8 (m, Ar—H).

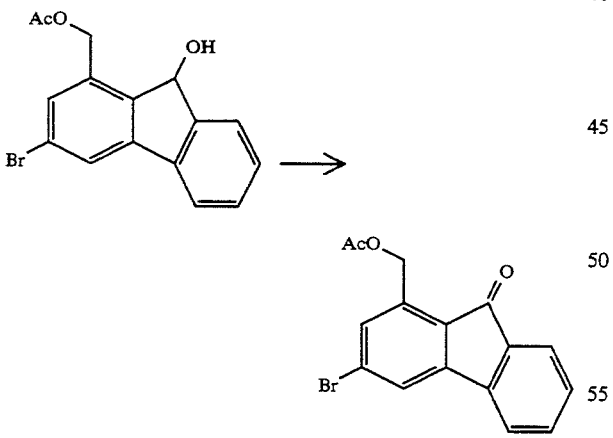

Step C: Preparation of 3-bromo-1-acetoxymethyl-9-fluorenone

Dichloromethane (5 ml) was cooled to −60° under N$_2$, oxalyl chloride (1.65 ml, 1M solution in CH$_2$Cl$_2$, 1.1 eq) was added followed by DMSO (234 ml in 1 ml of CH$_2$Cl$_2$). The resulting solution was stirred at −60° for 10 min. The 3-bromo-1-acetoxymethyl-9-fluorenol (0.480 g) in a suspension of CH$_2$Cl$_2$ (2 ml) was added dropwise and the solution stirred at −60° for 0.5 hour. Et$_3$N (1.06 ml) was added dropwise and the solution stirred at −60° for 15 minutes. The cooling bath was removed and water (5 ml) was added and the reaction mixture stirred at room temperature for 20 minutes. The organic phase was separated and the aqueous phase was extracted with EtOAc; the combined extract was dried without further purification in the next step.

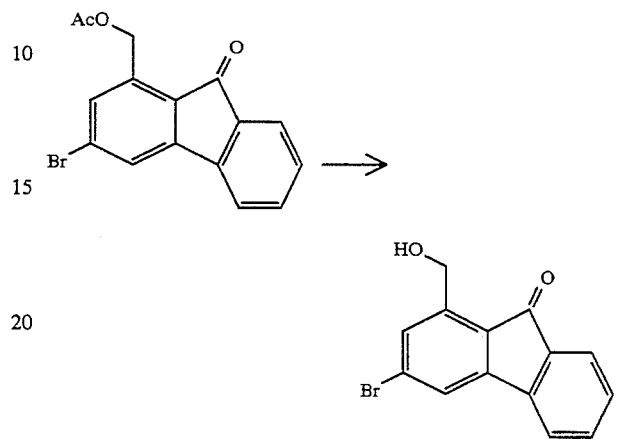

Step D: Preparation of 3-bromo-1-hydroxymethyl-9-fluorenone

The product from the previous reaction was dissolved in MeOH (5 ml) and treated with NaOMe (0.054 ml, 5.5M soln in MeOH, 0.2 eq). The mixture was allowed to stir at r.t. for 1 hour. The Methanol was removed under reduced pressure and the residue was taken up in EtOAc and washed with pH 7 buffer, water and sat'd NaCl sol'n, dried and evaporated which gave crude product 0.396 g. Purification by preparative tlc (20% EtOAc/hexane elution) gave pure product (0.289 g).

$^1$H-NMR (CDCl$_3$, 200 MHz): δ4.01 (t, J=6, OH); 4.86 (d, J=6, Ar—CH$_2$OH); 7.3–7.8 (m, Ar—H).

EXAMPLE 27

1-hydroxymethyl-3-methylcarbonyl-9-fluorenone

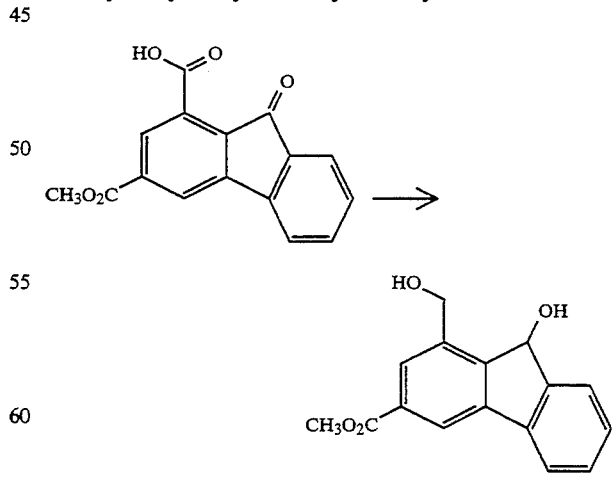

Step A: Preparation of 3-methoxycarbonyl-1-hydroxymethyl-9-fluorenol

3-Methoxycarbonyl-9-fluorenone-1-carboxylic acid (0.75 g), from Step B of Example 25 was reduced following the procedure of Example 26, Step A, which gave the product (0.74 g).

¹H-NMR (CDCl₃, 200 MHz): δ3.80 (s, OCH₃); 4.64, 4.94 (2d, J=14, ArCH₂OH); 5.63 (s, ArCHOHAr); 7.2–7.68 (m, Ar—H); 7.71 (s, ArH); 8.03 (s, ArH).

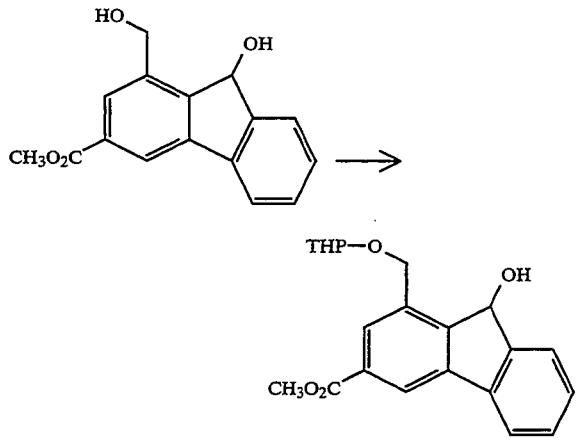

Step B: Preparation of 3-methoxycarbonyl-1-(2-tetrahydropyranyl)oxymethyl-9-fluorenol 3-Methoxycarbonyl-1-hydroxymethyl-9-fluorenol (0.96 g) was treated with dihydropyran (0.43 ml) and p-toluenesulfonic acid (20 mg) in CH₂Cl₂ (20 ml) for 0.5 hour. The reaction mixture was washed once with NaHCO₃ (10% soln) then dried and evaporated which gave a mixture of products. Chromatography on silica gel using EtOAc/hexane 1:1 as eluant gave the product (403 mg).

¹H-NMR (CDCl₃, 200 MHz): δ1.4–2.0 (m, CH₂—CH₂—CH₂—); 3.6 (m, CH₂—CH₂O); 3.94 (s, OCH₃); 4.76 (m, ARCH₂O); 5.12 (t, OCHO); 5.8 (m, ArCHOHAr ); 7.2–8.3 (m, Ar—H).

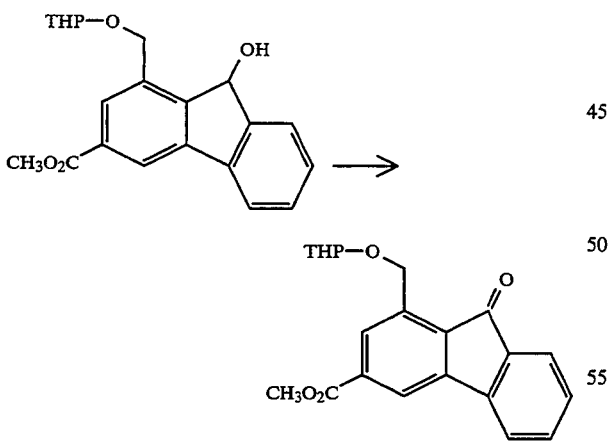

Step C: Preparation of 3-methoxycarbonyl-1-(2-tetrahydropyranyl)oxymethyl-9-fluorenone 3-Methoxycarbonyl-1-(2-tetrahydropyranyl)oxymethyl-9-fluorenol (403 mg) was oxidized under the conditions described in Example 24, Step C, which gave the product.

¹H-NMR (CDCl₃, 200 MHz): δ1.4–2.0 (m, CH₂—CH₂—CH₂); 3.6 (m, CH₂—CH₂O); 3.96 (s, OCH₃): 4.82 (t, OCHO); 5.04, 5.2 (2d, J=13, ArCH₂O); 7.2–7.8 (m, Ar—H): 8.05 (s, ArH); 8.16 (s, ArH). IR (neat, cm⁻¹): 1760, 1712.

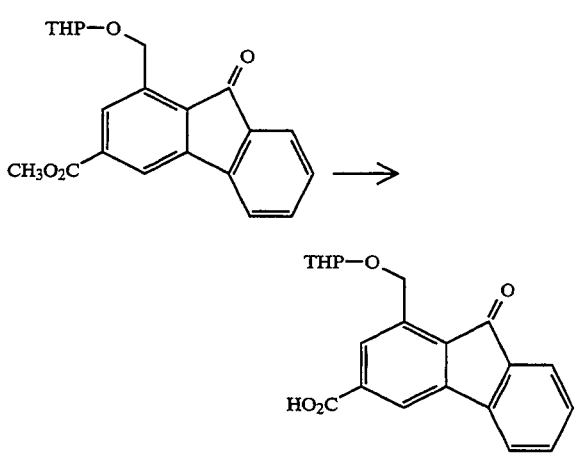

Step D: Preparation of 1-(2-tetrahydropyranyl)oxymethyl-9-fluorenone-3-carboxylic acid 3-Methoxycarbonyl-1-(2-tetrahydropyranyl)oxy methyl-9-fluorenone from the previous reaction was dissolved in MeOH (20 ml) and water (10 ml) and treated with NaOH (2 eq). The reaction mixture was heated in an oil bath at 80° for 1 hr. The reaction mixture was cooled and the MeOH was removed under reduced pressure. The residue was diluted with water and extracted once with EtOAc, then acidified and extracted once with EtOAc. The second EtOAc extract was dried and evaporated which gave the desired acid (275 mg).

¹H-NMR (CDCl₃, 200 MHz): δ1.4–2.0 (m, CH₂—CH₂—CH₂); 3.6, 3.95 (2 m, CH₂—CH₂O); 4.87 (t, OCHO): 5.04, 5.22 (2d, J=13, ArCH₂O); 7.2–7.7 (m, Ar—H): 8.08 (s, ArH): 8.15 (s, ArH).

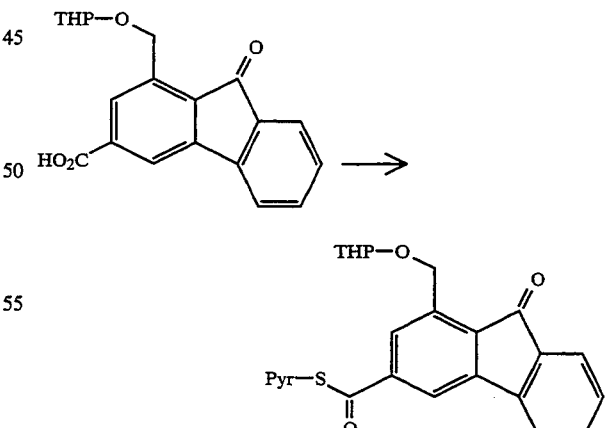

Step E: Preparation of 1-(2-tetrahydropyranyl)oxymethyl-3-(2-pyridyl)-thiocarbonyl-9-fluorenone 1-(2-Tetrahydropyranyl)oxymethyl-9-fluorenone -3-carboxylic acid (57 mg) was dissolved in THF (2 ml). Triphenylphosphine (46.4 mg) and 2,2'-dipyridyl disulfide (39 mg) were added and the reaction mixture was stirred for 2 hours at room temperature Triphenylphosphine (23.3 mg) and 2,2'-dipyridyl disulfide (20 mg) were again added and the reaction mixture stirred another 2 hours. The reaction mixture was evaporated to dryness and the residue purified by preparative tlc on silica gel using EtOAc/hexane 1:1 as eluant which gave the product (76 mg).

$^1$H-NMR (CDCl$_3$, 200 MHz): δ1.4–2.0 (m, CH$_2$—CH$_2$—CH$_2$); 3.6, 3.95 (2 m, CH$_2$—CH$_2$O): 4.87 (t, OCHO): 5.1, 5.25 (2d, J=15, ArCH$_2$O); 7.0–8.8 (m, Ar—H and pyridyl-H).

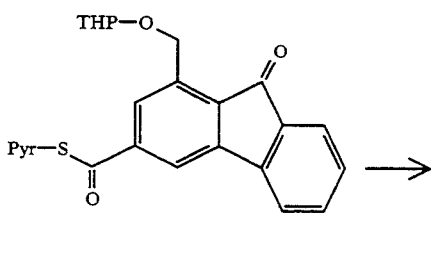

Step F: Preparation of 1-(2-tetrahydropyranyl)oxymethyl-3-methylcarbonyl-9-fluorenone 1-(2-Tetrahydropyranyl)oxymethyl-3-(2-pyridyl)thiocarbonyl-9-fluorenone (470 mg) was dissolved in THF (10 ml) and cooled to −15° under N$_2$. A solution of MeMgBr in THF (1.2 eq) was added dropwise over 5 min and the reaction allowed to stir at −10° C. for 0.5 hr. The reaction was quenched with saturated ammonium chloride solution, diluted with EtOAc, and washed with water, sat'd NaCl sol'n then dried and evaporated which gave a residue which was chromatographed on silica gel to give the product (233 mg).

$^1$H-NMR (CDCl$_3$, 200 MHz): δ1.4–2.0 (m, CH$_2$—CH$_2$—CH$_2$); 2.67 (s, CH$_3$CO): 3.6, 3.95 (2 m, CH$_2$—CH$_2$O); 4.82 (t, OCHO); 5.06, 5.22 (2d, J=17, ArCH$_2$O); 7.2–7.7 (M, Ar—H); 7.98 (s, ArH); 8.06 (s, ArH).

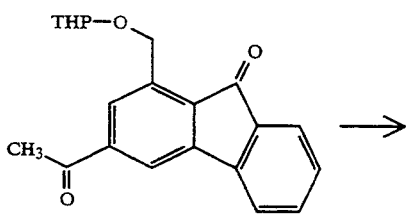

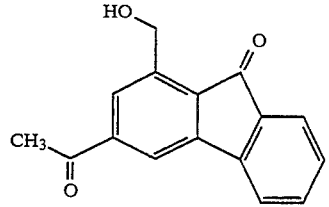

Step G: Preparation of 1-hydroxymethyl-3-methylcarbonyl-9-fluorenone 1-(2-Tetrahydropyranyl)oxymethyl-3-methylcarbonyl-9-fluorenone (197 mg) was dissolved in 1% H$_2$SO$_4$ (5 ml) and allowed to stand at room temperature for 0.5 hr. The reaction mixture was diluted with excess NaHCO$_3$ soln (10%). The MeOH was removed under reduced pressure and the residue was extracted with EtOAc, dried and evaporated which gave the product (135 mg).

$^1$H-NMR (CDCl$_3$, 200 MHz): δ2.67 (s, CH$_3$CO); 4.96 (ArCH$_2$OH); 7.2–7.72 (m, Ar—H); 7.8 (s, ArH); 7.98 (s, ArH). IR (neat, cm$^{-1}$): 1710, 1690.

EXAMPLE 28

Sodium (5R,6S)-2-(9-fluorenon-2-yl)-6-(1R-hydroxyethyl)carbapen-2-em-3-carboxylate

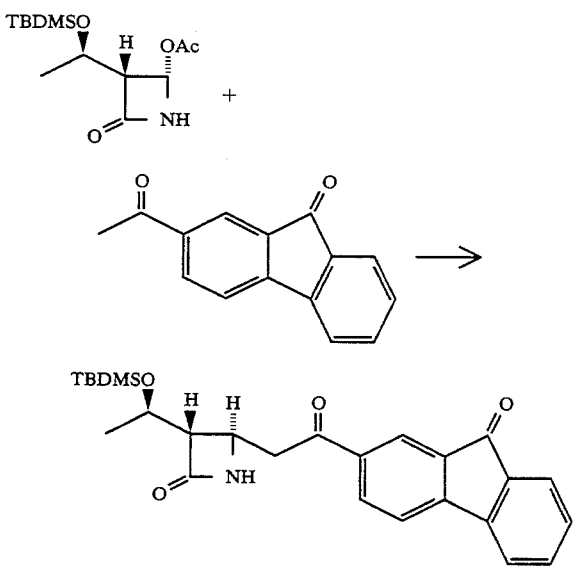

Step A: Preparation of 3-(1-R-t-butyldimethylsilyloxyethyl)-4-[2-(9-fluorenon-2-yl)-2-oxo]ethylazetidin-2-one 2-Acetyl-9-fluorenone (644 mg) was dissolved in 20 ml methylene chloride, and (3S,4S)-3-(1R-t-butyldimethylsilyloxyethyl)-4-acetoxyazetidin-2-one (880 mg) was added and the mixture was cooled to 0° C. under nitrogen. Triethylamine (1.12 ml) was added followed by trimethylsilyl triflate (1.42 ml). The reaction mixture was stirred at 0° for 15 minutes and allowed to come to room temperature. Trimethylsilyl triflate (0.204 ml) was added and the mixture was stirred at room temperature for 1 hour. The reaction mixture was diluted with methylene chloride and washed with 10% sodium bicarbonate solution, dried over magnesium sulfate and evaporated gave the crude product, chromatography on silica gel using 50% EtOAc/hexane gave the desired product (304 mg).

¹H-NMR (CDCl₃, 200 MHz): δ0.06 (s, Me₃Si); 0.84 (s, Me₃C—Si); 1.23 (d, J=7, CH₃—C); 2.89 (d of d, J=5, J=2, C-3H); 3.16 (d of d, J=4.5, J=2.5, CH₂—C=O); 3.48 (d of d, J=4.5, J=1, CH₂—C=O); 4.16 (m, C-4H and CH₃—CH—); 6.15 (s, NH), 7.25-8.2 (m, ArH). IR (neat, cm⁻¹) 3340 (NH), 1755 (β-lactam), 1718 and 1680 (ketones).

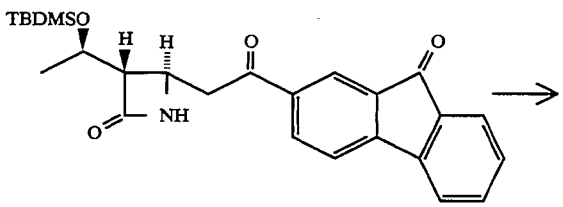

Step B: Preparation of (3S,4R)-1-(Allyloxycarbonyl)hydroxymethyl-3-(1R-t-butyldimethylsilyloxyethyl)-4-[2-(9-fluroenon-2-yl)-2-oxo]ethylazetidin-2-one The product from the previous reaction (304 mg) was dissolved in methylene chloride (12 ml) and treated with allyl glyoxalate hydrate (154 mg) and triethylamine (188 ml), MgSO₄ (3 g) was added and the mixture was allowed to stir overnight at room temperature. The MgSO₄ was filtered off and the filtrate was evaporated and chromatographed on silica gel gave the product (98 mg).

IR (neat, cm⁻¹) 3400 (NH and OH), 1755 (β-lactam), 1718 and 1680.

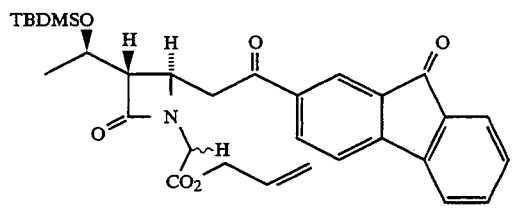

Step C: Preparation of (3S,4R)-1-(Allyloxycarbonyl)triphenylphosphoranylidene-methyl-3-(1R-t-butyldimethylsilyloxyethyl)-4-[2-(9-fluorenon-2-yl)-2-oxo]ethylazetidin-2-one The product from the previous reaction (8 mg) was dissolved in 1 ml THF and cooled to −10° under nitrogen. 2,6-Lutidine (25 ml) was added followed by SOCl₂ (15.5 ml). The reaction mixture was stirred for 1.5 hours during which the temperature reached 0° C. The solution was filtered and the filtrate was evaporated to dryness, the residue was taken up in DMF (1 ml) under nitrogen and treated with triphenylphosphine (54.7 mg). The reaction mixture was allowed to stir at room temperature for 3 hours. The reaction was diluted with EtOAc and washed with 10% NaHCO₃ solution, dried and evaporated and the residual DMF was evaporated off by flushing with toluene twice. The residue was purified by preparative tlc and gave the product (56 mg).

IR (neat, cm⁻¹) 1740 (β-lactam), 1718 and 1678, 1610.

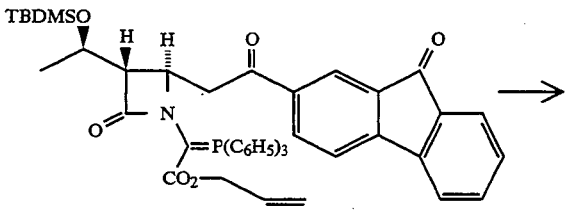

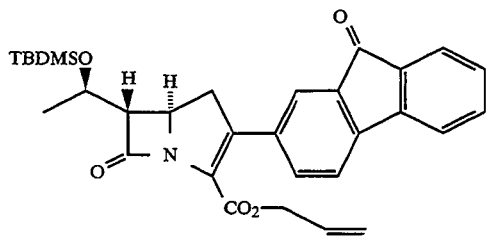

Step D: Preparation of Allyl (5R,6S)-2-(9-fluorenon-2-yl)-6-(1R-t-butyldimethylsilyloxyethyl)carbapen-2-em-3-carboxylate The product from the previous reaction (56 mg) was dissolved in xylenes (5 ml) and degassed by bubbling nitrogen for 5 minutes, the solution was heated under nitrogen for 1.5 hours at 130°. The solvent was removed under reduced pressure and the residue was purified by preparative tlc and gave the product (33 mg).

¹H-NMR (CDCl₃, 200 MHz): δ0.13 (s, Me₃Si); 0.93 (s, Me₃C—Si): 1.31 (d, J=7, CH₃—C); 3.25 (m, C-6H and C-1H); 4.25 (m, C-5H and CH₃—CH—); 4.5-6.0 (m, allyl H); 7.25-7.8 (m, ArH). IR (neat, cm⁻¹) 1775 (β-lactam), 1718.

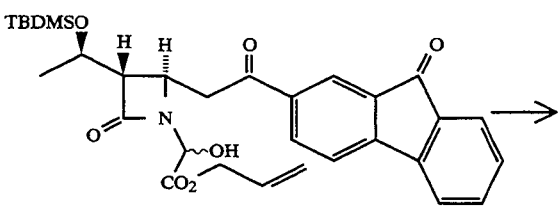

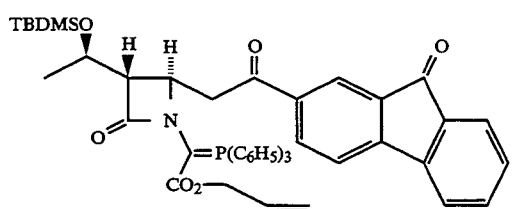

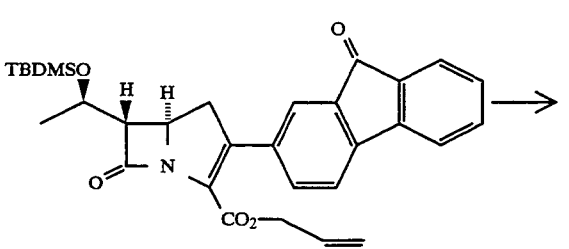

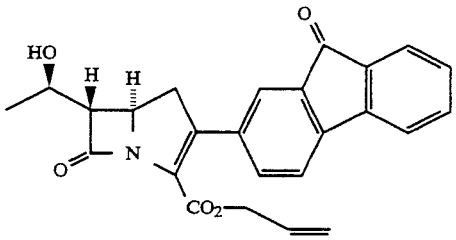

Step E: Preparation of Allyl (5R,6S)-2-(9-fluroenon-2-yl)-6-(1R-hydroxyethyl)-carbapen-2-em-3-carboxylate The product from the previous reaction (33 mg) was dissolved in THF (1 ml) and treated with acetic acid (47.6 μl) and n-Bu$_4$N$^+$F$^-$ (265 μl of a 1M solution in THF). The reaction mixture was stirred at room temperature overnight. The reaction mixture was diluted with EtOAc and washed with ice water, 10% NaHCO$_3$ solution and sat'd NaCl solution, dried and evaporated gave the crude product. Purification by preparative tlc gave the product (4 mg).

$^1$H-NMR (CDCl$_3$, 300 MHz): δ1.38 (d, J=7, CH$_3$—C); 3.28 (m, C-6H and C-1H); 4.25 (m, C-5H and CH$_3$—CH—); 4.5–6.0 (m, allyl H); 7.25–7.7 (m, ArH).

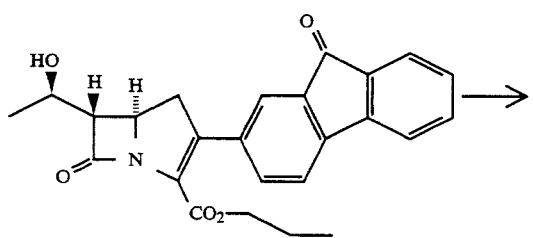

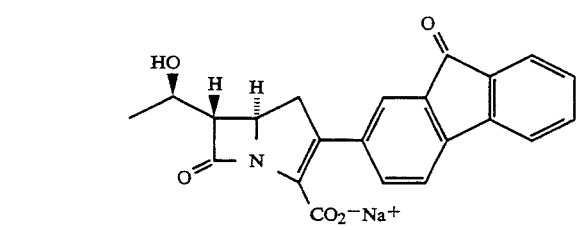

Step F: Preparation of Sodium (5R,6S)-2-(9-fluorenon-2-yl)-6-(1R-hydroxyethyl)-carbapen-2-em-3-carboxylate The product from the above reaction (4 mg) was dissolved in EtOAc (0.25 ml) and CH$_2$Cl$_2$ (0.25 ml). Sodium 2-ethylhexanoate (2.0 mg) was added followed by triphenylphosphine (1 mg) and tetrakis(triphenylphosphine)palladium(0) (1 mg). The reaction mixture was allowed to stir 15 minutes at room temperature then diluted with EtOAc (2 ml) and water (2 ml). After vigorous shaking, the layers are separated. The organic phase was extracted with water (2 ml) and the combined aqueous phase was evaporated to 1 ml and the product purified by reverse phase HPLC using CH$_3$CN/H$_2$O gradient elution, gave 2.3 mg of desired product.

$^1$H-NMR(H$_2$O, 300 MHz): δ1.42 (d, J=7, CH$_3$—C); 3.17 (d of d, J=16, J=9, C-1 Ha); 3.52 (d of d, J=16, J=8, C-1 Hb); 3.62 (d of d, J=6, J=2.5, C-6H); 4.4 (m, C-5H and CH$_3$—CH—); 7.3–7.6 (m, ArH). UV (H$_2$O, λmax): 255, 300, 340(s).

EXAMPLE 29

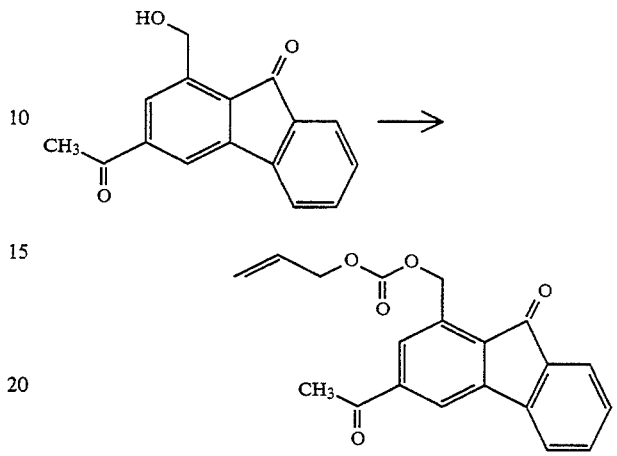

1-allyloxycarbonyloxymethyl-3-methylcarbonyl-9-fluorenone

1-Hydroxymethyl-3-methylcarbonyl-9-fluorenone (135 mg) was dissolved in THF (4 ml), cooled to 0° C. under N$_2$. Pyridine (51 μl, 1.2 eq) was added followed by allyloxycarbonyl chloride (70 μl, 1.2 eq). The reaction mixture was allowed to stir overnight allowing it to come to room temperature. The reaction mixture was diluted with methylene chloride, washed with water, sat'd NaCl sol'n, dried and evaporated. The product was purified by preparative tlc (80 mg).

$^1$H-NMR (CDCl$_3$, 200 MHz): δ2.64 (s, CH$_3$CO); 4.68 (d, CH$_2$=CHCH$_2$O); 5.35 (m, CH$_2$=); 5.68 (s, ArCH$_2$OH); 7.2–7.7 (m, Ar—H); 7.86 (s, ArH); 7.99 (s, ArH). IR (neat, cm$^{-1}$): 1750, 1715, 1695.

EXAMPLE 30

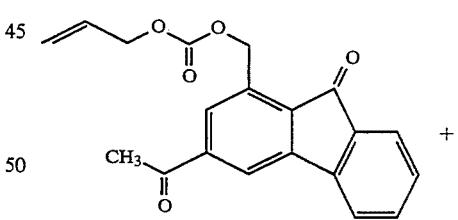

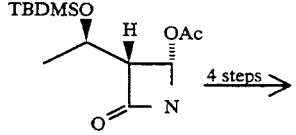

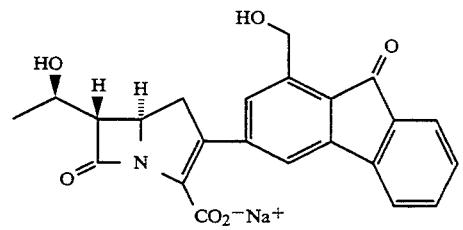

Sodium (5R,6S)-2-(1-hydroxymethyl-9-fluorenone-3-yl)-6-(1R-hydroxyethyl)carbapen-2-em-3-carboxylate Starting with the product of Example 29 and following Steps A–F Example 28 one obtains the desired product, identical with the product of Example 4. In Step F, 1 equivalent of 2-ethylhexanoic acid was also added to the reaction mixture.

EXAMPLE 31

3-Bromo-7-methyl-9-fluorenone

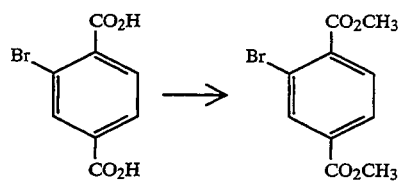

Step A: Preparation of Dimethyl-2-bromoterephthlate

2-Bromoterephthalic acid (14.2 g) was treated with thionyl chloride (35 ml) and the reaction mixture was heated at reflux overnight. The reaction mixture was cooled and the excess $SOCl_2$ was removed under reduced pressure. The residue was treated with methanol (174 ml) at $-10°$ C. over a one-half hour period followed by triethylamine (17.4 ml). After 15 minutes at room temperature, the methanol was removed under reduced pressure. The residue was then taken up in ethyl ether, washed with water, dried and evaporated which gave a white solid (14.65 g).

$^1$H-NMR (CDCl$_3$, 200 MHz): δ3.87 (s, CH$_3$); 7.8–8.32 (m, ArH). IR (CH$_2$Cl$_2$, cm$^{-1}$): 1720.

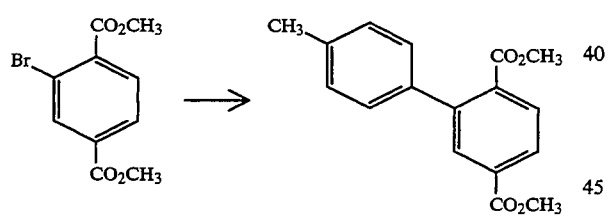

Step B: Preparation of Dimethyl-2-(4-toluyl)terephthalate

4-Bromotoluene (6 g) was dissolved in tetrahydrofuran (20 ml). To this solution at $-78°$ C. under N$_2$ was added over a ten minute period, 1.7M tBuLi (42 ml). After two hours at room temperature, the reaction mixture was cooled to 0° C. and 1M ZnCl$_2$ (36 ml) was added over a ten minute period. After one-half hour at room temperature, bis(triphenylphosphine)nickel(II) chloride (1.32 g) was added followed by dimethyl-2-bromo-terephthalate (6 g) in tetrahydrofuran 920 ml) dropwise over a five minute period. The reaction mixture was stirred at room temperature for two hours. The tetrahydrofuran was removed under reduced pressure. The residue was treated with ethyl acetate and 1N HCl and the layers separated. The organic phase was washed with water, brine, dried over magnesium sulfate and evaporated which gave the crude product. Chromatography on silica gel using 5% hexanes/methylene chloride gave the desired product (5.33 g).

$^1$H-NMR (CDCl$_3$, 200 MHz): δ2.42 (s, CH$_3$); 3.71, 3.96 (2s, CH$_3$O); 7.24–8.11 (m, ArH). IR (CH$_2$Cl$_2$, cm$^{-1}$): 1720.

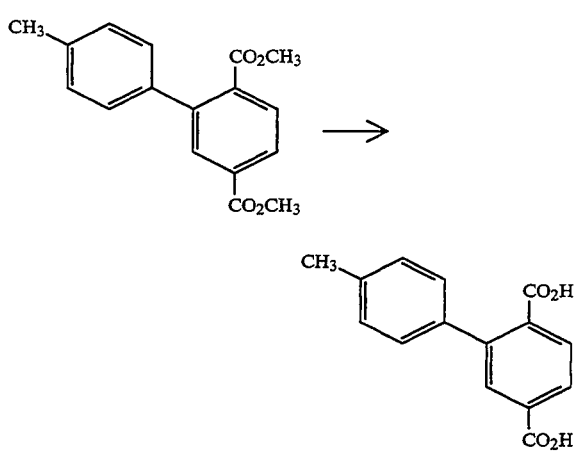

Step C: Preparation of 2-(4-toluyl)terephthalic acid

Dimethyl2-(4-tolyl)terephthalate (11.88 g) was suspended in methanol (99 ml). 5M NaOH (50 ml) was added. The reaction mixture was heated at reflux for 1.5 hours. The methanol was removed under reduced pressure. The residue was treated with ethyl acetate and water and the layers separated. The aqueous layer was washed once with ethyl acetate. The aqueous layer was then acidified with 2N HCl and extracted three times with ethyl acetate. These combined organic extracts were then dried over MgSO$_4$, filtered and evaporated under reduced pressure which gave the product (7.09 g).

$^1$H-NMR (DMSO, 200 MHz): δ2.34 (s, CH$_3$); 7.24–8.08 (m, ArH).

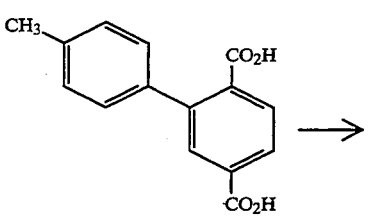

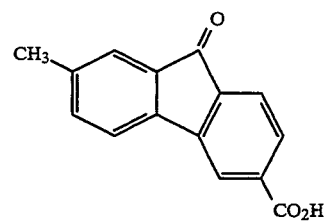

Step D: Preparation of 7-methyl-9-fluorenone-3-carboxylic acid 2-(4-Tolyl)terephthalic acid (7 g) at 0° C. was suspended in concentrated H$_2$SO$_4$ (41 ml). The reaction mixture was heated at 40° C. for four hours (a black solution develops). Ice was added to the reaction mixture and the precipitated yellow solid was filtered, washed well with water and dried under high vacuum. The filtrate was extracted three times with ethyl acetate. The combined organic layers were dried with MgSO4, filtered and evaporated under reduced pressure which gave the desired product as a yellow solid. This was combined with the precipitated yellow solid which gave 6.5 g of the desired product.

¹H-NMR (DMSO, 200 MHz ): δ2.33 (s, CH3); 7.42–8.21 (m, ArH).

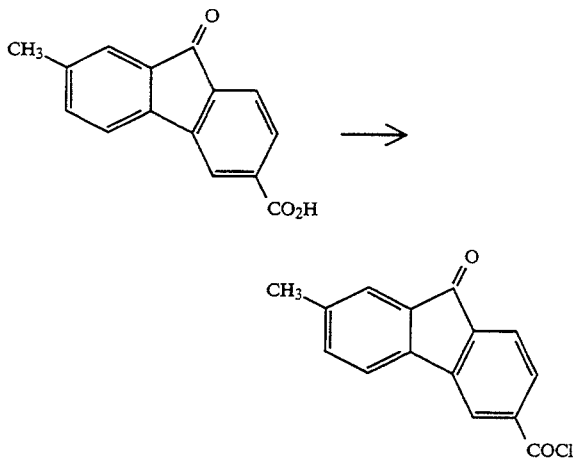

Step E: Preparation of 7-methyl-9-fluorenone-3-carboxylic acid chloride

7-Methyl-9-fluorenone-3-carboxylic acid (6.5 g) was suspended in methylene chloride (110 ml) at 0° C., 2M oxalyl chloride (30 ml) was added followed by DMF (1.17 ml added over a three hour period). The reaction mixture was stirred at room temperature for twenty hours. The reaction mixture was filtered and the methylene chloride was removed under reduced pressure which gave the crude product (7.0 g).

¹H-NMR (CDCl3, 200 MHz): δ2.42 (s, CH3); 7.38–8.41 (m, ArH).

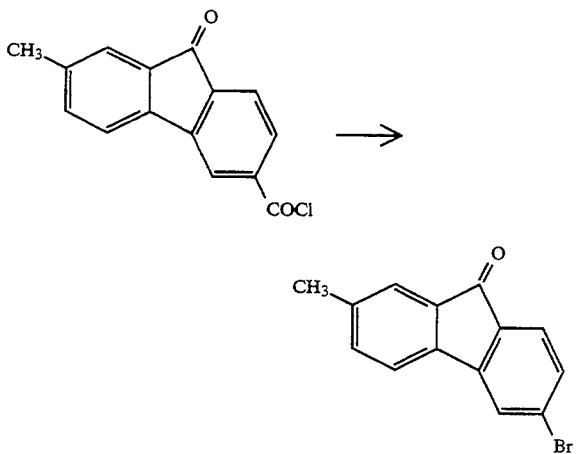

Step F: Preparation of 3-Bromo-7-methyl-9-fluorenone

7-Methyl-9-fluorenone-3-carboxylic acid chloride (7 g) was dissolved in BrCCl3 (130 ml), AIBN (2.33 g) in methylene chloride (20 ml) was added. This solution was then added dropwise over a 45 minute period to a suspension of the sodium salt of 2-mercaptopyridine-N-oxide (6.13 g) in BrCCl3 (70 ml) at 100° C. Additional AIBN (235 mg) in a minimum of methylene chloride was then added. The reaction mixture was stirred at 100° C. for twenty minutes, diluted with methylene chloride, washed with aqueous sodium bicarbonate, dried and evaporated. The residue was chromatographed on silica gel using 50% hexanes/methylene chloride which gave the desired product (2.9 g).

¹H-NMR (CDCl3, 200 MHz): δ2.41 (s, CH3); 7.32–7.64 (m, ArH). IR (CH2Cl2, cm⁻¹): 1715.

EXAMPLE 32

3-Bromo-7-hydroxymethyl-9-fluorenone

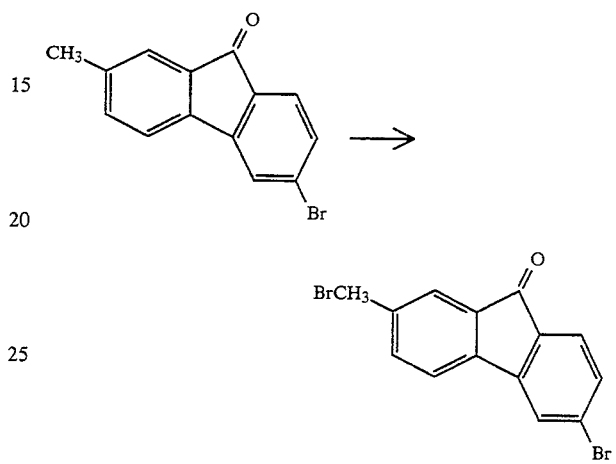

Step A: Preparation of 7-bromomethyl-3-bromo-9-fluorenone

3-Bromo-7-methyl-9-fluorenone (2.6 g) was dissolved in CCl4 (70 ml). To this solution at 80° C. was added NBS (1.78 g) and AIBN (260 mg). After one-half hour, additional AIBN (520 mg) was added. At fifteen hours, additional NBS (178 mg) was added. The reaction mixture was stirred at reflux for 22.5 hours. CCl4 was removed under reduced pressure. Residue was then diluted with ethyl acetate, washed twice with water, once with brine, dried and evaporated which gave the crude product. Crystallization from 50% ethyl acetate/hexanes gave the pure product (1.7 g) was well as a 1/1 mixture of 7-dibromomethyl-3-bromo-9-fluorenone and 7-bromomethyl-3-bromo-9-fluorenone (476 mg) in the mother liquors.

¹H-NMR (CDCl3, 200 MHz): δ4.52 (s, CH2Br); 7.44–7.68 (m, ArH). IR (CH2Cl2, cm⁻¹): 1720.

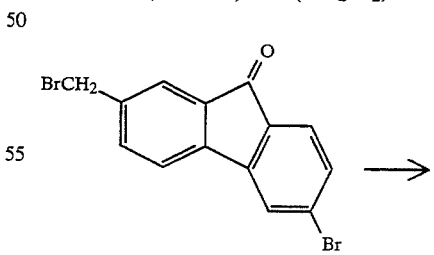

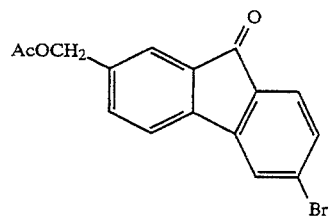

Step B: Preparation of 3-bromo-7-acetoxymethyl-9-fluorenone

7-Bromomethyl-3-bromo-9-fluorenone (1.7 g) was suspended in DMF (25 ml). To this suspension was added potassium acetate (576 mg). The reaction mixture was stirred at 100° C. for one hour. It was then diluted with ethyl acetate, washed four times with water, twice with brine, dried and evaporated. The residue was chromatographed on silica gel using 2% ethyl acetate/methylene chloride which gave the desired product (1.18 g).

$^1$H-NMR (CDCl$_3$, 200 MHz): δ2.12 (s, CH$_3$—C=O); 7.42–7.68 (m, ArH). IR (CH$_2$Cl$_2$, cm$^{-1}$): 1720.

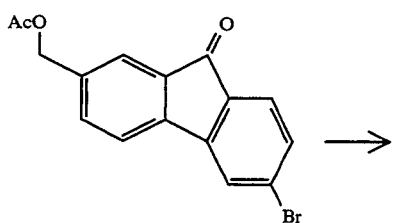

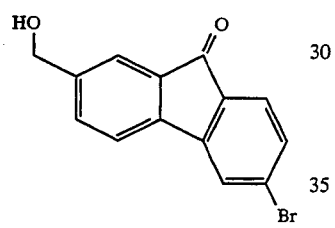

Step C: Preparation of 3-bromo-7-hydroxymethyl-9-fluorenone

3-Bromo-7-acetoxymethyl-9-fluorenone (1.18 g) was suspended in methanol (102 ml) and THF (23 ml). To this suspension was added 0.054M NaOMe (6.6 ml). The reaction mixture was stirred at room temperature for 1.25 hours. It was then neutralized with 0.2M pH 7 phosphate buffer. The tetrahydrofuran and methanol were removed under reduced pressure. Reaction mixture was then diluted with ethyl acetate, washed with water and brine, dried and evaporated which gave the product (1.0 g).

$^1$H-NMR (DMSO, 200 MHz): δ4.53 (d, J=6, CH$_2$OH); 5.35 (t, J=6, OH); 7.46–8.06 (m, ArH).

EXAMPLE 33

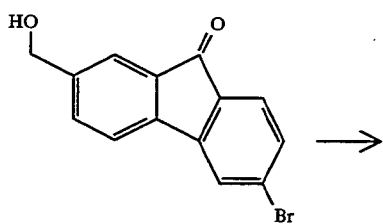

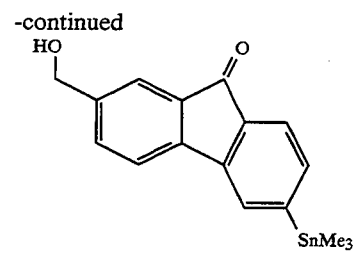

3-Trimethylstannyl-7-hydroxymethyl-9-fluorenone

3-Bromo-7-hydroxymethyl-9-fluorenone (200 mg) was dissolved in toluene (10 ml). Reaction mixture was then degassed by bubbling in nitrogen for five minutes. To this solution at 110° C. was added hexamethylditin (282 μl) and then tetrakis(triphenylphosphine)palladium(0) (47 mg) and triphenylphosphine (3.6 mg) in toluene (10 ml) dropwise over a five minutes period. Reaction mixture was stirred at 110° C. for five minutes. Toluene was removed under reduced pressure. The residue was purified by preparative tlc using 20% ethyl acetate/methylene chloride which gave the desired product (205 mg).

$^1$H-NMR (CDCl$_3$, 200 MHz): δ0.36 (s, SnMe$_3$); 1.8 (t, J=6, OH); 4.73 (d, J=6, CH$_2$OH); 7.42–7.65 (m, ArH). IR (CH$_2$Cl$_2$, cm$^{-1}$): 1713.

EXAMPLE 34

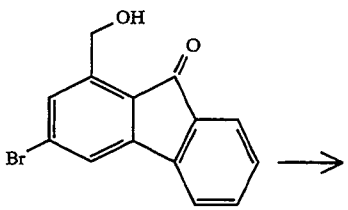

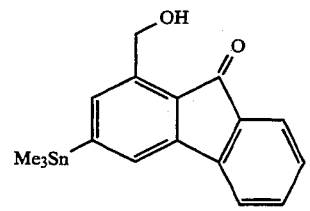

3-Trimethylstannyl-1-hydroxymethyl-9-fluorenone

3-Bromo-1-hydroxymethyl-9-fluorenone (289 mg) was dissolved in toluene (4 ml) and tetrakis(triphenylphosphine)palladium(0) (50 mg, 0.06 eq) and triphenylphosphine (3.8 mg, 0.02 eq) were added. The solution was then degassed by bubbling in nitrogen for five minutes and then treating with hexamethyldistannane (208 μl, 1.4 eq). The reaction mixture was stirred at 110° C. under N$_2$ for 1 hour. The toluene was removed under reduced pressure and the residue was purified by preparative tlc using 20% ethyl acetate/methylene chloride which gave the desired product (230 mg).

$^1$H-NMR (CDCl$_3$, 200 MHz): δ0.35 (s, SnMe$_3$); 4.32 (t, J=8, OH); 4.85 (d, J=8, Ar—CH$_2$OH); 7.2–7.7 (m, ArH).

What is claimed is:
1. A compound of formula

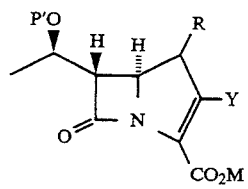

wherein: Y is

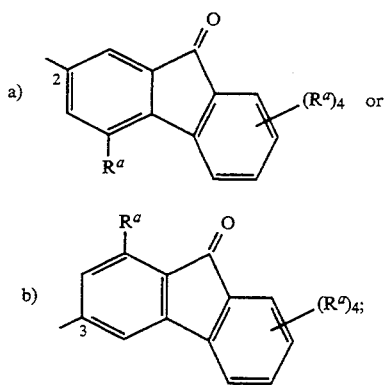

R is H or CH$_3$;

P' is a removable hydroxyl protecting group; each R$^a$ group is independently selected from the group consisting of hydrogen and the radicals set out below, provided that one R$^a$ is selected from Type I substitutents and zero to three R$^a$ radicals are selected from Type II substituents; wherein the Type I substituents are:

Type I.
a)

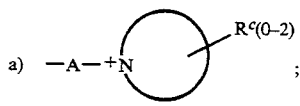

where

A is (CH$_2$)$_m$—Q—(CH$_2$)$_n$, where m is 0 to 6 and n is 1 to 6 and Q is a covalent bond, O, S, SO, SO$_2$, NH, —SO$_2$NH—, —NHSO$_2$—, —CONH—, —NHCO—, —SO$_2$N(C$_1$-C$_4$alkyl)—, —N(C$_1$-C$_4$alkyl)-SO$_2$—, —CON(C$_1$-C$_4$alkyl)—, —N(C$_1$-C$_4$alkyl)-CO—, —CH=CH—, —CO—, —OC(O)—, —C(O)O— or N(C$_1$-C$_4$alkyl) and (CH$_2$)$_m$ is attached to the fluoren-9-one moiety;

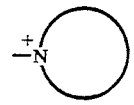

is a 5- or 6-membered monocyclic heterocycle or an 8-, 9- or 10-membered bicyclic heterocycle, the heterocycle having a first nitrogen in an aromatic 5- or 6-membered first ring, with attachment of the heterocycle to A by way of said first nitrogen and said nitrogen is quaternary by virtue of the attachment in addition to the ring bonds thereto, with the first ring having 0 or 1 of either O or S, with the first ring having 0 to 3 additional nitrogen atoms, with the first ring optionally fused to a 3- or 4-membered moiety to form the optional second ring, with the moiety having at least one carbon atom, with the moiety having 0 to 1 of either O or S, with the moiety having 0 to 2 nitrogen atoms, and with the moiety being saturated or unsaturated and the second ring aromatic or non-aromatic;

R$^c$ is R$^a$ as defined under Type II below, hydrogen, or —NR$^y$R$^z$ (where R$^y$ and R$^z$ are defined type in II below), but independently selected from R$^a$ and from each other if more than one R$^c$ is present, and is attached to a carbon ring atom or a nitrogen heteroatom the valency of which is not satisfied by the ring bonds;

b)

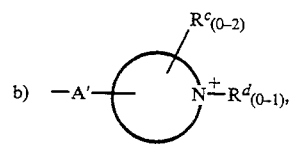

where

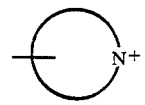

is a 5- or 6-membered monocyclic heterocycle or an 8-, 9- or 10-membered bicyclic heterocycle, the heterocycle having a first nitrogen in an aromatic 5- or 6-membered first ring, with said first nitrogen quaternary by virtue of a substituent R$^d$ in addition to the ring bonds thereto, with said first nitrogen neutral in the absence of a substituent R$^d$, with attachment of the heterocycle to A' by way of a carbon atom of a ring, with the first ring having 0 or 1 of either O or S, with the first ring having 0 to 2 additional nitrogen atoms, with the first ring optionally fused to a 3- or 4-membered moiety to form the optional second ring, with the moiety having at least one carbon atom, with the moiety having 0 or 1 of either O or S, with the moiety having 0 to 2 nitrogen atoms, and with the moiety being saturated or unsaturated and the second ring aromatic or non-aromatic;

R$^c$ is as defined above;

R$^d$ is hydrogen, NH$_2$, O$^-$, or C$_1$-C$_4$ alkyl (where the alkyl group is optionally mono-substituted with R$^q$ as defined under IIc below);

A' is (CH$_2$)$_m$—Q—(CH$_2$)$_n$, where m is 0 to 6 and n is 0 to 6, Q is as given above except that when m and n are both 0 then Q is not a covalent bond and (CH$_2$)$_m$ is attached to the fluoren-9-one moiety;

c) —A$_p$—N$^+$R$^y$(R$^w$)$_{(0-1)}$(R$^z$), where

R$^y$ and R$^z$ are as defined under II below, R$^y$ and R$^z$ may further be together a C$_2$-C$_4$ alkylidene radical to form a ring (optionally mono-substituted with R$^q$ as defined below) interrupted by N(O)R$^e$ or N$^+$(R$^e$)$_2$ (where R$^e$ is hydrogen, C$_1$-C$_4$ alkyl, or C$_1$-C$_4$ alkyl mono-substituted with R$^q$ as defined below), R$^w$ is hydrogen, C$_{1-4}$ alkyl, O$^-$, NH$_2$, or absent in which case the nitrogen is neutral, R$^w$, R$^y$ and R$^z$ may further together form a C$_5$-C$_{10}$ tertiary alkylidene radical which with N$^+$ forms a bicyclic ring, where the tertiary alkylidene radical is optionally mono-substituted with R$^q$ as defined below and where the tertiary carbon of the tertiary alkylidene radical is optionally replaced with nitrogen, $N^+R^e$ (where $R^e$ is defined above) or $N^+$—$O^-$, p is 0 or 1, and A is as defined above;

d)

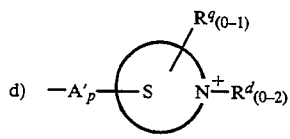

where

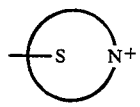

is a 5- or 6-membered monocyclic heterocycle or an 8-, 9- or 10-membered bicyclic heterocycle, the heterocycle having a first nitrogen in a first ring, with the first ring saturated or unsaturated and non-aromatic, with the first nitrogen quaternary by virtue of one or two substituents $R^d$ in addition to the ring bonds thereto, with the first nitrogen alternatively neutral by virtue of zero or one substituent $R^d$ in addition to the ring bonds thereto, with attachment of the heterocycle to A' by way of a carbon atom or non-quaternary nitrogen atom of a ring, with the first ring having in addition to carbon and the first nitrogen, 0 to 1 of a member selected from the group consisting of the non-quaternary nitrogen of attachment, O, S, S(O), S(O)$_2$ and NR$^e$, where R$^e$ is defined above, with the first ring optionally fused to a 2-, 3- or 4-membered moiety to form the optional second ring, with the moiety optionally having in addition to carbon the non-quaternary nitrogen of attachment, and with the moiety saturated or unsaturated and the second ring non-aromatic;

$R^d$ is defined above and where more than one $R^d$ is present on a nitrogen, at least one $R^d$ is hydrogen or $C_1$-$C_4$ alkyl;

A' is defined above;

p is defined above; and $R^q$ is defined below;

wherein the Type I, $R^a$ substituent is balanced with the anionic form of Z, where Z is a member selected from the group consisting of methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo and iodo;

and wherein the Type II substituents are:

Type II a) a trifluoromethyl group which is —$CF_3$;

b) a halogen atom selected from the group consisting of —Br, —Cl, —F, and —I;

c) $C_1$-$C_4$ alkoxy radical which is —$OC_{1-4}$ alkyl, wherein the alkyl is optionally mono-substituted by $R^q$, where $R^q$ is a member selected from the group consisting of —OH, —OP' (where P' is defined above), —$OCH_3$, —CN, —C(O)$NH_2$, —OC(O)$NH_2$, CHO, —OC(O)N(CH$_3$)$_2$, —$SO_2NH_2$, —$SO_2N(CH_3)_2$, —$SOCH_3$, —$SO_2CH_3$, —F, —$CF_3$, —COOM$^a$ (where M$^a$ is hydrogen, alkali metal, methyl, phenyl or M, where M is as defined below), tetrazolyl (where the point of attachment is the carbon atom of the tetrazole ring and one of the nitrogen atoms is mono-substituted by M$^a$ as defined above) and —$SO_3M^b$ (where M$^b$ is hydrogen, an alkali metal or M, where M is as defined below);

d) a hydroxy or protected hydroxy group which is —OH or —OP', where P' is as defined above;

e) a carbonyloxy radical which is —O(C=O)R$^s$, where

R$^s$ is $C_{1-4}$ alkyl or phenyl, each of which is optionally mono-substituted by R$^q$ as defined above;

f) a carbamoyloxy radical which is —O(C=O)N(R$^y$)R$^z$, where

R$^y$ and R$^z$ are independently H, $C_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)— or —S(O)$_2$— to form a ring (where the ring is optionally mono-substituted with R$^q$ as defined above);

g) a sulfur radical containing —S(O)$_n$—R$^s$ where n=0–2, and R$^s$ is defined above;

h) a sulfamoyl group which is —$SO_2N(R^y)R^z$ where R$^y$ and R$^z$ are as defined above;

i) azido which is $N_3$;

j) a formamido group which is —N(R$^t$)(C=O)H, where R$^t$ is H or $C_{1-4}$ alkyl, and the alkyl thereof is optionally mono-substituted by R$^q$ as defined above;

k) a ($C_1$-$C_4$ alkyl)carbonylamino radical which is —N(R$^t$)(C=O)$C_{1-4}$ alkyl, where R$^t$ is as defined above, and the alkyl group is also optionally mono-substituted by R$^q$ as defined above;

l) a ($C_1$-$C_4$ alkoxy)carbonylamino radical which is —N(R$^t$)(C=O)O$C_{1-4}$ alkyl, where R$^t$ is as defined above, and the alkyl group is also optionally mono-substituted by R$^q$ as defined above;

m) a ureido group which is —N(R$^t$)(C=O)N(R$^y$)R$^z$ where R$^t$, R$^y$ and R$^z$ are as defined above;

n) a sulfonamido group which is —N(R$^t$)$SO_2R^s$, where R$^s$ and R$^t$ are as defined above;

o) a cyano group which is —CN;

p) a formyl or acetalized formyl radical which is —(C=O)H or —CH(OCH$_3$)$_2$;

q) ($C_1$-$C_4$ alkyl)carbonyl radical wherein the carbonyl is acetalized which is —C(OCH$_3$)$_2$$C_{1-4}$ alkyl, where the alkyl is optionally mono-substituted by R$^q$ as defined above;

r) carbonyl radical which is —(C=O)R$^s$, where R$^s$ is as defined above;

s) a hydroxyiminomethyl radical in which the oxygen or carbon atom is optionally substituted by a $C_1$-$C_4$ alkyl group which is —(C=NOR$^z$)R$^y$ where R$^y$ and R$^z$ are as defined above, except they may not be joined together to form a ring;

t) a ($C_1$-$C_4$ alkoxy)carbonyl radical which is —(C=O)O$C_{1-4}$ alkyl, where the alkyl is optionally mono-substituted by R$^q$ as defined above;

u) a carbamoyl radical which is —(C=O)N(R$^y$)R$^z$ where R$^y$ and R$^z$ are as defined above;

v) an N-hydroxycarbamoyl or N(C$_1$-C$_4$ alkoxy)carbamoyl radical in which the nitrogen atom may be additionally substituted by a C$_1$-C$_4$ alkyl group which is —(C=O)—N(OR$^y$)R$^z$ where R$^y$ and R$^z$ are as defined above, except they may not be joined together to form a ring;

w) a thiocarbamoyl group which is —(C=S)N-(R$^y$)R$^z$ where R$^y$ and R$^z$ are as defined above;

x) carboxyl which is —COOM$^b$, where M$^b$ is as defined above;

y) thiocyanate which is : —SCN;

z) trifluoromethylthio which is —SCF$_3$;

aa) tetrazolyl, where the point of attachment is the carbon atom of the tetrazole ring and one of the nitrogen atoms is mono-substituted by hydrogen, an alkali metal or a C$_1$-C$_4$ alkyl optionally substituted by R$^q$ as defined above;

ab) an anionic function selected from the group consisting of: phosphono: [P=O(OM$^b$)$_2$]; alkylphosphono: {P=O(OM$^b$)—[O(C$_1$-C$_4$ alkyl)]}; alkylphosphinyl: [P=O(OM$^b$)—(C$_1$-C$_4$ alkyl)]; phosphoramido: [P=O(OM$^b$)N(R$^y$)R$^z$ and P=O-(OM$^b$)NHR$^x$]; sulfino: (SO$_2$M$^b$); sulfo: (SO$_3$M$^b$); acylsulfonamides selected from the structures: CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

ac) C$_5$-C$_7$ cycloalkyl group in which one of the carbon atoms in the ring is replaced by a heteroatom selected from O, S, NH, or N(C$_1$-C$_4$ alkyl) and in which one additional carbon may be replaced by NH or N(C$_1$-C$_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) C$_2$-C$_4$ alkenyl radical, optionally mono-substituted by one of the substituents a) to ac) above and phenyl which is optionally substituted by R$^q$ as defined above;

ae) C$_2$-C$_4$ alkynyl radical, optionally mono-substituted by one of the substituents a) to ac) above;

af) C$_1$-C$_4$ alkyl radical;

ag) C$_1$-C$_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from S and NR$^t$ (where R$^t$ is as defined above) and one of the saturated carbon atoms of the oxazolidinone ring is optionally mono-substituted by one of the substituents a) to ag) above;

M is a removable carboxyl protecting group.

2. The compound of claim 1 wherein M is selected from the group consisting of alkyl, substituted alkyl, benzyl, substituted benzyl, aryl, substituted aryl, allyl, substituted allyl and triorganosilyl.

3. The compound of claim 2 wherein M is selected from the group consisting of benzhydryl, p-nitrobenzyl, 2-naphthylmethyl, allyl, 2-chloroallyl, benzyl, 2,2,2-trichloroethyl, t-butyldimethylsilyl, t-butyldiphenylsilyl, 2-(trimethylsilyl)ethyl, phenacyl, p-methoxybenzyl, acetonyl, o-nitrobenzyl, p-methoxyphenyl, 4-pyridylmethyl and t-butyl.

4. The compound of claim 1 wherein P' is selected from the group consisting of trialkylsilyl, arylalkylalkoxysilyl, alkyldiarylsilyl, alkoxydiarylsilyl, aryldialkylsilyl, alkyloxycarbonyl, substituted alkyloxycarbonyl, benzyloxycarbonyl, substituted benzyloxycarbonyl allyloxycarbonyl and substituted allyloxycarbonyl.

5. The compound of claim 4 wherein P' is selected from the group consisting of trimethylsilyl, triethylsilyl, t-butyldimethylsilyl, t-butoxydiphenylsilyl, t-butylmethoxyphenylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

6. A compound of the formula:

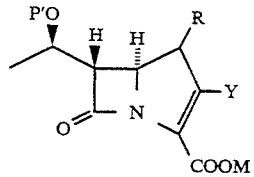

wherein
Y is

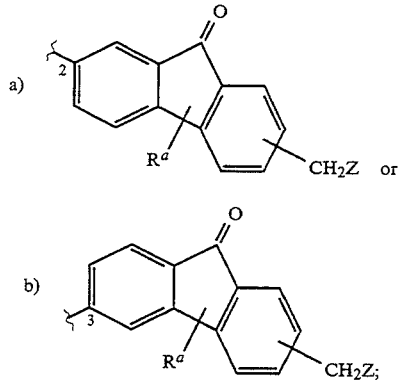

R is H or CH$_3$;

R$^a$ is selected from the group consisting of H, Br, Cl, I, CN, CHO, CO$_2$M, CO$_2$CH$_3$, CONH$_2$, OP', CH$_2$OP', CH=N—OCH$_3$, SCH$_3$, SOCH$_3$, and SO$_2$CH$_3$;

P' is a removable hydroxyl protecting group;

M is a removable carboxyl protecting group; and

Z is a leaving group selected from the group consisting of alkylsulfonyloxy, substituted alkylsulfonyloxy, arylsulfonyloxy, substituted arylsulfonyloxy, fluorosulfonyloxy and halogen.

7. The compound of claim 6 wherein M is selected from the group consisting of alkyl, substituted alkyl, benzyl, substituted benzyl, aryl, substituted aryl, allyl, substituted allyl and triorganosilyl.

8. The compound of claim 7 wherein M is selected from the group consisting of benzhydryl, p-nitrobenzyl, 2-naphthylmethyl, allyl, 2-chloroallyl, benzyl, 2,2,2-trichloroethyl, t-butyldimethylsilyl, t-butyldiphenylsilyl, 2-(trimethylsilyl)ethyl, phenacyl, p-methoxybenzyl, acetonyl, o-nitrobenzyl, p-methoxyphenyl, 4-pyridylmethyl and t-butyl.

9. The compound of claim 6 wherein P' is selected from the group consisting of trialkylsilyl, arylalkylalkoxysilyl, alkyldiarylsilyl, alkoxydiarylsilyl, aryldialkylsilyl, alkyloxycarbonyl, substituted alkyloxycarbonyl, benzyloxycarbonyl, substituted benzyloxycarbonyl allyloxycarbonyl and substituted allyloxycarbonyl.

10. The compound of claim 9 wherein P' is selected from the group consisting of trimethylsilyl, triethylsilyl, t-butyldimethylsilyl, t-butoxydiphenylsilyl, t-butylmethoxyphenylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

11. The compound of claim 6 wherein Z is selected form the group consisting of methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo and iodo.

12. A compound of the formula:

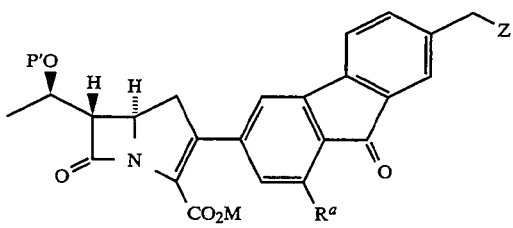

wherein
$R^a$ is selected from the group consisting of H, Br, Cl, I, CN, CHO, $CO_2M$, $CO_2CH_3$, $CONH_2$, OP', $CH_2OP'$, CH=N—$OCH_3$, $SCH_3$, $SOCH_3$, and $SO_2CH_3$;

P' is a removable hydroxyl protecting group
M is a removable carboxyl protecting group, and
Z is a leaving group selected from the group consisting of alkylsulfonyloxy, substituted alkylsulfonyloxy, arylsulfonyloxy, substituted arylsulfonyloxy, fluorosulfonyloxy and halogen.

13. The compound of claim 12 wherein P' is selected from the group consisting of trimethylsilyl, triethylsilyl, t-butyldimethylsilyl, t-butoxydiphenylsilyl, t-butylmethoxyphenylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

14. The compound of claim 13 wherein M is selected from the group consisting of benzhydryl, p-nitrobenzyl, 2-naphthylmethyl, allyl, 2-chloroallyl, benzyl, 2,2,2-trichloroethyl, t-butyldimethylsilyl, t-butyldiphenylsilyl, 2-(trimethylsilyl)ethyl, phenacyl, p-methoxybenzyl, acetonyl, o-nitrobenzyl, p-methoxyphenyl, 4-pyridylmethyl and t-butyl.

15. The compound of claim 14 wherein Z is selected form the group consisting of methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo and iodo.

16. The compound of claim 15 wherein $R^a$ is hydrogen, P' is triethylsilyl or trimethylsilyl; Z is trifluoromethanesulfonyloxy and M is p-nitrobenzyl.

17. A carbapenem compound of the formula:

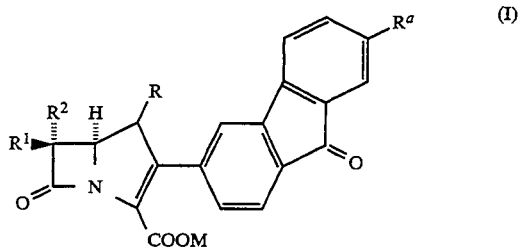

wherein:
R is H or $CH_3$;
$R^1$ and $R^2$ are independently H, $CH_3$—, $CH_3CH_2$—, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;
$R^a$ is —$A_p$—$N^+R^y(R^w)_{(0-1)}(R^z)$, where
$R^y$ and $R^z$ may be together a $C_{1-4}$ alkylidene radical to form a ring (optionally substituted with $R^q$) interrupted by $N(O)R^e$ or $N^+(R^e)_2$ (where each $R^e$ is independently selected from H, $C_{1-4}$ alkyl, or $C_{1-4}$ alkyl mono substituted with $R^q$;
$R^w$ is hydrogen, $C_{1-4}$ alkyl, $O^\ominus$, $NH_2$ or absent in which case the nitrogen is neutral;
$R^w$, $R^y$ and $R^z$ may further form a $C_{5-10}$ tertiary alkylidene radical which with $N^+$ forms a bicyclic ring where the tertiary alkylidene radical is optionally monosubstituted with $R^q$ and where the tertiary carbon of the tertiary alkylidene radical is optionally replaced with nitrogen, $N^+R^e$, or $N^+$—$O^-$; p is 1;
$R^q$ is a member selected from the group consisting of —OH, —$OCH_3$, —CN, —$C(O)NH_2$, —OC(O)$NH_2$, CHO, —OC(O)N($CH_3$)$_2$, —$SO_2NH_2$, —$SO_2N(CH_3)_2$, —$SOCH_3$, —$SO_2CH_3$, —F, and —$CF_3$; each
$R^e$ is hydrogen or $C_{1-4}$ alkyl wherein $C_{1-4}$ alkyl is optionally mono-substituted with $R^q$
A is $C_{1-6}$ alkyl; and
M is selected from:
  i) hydrogen;
  ii) a pharmaceutically acceptable esterifying group or removable carboxyl protecting group;
  iii) an alkali metal or other pharmaceutically acceptable cation; or
  iv) a negative charge.

18. A carbapenem compound of the formula:

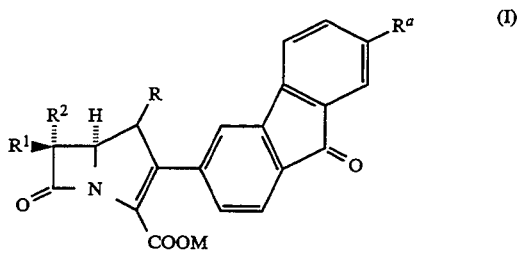

wherein:

R is H or CH$_3$;

R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

R$^a$ is selected from the group consisting of

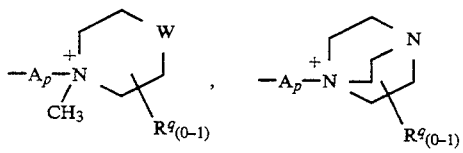,

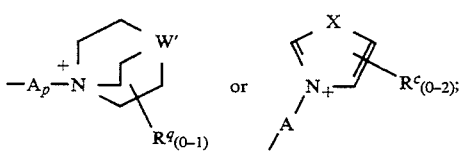

X is NR$^c$;

p is 1;

W is NR$^e$, or Z$^-$N$^+$(R$^e$)$_2$;

W' is Z$^-$N$^+$R$^e$, or NO, wherein Z$^-$ represents a member selected from the group consisting of the anionic forms of methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo and iodo and where R$^q$ is shown to have an indefinite position, it may be attached to any carbon atom of the ring; each R$^q$ is a member selected from the group consisting of —OH, —CN, —C(O)NH$_2$, —OC(O)NH$_2$, —OC(O)N(CH$_3$)$_2$, —SO$_2$NH$_2$, —SO$_2$N(CH$_3$)$_2$, and —SO$_2$CH$_3$;

R$^c$ is C$_{1-4}$alkyl, wherein the C$_{1-4}$alkyl is optionally substituted with R$_q$; each R$^e$ is independently hydrogen or C$_{1-4}$ alkyl wherein C$_{1-4}$ alkyl is optionally substituted with R$^q$;

A is C$_{1-6}$ alkyl; and

M is selected from:
i) hydrogen;
ii) a pharmaceutically acceptable esterifying group or removable carboxyl protecting group;
iii) an alkali metal or other pharmaceutically acceptable cation; or
iv) a negative charge.

19. The compound of claim 18, wherein R$^1$ is hydrogen and R$^2$ is (R)—CH$_3$CH(OH)—.

20. The compound according to claim 19 wherein each R$^q$ is independently selected from the group consisting of —OH, —CN, —C(O)NH$_2$, and —SO$_2$NH$_2$.

21. The compound according to claim 20 wherein R$^a$ is selected from the group consisting of

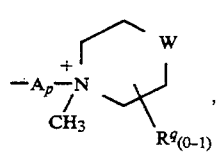,

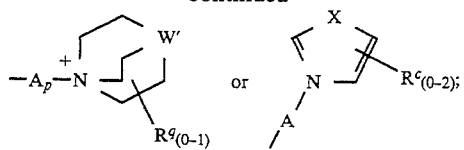

22. The compound according to claim 21 wherein:
W is N$^+$(C$_{1-4}$alkyl)R$^e$, wherein Re is methyl monosubstituted with R$^q$;
W' is N$^+$R$^e$; and
X is NR$^c$ wherein R$^c$ is ethyl monosubstituted with R$^q$.

23. The compound according to claim 22 wherein R$^a$ is selected from

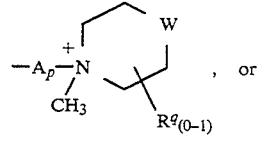

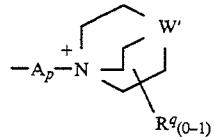

24. The compound according to claim 22 wherein R$^a$ is selected from the group consisting of

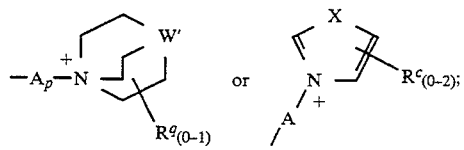

25. The compound according to claim 22 wherein R$^a$ is selected from the group consisting of

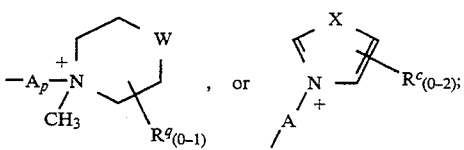

26. The compound according to claim 22 wherein R is β-methyl or hydrogen.

27. The composition comprising a pharmaceutically acceptable carrier and from 0.1% to about 99% by weight of active material of claim 18.

28. The composition according to claim 27 which further comprises an inhibitorily effective amount of a DHP inhibitor.

29. The composition according to claim 28 wherein said DHP inhibitor is 7-(L-2-amino-2-carboxyethylthio)-2-(2,2-dimethylcyclopropanecarboxamide)-2-heptanoic acid.

30. A method for treating bacterial infection in mammals comprising administering a pharmaceutical composition comprising an effective amount of a compound of claim 18 and a pharmaceutically acceptable carrier therefor.

31. The method according to claim 30 which further comprises administering an inhibitorily effective amount of a DHP inhibitor.

32. The method according to claim 31 wherein said DHP inhibitor is 7-(L-2-amino-2-carboxyethylthio)-2-(2,2-dimethylcyclopropanecarboxamide)-2-heptanoic acid.

* * * * *